United States Patent
Buchsbaum

(10) Patent No.: US 10,449,391 B2
(45) Date of Patent: Oct. 22, 2019

(54) SYSTEM AND METHOD FOR REDUCING BIOLOGICAL DAMAGE IN PROTON THERAPY

(71) Applicant: Indiana University Research and Technology Corporation, Indianapolis, IN (US)

(72) Inventor: Jeffrey Buchsbaum, Gaithersburg, MD (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 6 days.

(21) Appl. No.: 15/327,337

(22) PCT Filed: Jul. 24, 2015

(86) PCT No.: PCT/US2015/042051
§ 371 (c)(1),
(2) Date: Jan. 18, 2017

(87) PCT Pub. No.: WO2016/014972
PCT Pub. Date: Jan. 28, 2016

(65) Prior Publication Data
US 2017/0157426 A1    Jun. 8, 2017

Related U.S. Application Data

(60) Provisional application No. 62/029,103, filed on Jul. 25, 2014.

(51) Int. Cl.
*A61N 5/10* (2006.01)
(52) U.S. Cl.
CPC ......... *A61N 5/1067* (2013.01); *A61N 5/1031* (2013.01); *A61N 2005/1087* (2013.01)

(58) Field of Classification Search
CPC .. A61N 5/1031; A61N 5/1047; A61N 5/1048; A61N 5/1067; A61N 5/1071; A61N 2005/1087
See application file for complete search history.

(56) References Cited

U.S. PATENT DOCUMENTS 7,268,358 B2    9/2007    Ma et al.
8,193,508 B2    6/2012    Shchory et al.
(Continued)

OTHER PUBLICATIONS

Search Report and Written Opinion issued by the ISA/US, Commission for Patents, dated Oct. 23, 2015, for International Application No. PCT/US2015/042051; 6 pages.
(Continued)

*Primary Examiner* — Carrie R Dorna
(74) *Attorney, Agent, or Firm* — Faegre Baker Daniels LLP

(57) ABSTRACT

Systems comprising a processor in electrical communication with a tangible, non-transitory memory that, in response to an execution by the processor, cause the processor to measure a relative biological effectiveness of a beam on a region of a human body, and a beam applicator in electrical communication with the processor, wherein a characteristic of the beam can be adjusted based on the measured relative biological effectiveness are disclosed. Methods of treatment comprising measuring, by a processor capable of detecting potential biological hot spots, a relative biological effectiveness of a beam on a region of a human body, designing a beam therapy treatment plan based on the measured relative biological effectiveness, and applying a beam to a patient with a region in need of beam therapy with a beam applicator in electrical communication with the processor capable of detecting potential biological hot spots are also disclosed.

20 Claims, 50 Drawing Sheets

(56) References Cited

U.S. PATENT DOCUMENTS 8,357,907 B2  1/2013  Testa et al.
8,546,774 B2  10/2013  Keppel et al.

OTHER PUBLICATIONS

International Preliminary Report on Patentability issued by The International Bureau of WPIO, dated Jan. 31, 2017, for International Application No. PCT/US2015/042051; 5 pages.

Buchsbaum et al., "Range modulation in proton therapy planning: a simple mehtod for mitigating effects of increased relative biological effectiveness at the end-of-range of clinical proton beams." *Radiation Oncology* 2014, 9:2.

M. N. Rosenbluth, "High Energy Elastic Scattering of Electrons on Protons," *Phys. Rev.*, vol. 79, No. 4, pp. 615-619, Aug. 1950.

"Northeast Proton Therapy Center, Massachusetts General Hospital Cancer Center," http://neurosurgery.mgh.harvard.edu/ProtonBeam/NPTCbrochure.pdf, Jul. 7, 2005. .

S. P. Jackson, "Sensing and repairing DNA double-strand breaks," *Carcinogenesis*, vol. 23, No. 5, pp. 687-696, May 2002.

A. Wambersie, "RBE, reference RBE and clinical RBE: Applications of these concepts in hadron therapy," *Strahlenther. Onkol.*, vol. 175, No. 2, pp. 39-43, Jun. 1999.

G. Kraft, "Tumor therapy with heavy charged particles," *Prog. Part. Nucl. Phys.*, vol. 45, Supplement 2, pp. S473-S544, 2000.

R. A. Britten, V. Nazaryan, L. K. Davis, S. B. Klein, D. Nichiporov, M. S. Mendonca, M. Wolanski, X. Nie, J. George, and C. Keppel, "Variations in the RBE for Cell Killing Along the Depth-Dose Profile of a Modulated Proton Therapy Beam," *Radiat. Res.*, vol. 179, No. 1, pp. 21-28, Jan. 2013.

J. N. Kavanagh, K. M. Redmond, G. Schettino, and K. M. Prise, "DNA Double Strand Break Repair: A Radiation Perspective," *Antioxid. Redox Signal.*, vol. 18, No. 18, pp. 2458-2472, Jun. 2013.

L. Skarsgard, "Radiobiology with heavy charged particles: a historical review.," *Phys. Medica PM Int. J. Devoted Appl. Phys. Med. Biol. Off. J. Ital. Assoc. Biomed. Phys. AIFB*, vol. 14 Suppl 1, pp. 1-19, Jul. 1998.

H. Paganetti, A. Niemierko, M. Ancukiewicz, L. E. Gerweck, M. Goitein, J. S. Loeffler, and H. D. Suit, "Relative biological effectiveness (RBE) values for proton beam therapy," *Int. J. Radiat. Oncol.*, vol. 53, No. 2, pp. 407-421, Jun. 2002.

M. C. Frese, V. K. Yu, R. D. Stewart, and D. J. Carlson, "A Mechanism-Based Approach to Predict the Relative Biological Effectiveness of Protons and Carbon Ions in Radiation Therapy," *Int. J. Radiat. Oncol.*, vol. 83, No. 1, pp. 442-450, May 2012.

A. Carabe, M. Moteabbed, N. Depauw, J. Schuemann, and H. Paganetti, "Range uncertainty in proton therapy due to variable biological effectiveness," *Phys. Med. Biol.*, vol. 57, No. 5, p. 1159, Mar. 2012.

L. E. Gerweck and S. V. Kozin, "Relative biological effectiveness of proton beams in clinical.therapy," *Radiother. Oncol.*, vol. 50, No. 2, pp. 135-142, Feb. 1999.

A. Courdi, N. Brassart, J. Herault, and P. Chauvel, "The depth-dependent radiation response of human melanoma cells exposed to 65 MeV protons," *Br. J. Radiol*, vol. 67, No. 800, pp. 800-804, Aug. 1994.

M. Belli F. Cera R. Cherubini M. Dalla, "RBE-LET relationships for cell inactivation and mutation induced by low energy protons in V79 cells: further results at the LNL facility," *Int. J. Radiat. Biol.*, vol. 74, No. 4, pp. 501-509, Jan. 1998.

D. Bettega, P. Calzolari, P. Chauvel, "Radiobiological studies on the 65MeV therapeutic proton beam at Nice using human tumour cells," *Int. J. Radiat. Biol.*, vol. 76, No. 10, pp. 1297-1303, Jan. 2000.

V. Calugaru, C. Nauraye, G. Noël, N. Giocanti, V. Favaudon, and F. Mégnin-Chanet,"Radiobiological Characterization of Two Therapeutic Proton Beams With Different Initial Energy Spectra Used at the Institut Curie Proton Therapy Center in Orsay," *Int. J. Radiat. Oncol.*, vol. 81, No. 4, pp. 1136-1143, Nov. 2011.

J. Gueulette, V. Grégoire, M. Octave-Prignot, and A. Wambersie, "Measurements of Radiobiological Effectiveness in the 85 MeV Proton Beam Produced at the Cyclotron Cyclone of Louvain-la-Neuve, Belgium," *Radiation Research: Official Journal of the Radiation Research Society*, Apr. 9, 2010. [Online]. Available: http://www.rrjournal.org/doi/abs/10.2307/3579197. [Accessed: Mar. 11, 2014].

D. Bettega P. Calzolari R. Marchesini, "Inactivation of C3H10T1/2 cells by low energy protons and deuterons," *Int. J Radiat. Biol.*, vol. 73, No. 3, pp. 303-309, Jan. 1998.

M. C. Frese, J. J. Wilkens, P. E. Huber, A. D. Jensen, U. Oelfke, and Z. Taheri-Kadkhoda, "Application of Constant vs. Variable Relative Biological Effectiveness in Treatment Planning of Intensity-Modulated Proton Therapy," *Int. J. Radiat. Oncol.*, vol. 79, No. 1, pp. 80-88, Jan. 2011.

J. Tang, T. Inoue, H. Yamazaki, S. Fukushima, N. Fournier-Bidoz, M. Koizumi, S. Ozeki, and K. Hatanaka, "Comparison of radiobiological effective depths in 65-MeV modulated proton beams., Comparison of radiobiological effective depths in 65-MeV modulated proton beams.," *Br. J. Cancer Br. J. Cancer*, vol. 76, 76, No. 2, 2, pp. 220, 220-225, 1997.

J. Gueulette, L. Böhm, J. P. Slabbert, B. M. De Coster, G. S. Rutherfoord, A. Ruifrok, M. Octave-Prignot, P. J. Binns, A. N. Schreuder, J. E. Symons, P. Scalliet, and D. T. L. Jones, "Proton relative biological effectiveness (RBE) for survival in mice after thoracic irradiation with fractionated doses," *Int. J. Radiat. Oncol.*, vol. 47, No. 4, pp. 1051-1058, Jul. 2000.

Gueulette, L. Böhm, B.-M. De Coster, S. Vynckier, M. Octave-Prignot, A. N. Schreuder, J. E. Symons, D. T. L. Jones, A. Wambersie, and P. Scalliet, "RBE variation as a function of depth in the 200-MeV proton beam produced at the National Accelerator Centre in Faure (South Africa)," *Radiother. Oncol.*, vol. 42, No. 3, pp. 303-309, Mar. 1997.

K. H. Karlsson and B. Stenerlöw, "Focus Formation of DNA Repair Proteins in Normal and Repair-Deficient Cells Irradiated with High-LET Ions," *Radiation Research: Official Journal of the Radiation Research Society*, Oct. 1, 2009. [Online]. Available: http://www.rrjournal.org/doi/abs/10.1667/RR3171. [Accessed: Mar. 12, 2014].

E. Blomquist, K. R. Russell, B. Stenerlöw, A. Montelius, E. Grusell, and J. Carlsson, "Relative biological effectiveness of intermediate energy protons. Comparisons with 60Co gamma-radiation using two cell lines," *Radiother. Oncol.*, vol. 28, No. 1, pp. 44-51, Jul. 1993.

B. G. Wouters, G. K. Y. Lam, U. Oelfke, K. Gardey, R. E. Durand, and L. D. Skarsgard,"Measurements of Relative Biological Effectiveness of the 70 MeV Proton Beam at TRIUMF Using Chinese Hamster V79 Cells and the High-Precision Cell Sorter Assay," *Radiation Research: Official Journal of the Radiation Research Society*, May 7, 2010. [Online]Available: http://www.rrjournal.org/doi/abs/10.2307/3579588. [Accessed: Mar. 12, 2014].

G. Coutrakon, J. Cortese, A. Ghebremedhin, J. Hubbard, J. Johanning, P. Koss, G. Maudsley, C. R. Slater, C. Zuccarelli, and J. Robertson, "Microdosimetry spectra of the Loma Linda proton beam and relative biological effectiveness comparisons," *Med. Phys.*, vol. 24, No. 9, pp. 1499-1506, Sep. 1997.

J. B. Robertson, J. M. Eaddy, J. O. Archambeau, G. B. Coutrakon, D. W. Miller, M. F. Moyers, J. V. Siebers, J. M. Slater, and J. F. Dicello, "Relative biological effectiveness and microdosimetry of a mixed energy field of protons up to 200 MeV," *Adv. Space Res.*, vol. 14, No. 10, pp. 271-275, Oct. 1994.

J. Gueulette, J. P. Slabbert, L. Böhm, B. M. De Coster, J.-F. Rosier, M. Octave-Prignot, A. Ruifrok, A. Nicolaas Schreuder, A. Wambersie, P. Scalliet, and D. T. L. Jones, "Proton RBE for early intestinal tolerance in mice after fractionated irradiation," *Radiother. Oncol.*, vol. 61, No. 2, pp. 177-184, Nov. 2001.

K. Ando, Y. Furusawa, M. Suzuki, K. Nojima, H. Majima, S. Koike, M. Aoki, W. Shimizu, Y. Futami, T. Ogino, S. Murayama, and H. Ikeda, "Relative Biological Effectiveness of the 235 MeV Proton Beams at the National Cancer Center Hospital East," *J. Radiat. Res. (Tokyo)*, vol. 42, No. 1, pp. 79-89, Mar. 2001.

M. Urano, L. J. Verhey, M. Goitein, J. E. Tepper, H. D. Suit, D. Phil, O. Mendiondo, E. S. Gragoudas, and A. Koehler, "Relative bio-

(56) References Cited

OTHER PUBLICATIONS logical effectiveness of modulated proton beams in various murine tissues," *Int. J. Radiat. Oncol.*, vol. 10, No. 4, pp. 509-514, Apr. 1984.

M. W. McDonald, M. R. Wolanski, J. W. Simmons, and J. C. Buchsbaum, "Technique for sparing previously irradiated critical normal structures in salvage proton craniospinal irradiation," *Radiat. Oncol.*, vol. 8, No. 1, p. 14, Jan. 2013.

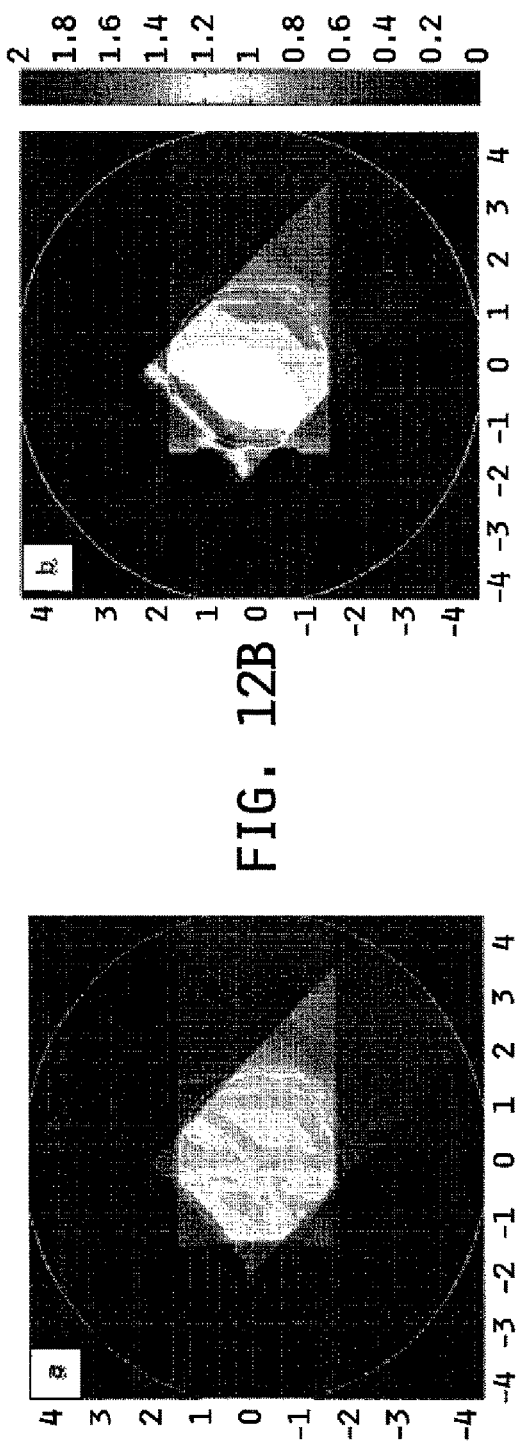
FIG. 12A
FIG. 12B
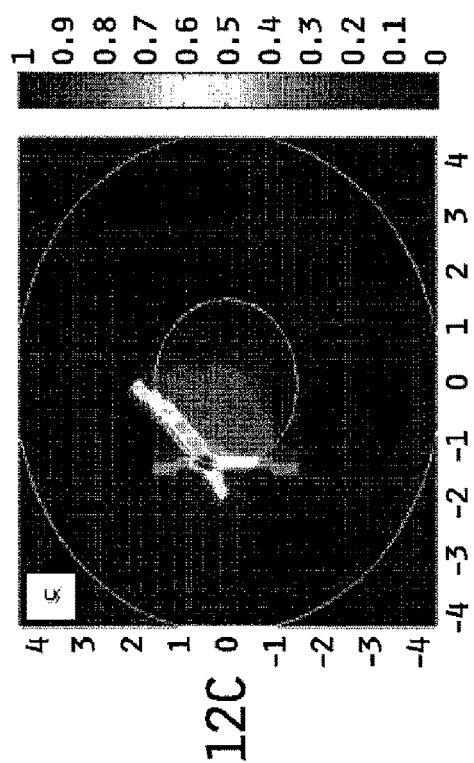
FIG. 12C

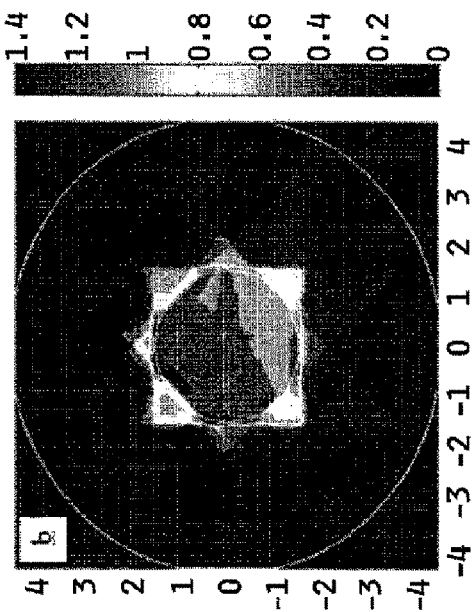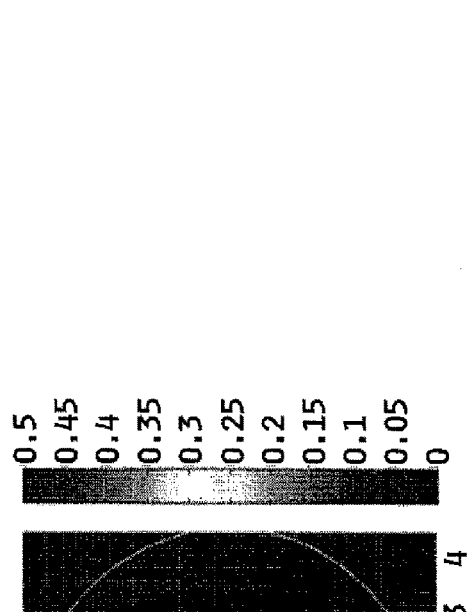
FIG. 25B
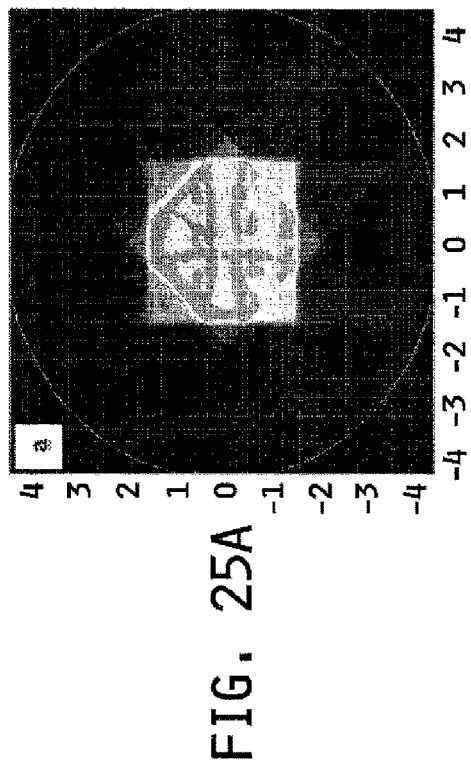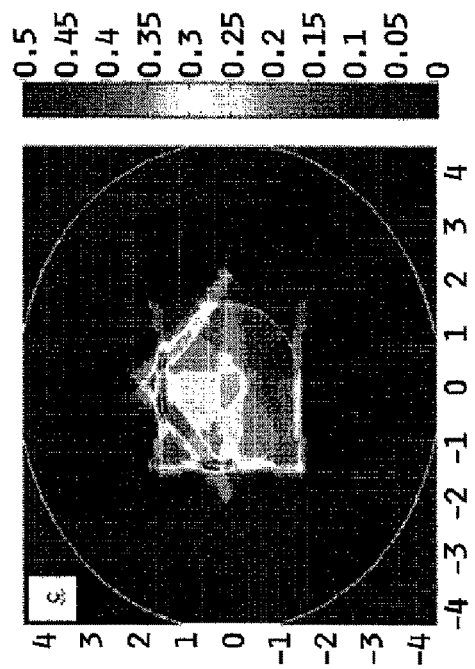
FIG. 25A
FIG. 25C

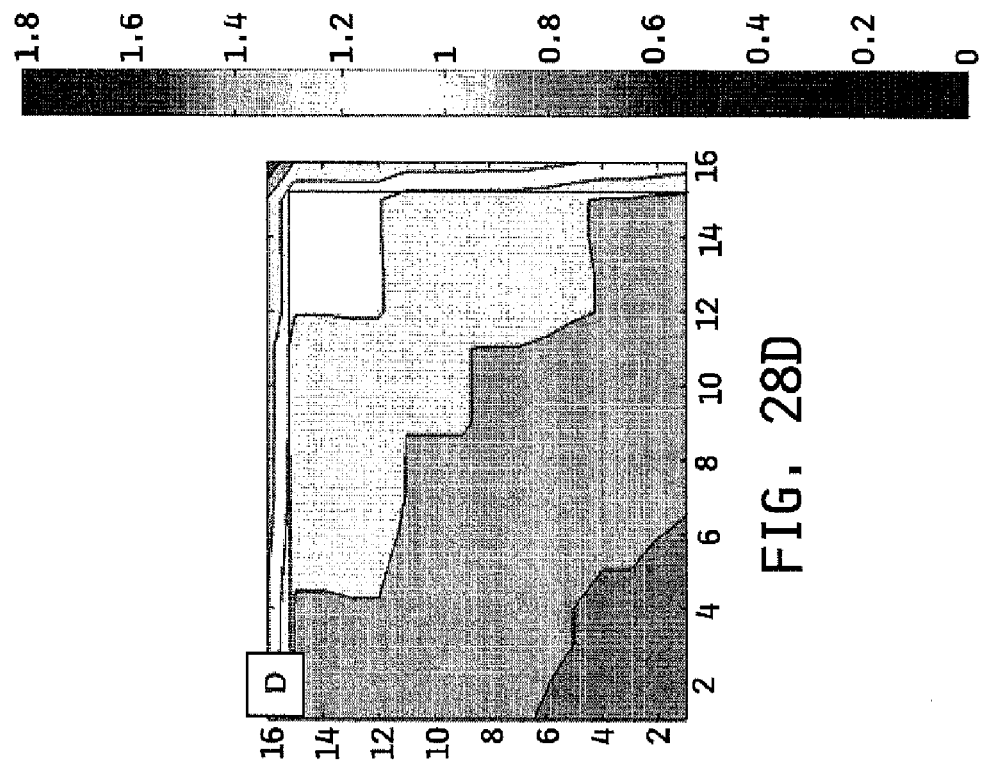
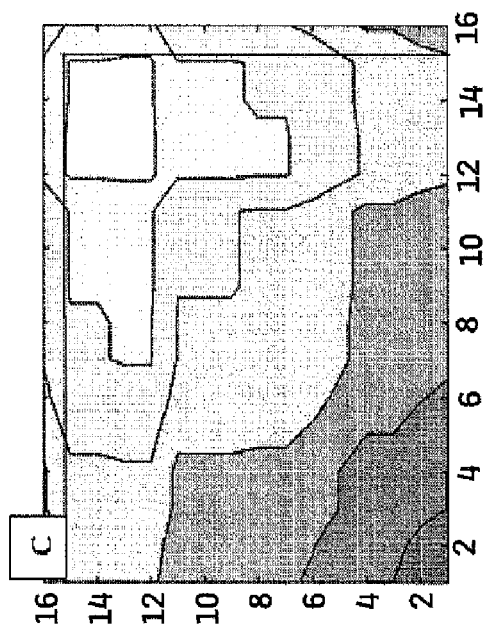
FIG. 28D
FIG. 28C

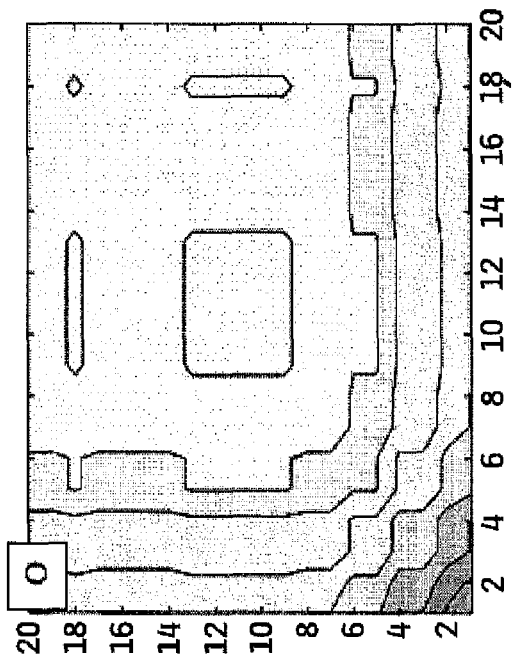
FIG. 28O
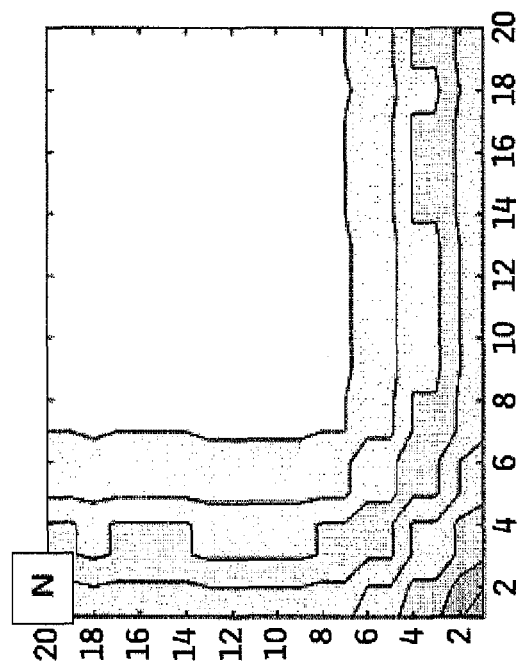
FIG. 28N

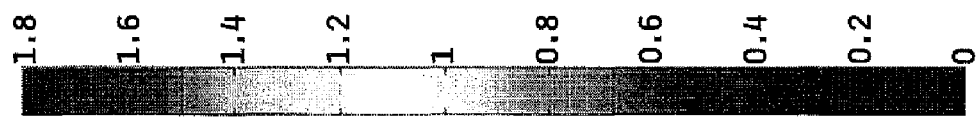
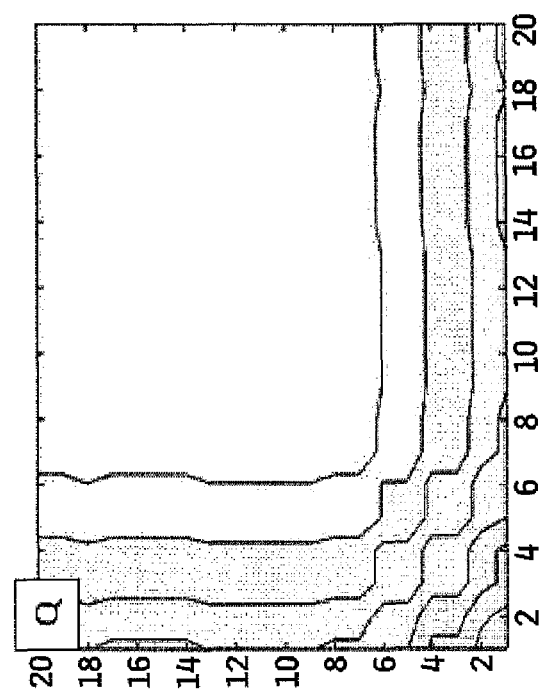
FIG. 28Q
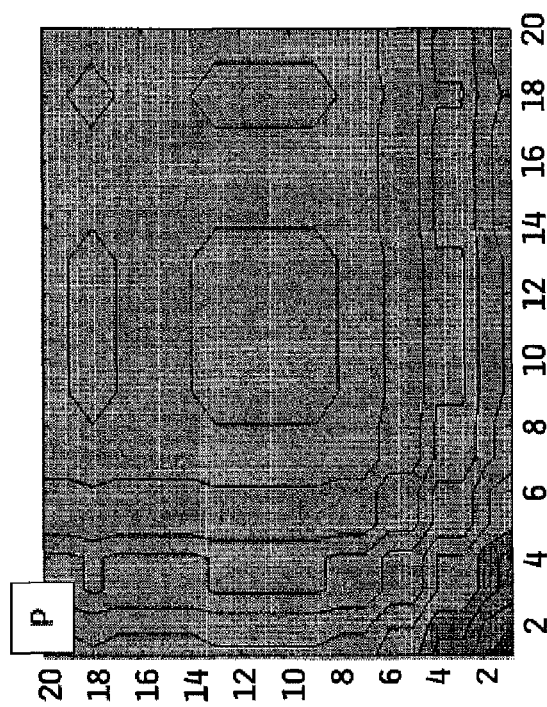
FIG. 28P

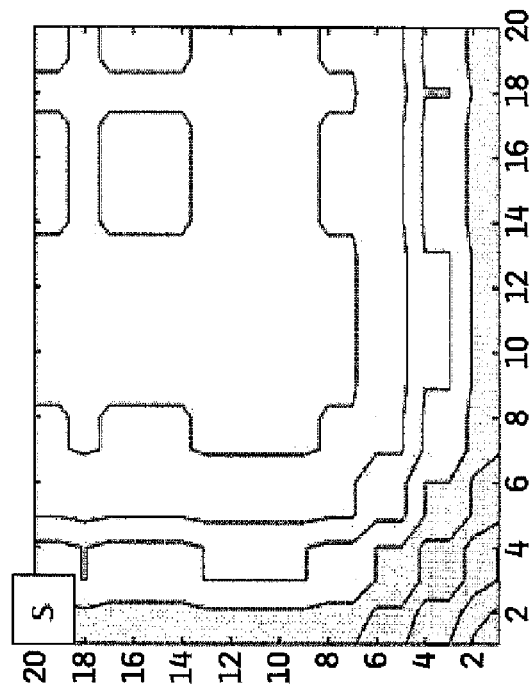
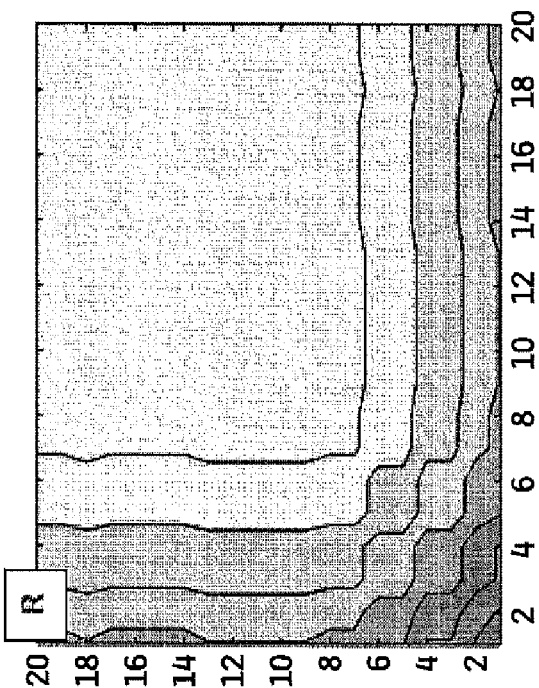
FIG. 28S
FIG. 28R

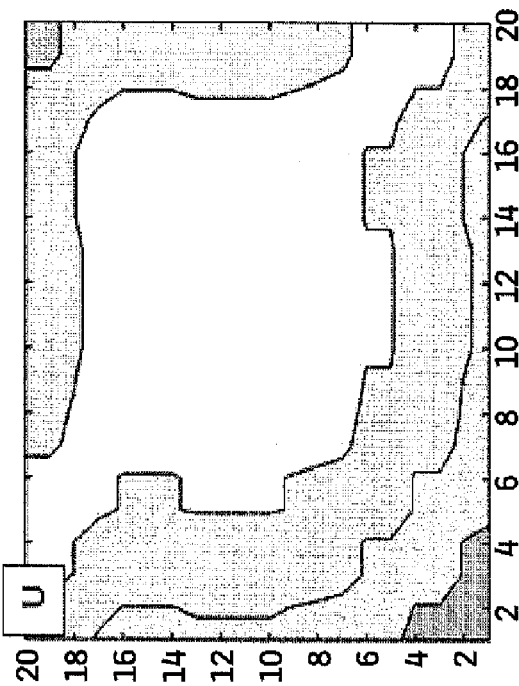
FIG. 28U
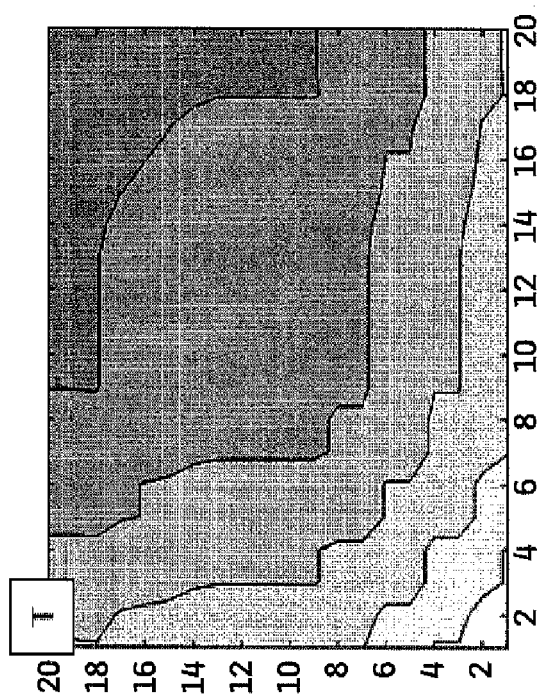
FIG. 28T

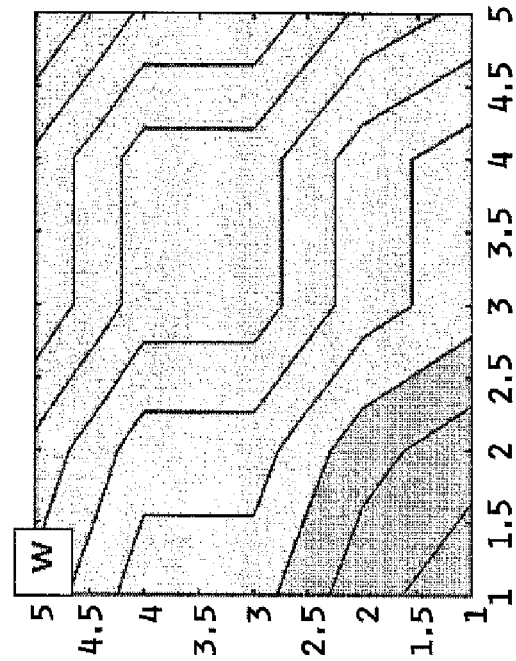
FIG. 28W
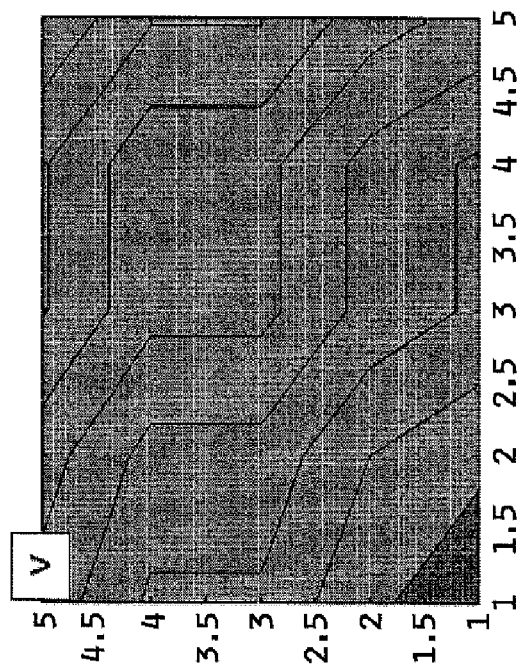
FIG. 28V

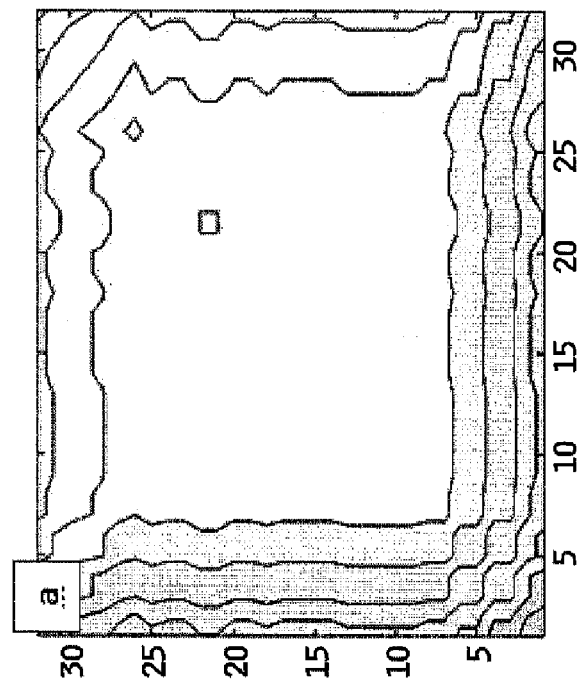
FIG. 28AA
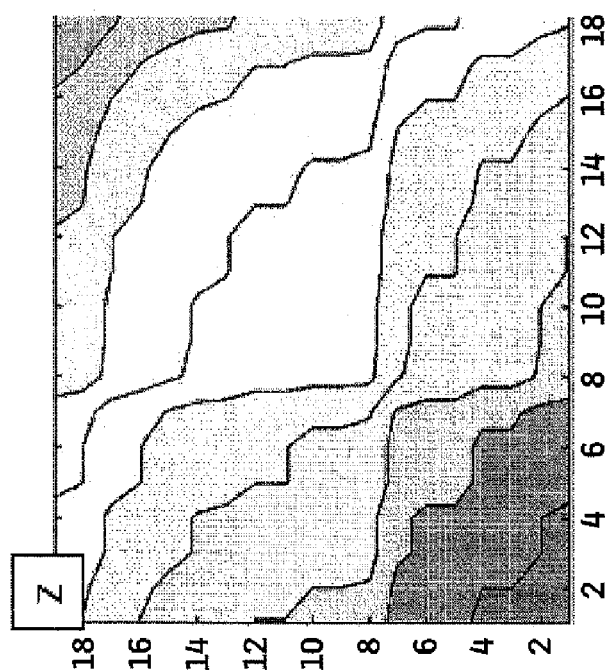
FIG. 28Z

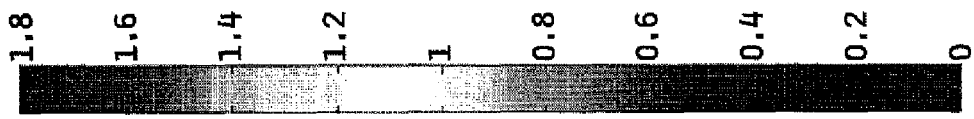
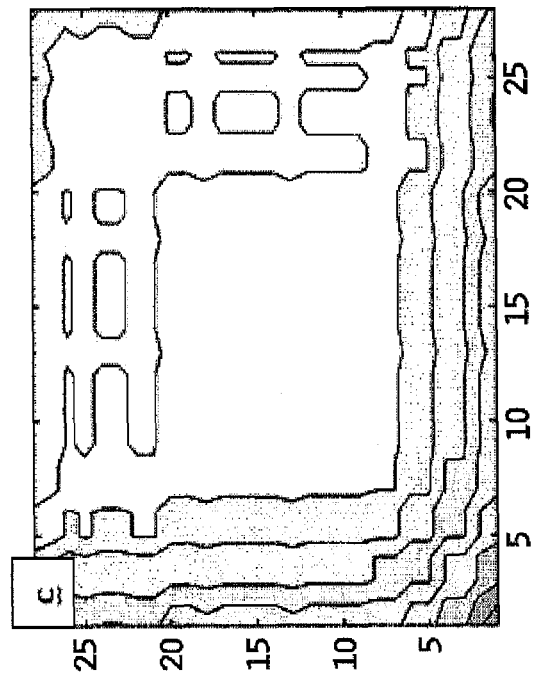
FIG. 28CC
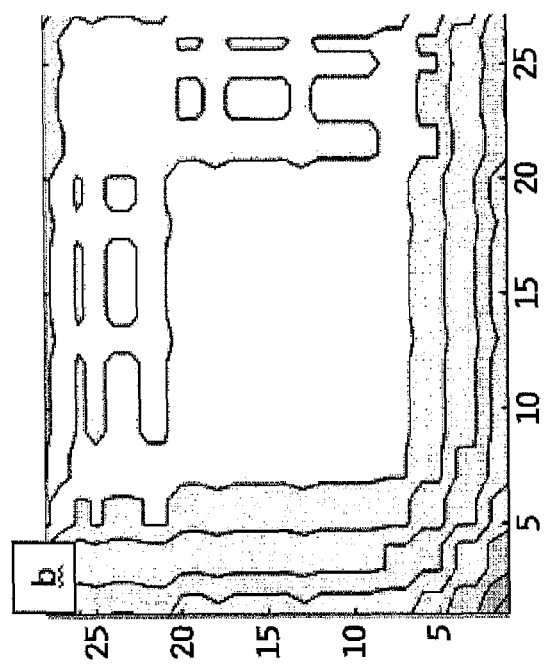
FIG. 28BB

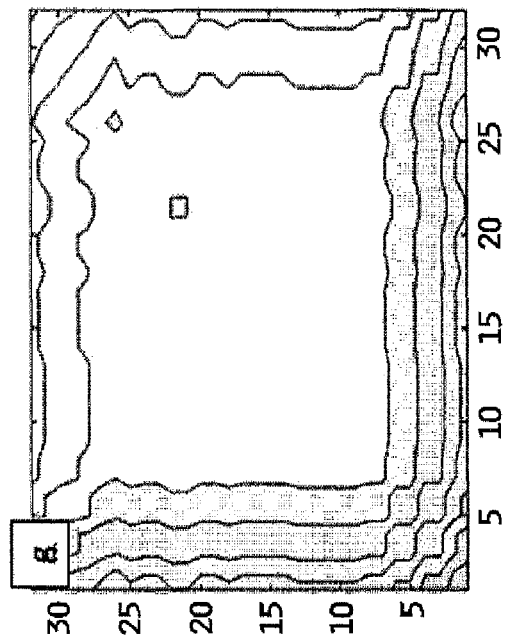
FIG. 28GG
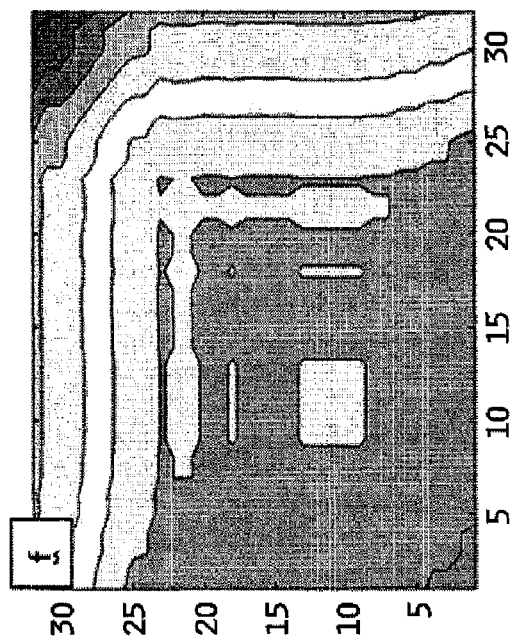
FIG. 28FF

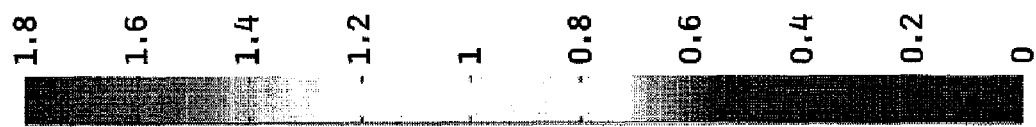
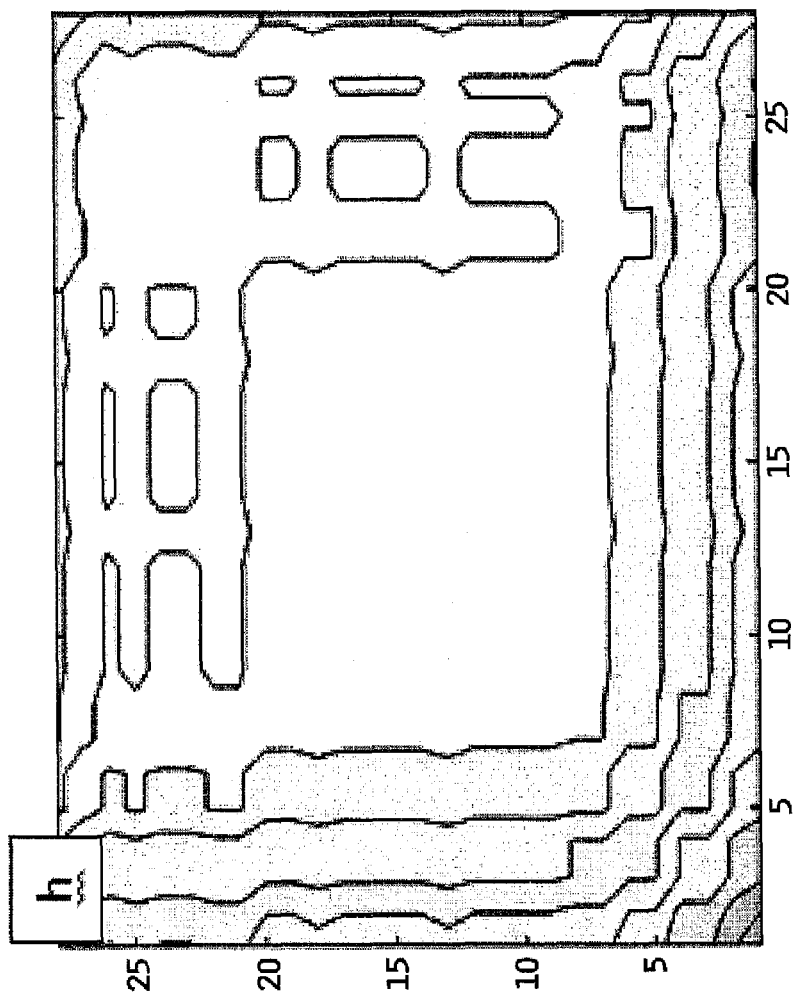
FIG. 28HH

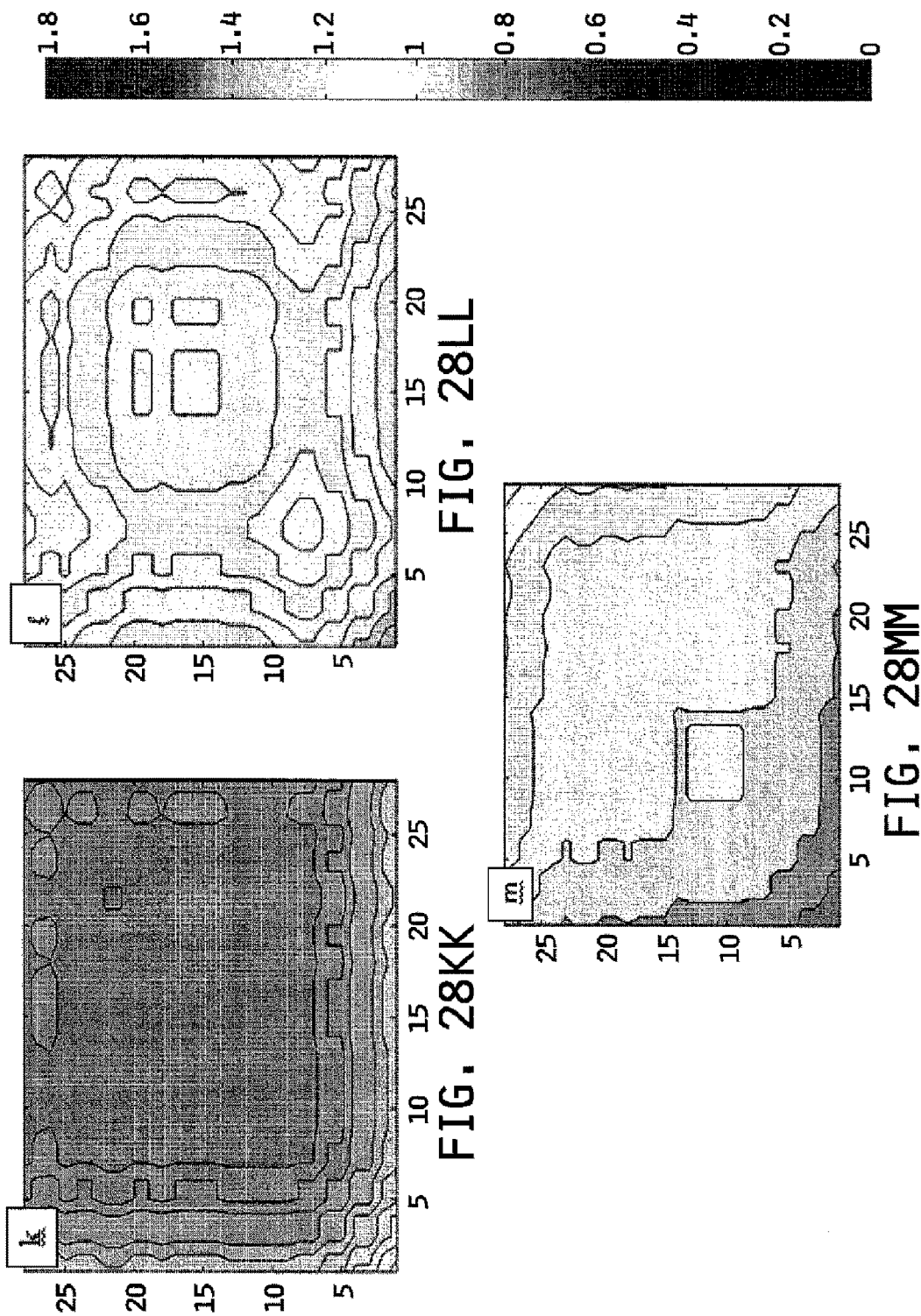

SYSTEM AND METHOD FOR REDUCING BIOLOGICAL DAMAGE IN PROTON THERAPY

CROSS-REFERENCE TO RELATED APPLICATIONS

This application is a U.S. National Stage Application of International Patent Application No. PCT/US2015/042051, filed Jul. 24, 2015, which claims the benefit of U.S. Provisional Patent Application Ser. No. 62/029,103, filed Jul. 25, 2014, the entire disclosure of which is hereby expressly incorporated by reference.

FIELD

The present disclosure relates generally to a system for reducing biological damage caused by the application of proton beam therapy. More particularly, the present disclosure relates to a method of planning and treatment to reduce biological damage caused by the application of proton beam therapy.

BACKGROUND

Although radiation is harmful to all tissues, malignant or healthy, most cancer cells lack control over DNA repair mechanisms. One of the greatest challenges of radiotherapy, for example in the treatment of cancer, is to minimize damage to normal cells while delivering a sufficient dose to kill tumor cells.

The main advantage of Proton beam therapy ("PBT") over conventional radiotherapy ("RT") is the more precise geometrical shape of the energy deposition inside the patient. The Bragg peak at the end of the proton range allows delivery of an accurate dose in a deep seated cancer, which also reduces the dose to surrounding normal tissues. The proton beam causes higher density of ionization events along its track, which can result in irreparable damage. The irreparable damage is more apparent at the end of the beam path and is the origin of the enhanced biological efficiency in the Bragg peak region. This biological efficiency is called Relative Biological Effectiveness ("RBE") and depends upon many biological and physical parameters.

Many techniques have been developed in order to protect normal tissue and maximize dose to the tumor using photon-based conventional radiotherapy. Three-Dimensional Conformal Radiation Therapy ("3D-CRT") uses several shaped beams converging in the tumor to reduce the dose on surrounding cells and nearby structures. Intensity Modulated Radiation Therapy ("IMRT") uses a multi-leaf collimator to enable modification of the photon fluence within the target while delivering non-coplanar 3D-CRT. Stereotactic Radiosurgery ("SRS") and Stereotactic Body Radiotherapy ("SBRT") may be coplanar or non-coplanar, use high doses per fraction, and are generally delivered to small (~10 cm) targets.

The depth of maximum dose thereby increases with energy. Beyond the maximum depth dose, beam hardening shifts the energy profile and higher energy leads to greater penetrating power. Absorbed dose is defined as the average energy of ionizing radiation absorbed per unit mass (dE/dm). To calculate dose deposition in tissue, the photons and secondary electrons, which result from the physical interactions, are traced voxel-by-voxel. Also, the probability of tissue ionization of each type of interaction $\tau/\rho$, $\kappa/\rho$, $\sigma/\rho$ sum, resulting in the mass energy absorption $[\mu/\rho]$.

The RBE can often be measured by cell survival experiments in-vitro or by biophysical models. Proton radiation has been shown to be more biologically effective for cell killing compared with X-rays for human tissue because of the higher density of ionization tracks. Clinically to date, RBE of 1.1 ($W_{RBE=1.1}$) is applied to all treatments independent of dose/fraction, position in the Spread Out Bragg Peak ("SOBP"), initial beam energy and the tissue type. However several studies reported that the RBE depends on the Dose-averaged Linear Energy Transfer ("$LET_d$"), cell or tissue type which is a function of its $(\alpha/\beta)_x$, and the dose per fraction. The variations of $LET_d$ values have been observed within the exposure volume in proton treatment. The RBE values are directly proportional to $LET_d$ and inversely proportional to $(\alpha/\beta)_x$. These dependencies make the RBE values vary from point to point along the proton track, especially where an SOBP is employed to treat the planning target volume ("PTV") region.

The increase in RBE of proton beams at the distal edge of the SOBP is a well-known phenomenon that is difficult to quantify accurately in vivo. For purposes of treatment planning, disallowing the distal SOBP to fall within vulnerable tissues hampers sparing to the extent possible with proton beam therapy ("PBT").

In treatment planning, any potential variation of RBE over the SOBP could result in biological hot spots with wide variations in biological dose that make dosimetry difficult.

Reviews of radiobiological data indicate that an RBE of 1.1-1.2 should be used to calculate the biological dose, $D_{bio}$, of proton radiation. However several studies suggest that the RBE is not a constant along the depth dose profile of the SOBP. The Bethe-Bloch equation describes an increase in stopping power as energy decreases. Therefore as depth of proton increases, the LET increases; and up to 100 keV/μm RBE increases.

Many published studies suggest that from the midpoint to the distal side of SOBP, the RBE value increases to a maximum of about 3. The RBE value increases from 1.1 at the absorber entrance to as much as 1.6 at the distal half of the SOBP plateau and to as much as 2.9 in the Distal Dose Fall-off ("DDF").

Thus, while in the art there is an understanding of the dose deposition physics of charged particle irradiation, there is an insufficient understanding of the biological responses to that energy absorption. Because biological response drives the clinical prognosis, the uncertainty needs to be resolved by using relative biological effectiveness in treatment planning for the application of radiation proton therapy.

The physics of proton therapy provides significant advantages over x-ray therapy in certain cases. For example children benefit from the increased conformity of dose delivery that minimizes dose to healthy tissue and reduces complications and the occurrence of secondary cancers. Proton therapy is also useful in cases of retreatment of recurrent tumors for similar reasons. Nonetheless, no therapy is both totally effective and without risk. As medicine strives toward this goal, the biological effects of each therapy must be understood and controlled. The treatment techniques used in the past will not be sufficient in the future.

SUMMARY

The present disclosure is directed toward a system for reducing biological damage caused by the application of proton beam therapy. More particularly, the present disclosure relates to a method of planning and treatment to reduce biological damage caused by the application of proton beam therapy.

Various systems for reducing biological hot spots in a beam therapy treatment comprising a processor in electrical communication with a tangible, non-transitory memory that, in response to an execution by the processor, cause the processor to measure a relative biological effectiveness of a beam on a region of a human body, and a beam applicator in electrical communication with the processor, wherein a characteristic of the beam can be adjusted based on the measured relative biological effectiveness are disclosed.

Also, various methods of treatment comprising measuring, by a processor capable of detecting potential biological hot spots, a relative biological effectiveness of a beam on a region of a human body, designing a beam therapy treatment plan based on the measured relative biological effectiveness, and applying a beam to a patient with a region in need of beam therapy with a beam applicator in electrical communication with the processor capable of detecting potential biological hot spots are also disclosed.

A changing RBE along the proton depth-dose distribution, with progressively higher RBE values near the distal part of spread out SOBP and in the DDF results in a different effective isodose distribution profile than is currently indicated using physical dose algorithms. In particular, the higher RBE value at the DDF will increase the biologically effective dose beyond the area of interest.

This disclosure includes proton RBE-weighted treatment plans in two-dimensions compared with standard proton plans using $W_{RBE=1.1}$. The isodose distribution profiles were accomplished using matrices that represent coplanar intersecting beams. These matrices were combined and contoured to clarify the distribution of dose using standard RBE or other various values of RBE ($W_{RBE=ref[25]}$).

There are some differences in dose distribution between the ($W_{RBE=1.1}$) and the modeled values of RBE ($W_{RBE=ref[25]}$). The hot spots of $W_{RBE=ref[25]}$ remain inside the PTV with higher RBE values. However increased dose also appeared outside of the PTV that may cause damage to healthy tissue in the body.

The depth dose distribution of a proton beam is useful to minimize the dose to healthy tissue and maximize the dose to tumor tissue, but it does not deliver a uniform dose to the tumor without modification. By superposition of several profiles with varying initial energies and thus ranges, a spread-out Bragg peak ("SOBP") can be used to cover the target volume with a homogeneous dose. The modification of the monoenergetic proton beam results in alteration of intensity as well energy distribution at any depth.

Furthermore, the addition of the superimposed profiles diminishes the sparing of the proximal healthy tissue. SOBP's are formed from overlapping pristine Bragg peaks resulting from a distribution of initial energy beams. Each distal fall-off of a monoenergetic proton beam has linear energy transfer (LET) ~60-100 keV/µm. The contribution from these high end-of-range LET protons would be expected to increase the relative biological effectiveness weighing factor ($W_{RBE}$) along the SOBP with the weighting increasing as the fractional contribution from the distal fall-off increases.

The Naïve dose shown in current commercial planning systems for PBT is based on physical dose (energy in metric Gray "Gy" units). Cells experience a biologic dose and the relationship is non-linear to actual physical energy. The present disclosure shows that there can be significant dose delivered outside of the PTV due to the extension of biological dose beyond the distal fall-off. This increase in biological dose beyond the PTV is dependent upon the angle between beams and the number of beams used to construct the distribution profile increasing the dose to healthy tissue between 20% to 40% greater than dose obtained using $W_{RBE=1.1}$.

The present disclosure, therefore, provides for correction of the naïve or physical dose for delivery of a dose with a safe relative biological effectiveness. Such a correction can be placed into planning systems to drive plan optimization algorithms. In one embodiment, an algorithm for isodose distribution profiles with RBE-weighted values along the proton modulation path is implemented using the MATLAB program and/or Excel.

One method presented by the present disclosure addresses a clinical problem inherent in charged particle therapy—the safe and effective management of the increasing RBE at the end of particle beams. The system and method of the present disclosure for avoiding damage caused by high RBE can be applied in any situation known in the art where there is an RBE increase at the end of a treatment beam being used.

Also provided by the disclosure is a technique referred to as "range modulation". With range modulation, distal falloff is smeared, reducing both the dose and average RBE over the terminal few millimeters of the SOBP.

Because of the increase in biological dose of proton radiation, particularly at the distal edge of the SOBP, the DDF should not be positioned within radiation sensitive tissues. Mitigation can be accomplished by slightly reducing the incident beam energy, which pulls the end-of-range back from the edge of the PTV, or by adjusting the number and configuration of the beams so as to avoid hot spots such as those observed in the case of 45° juxtaposed beams.

The distal fall-off can also be smeared out by feathering the delivery of the multi-fractional protocol. With this protocol, the initial energy of beams contributing to hotspots is varied over time to produce an averaging of the dose distribution at critical locations. This reduces both the dose and average RBE over the terminal few millimeters of the SOBP. Fortunately, uncertainties in patient setup and organ motion during treatment also contribute to this smearing effect and may be responsible for preventing the potential dire patient outcomes that might be predicted by the results presented herein.

An administrative mitigation technique might also be employed. In some embodiments, a clinic could impose a risk assessment and mitigation protocol that requires the development of at least two treatment plans for each patient: one using the standard of practice $W_{RBE=1.1}$, and one using a biologically driven worst case scenario set of $W_{RBE}$ values obtained from the literature. Beam configurations could then be displayed and evaluated, considering the potential for damage as indicated in Tables 8 and 9. Configurations deemed potentially dangerous could be discarded. Use of this technique allows evaluation of the clinical standard through visualization of biologically based treatment planning without risking implementation of an untested biological algorithm. The delivered treatment plan can reflect standard practices while being evaluated for potential risk.

Biological hot spots not apparent in treatment plans based on absorbed dose distribution may negatively impact patient outcomes in a variety of proton beam applications. Therefore, the embodiments of the present disclosure can apply to any heavy charged particle (for example carbon ions and protons). Some embodiments include tools and a process to improve patient safety via the visual display of biologic dose as an added feature to the planning process of patients getting particle therapy. RBE can be displayed graphically with the use of color to denote "biologic hot spots," or RBE can be displayed with ratios relative to a planned physical dose. The method can be used to become part of a goal algorithm of a treatment planning system in that beams can be modulated to make a plan's biology more homogeneous.

The disclosure also describes a novel technique to mitigate issues related to increased RBE at the distal edge of the SOBP by spoiling the distal falloff with existing patient specific device ("PSD") sets and beam angles. The technique is referred to as "range modulation" or "range mod". In one embodiment, this is accomplished by splitting the dose planned for a beam in half, shown in FIG. 3, and then delivering half the dose as planned and the other half of the dose with an identical beam whose range has been modified by 3 mm (3 mm is half the 6 mm spacing between pristine peaks in the SOBP for some beam delivery systems and comparable to the potential 1-2 mm increase in range due to RBE).

Thus, herein presented is a system for reducing biological hot spots in beam therapy treatment including a software-implemented program for measuring the relative biological effectiveness of one or more beams on one or more regions of a human body; and a beam applicator, wherein beam characteristics can be adjusted based on the measured relative biological effectiveness. In some embodiments, the beam therapy is at least one of a proton beam therapy or a carbon ion therapy. In other embodiments, the beam characteristic comprises at least one of a number of beams applied, a location of beam application, an initial energy intensity of a beam, an energy intensity of a beam over time, a beam's relative angles to a second beam, and a duration of a beam application.

In further embodiments, the program measures the relative biological effectiveness in real-time during application of beam therapy to a patient. In still further embodiments, the system further includes a visual display to display a real-time measure of the relative biological effectiveness. The visual display optionally can further include a visual comparison of the real-time measure of the relative biological effective dose and a currently prescribed physical dose. In other embodiments, one or more beam characteristics can be further adjusted to reduce a radiation dose delivered outside of one or more planning target volumes.

In alternative embodiments, the program adjusts a planning target volume based on the measure of the relative biological effectiveness. In further embodiments, one or more beam characteristics further can be adjusted to move one or more distal dose fall-off regions away from one or more radiation sensitive regions of a patient. Still in other embodiments, one or more beam characteristics further can be adjusted to smear one or more distal dose fall-off regions.

Additionally disclosed is a method of treatment with beam therapy including measuring the relative biological effectiveness of one or more beams on one or more regions of a human body; designing a beam therapy treatment plan based on the measure relative biological effectiveness; and applying one or more beams to a patient with one or more body regions in need of beam therapy, wherein the steps of measuring, designing, and applying may be performed by a processor using a software-implemented program which enable the processor to detect potential biological hot spots.

The method can further comprise modifying a beam therapy treatment plan based on physical radiation dose to account for the measured relative biological effectiveness. In some embodiments, the beam therapy comprises at least one of a proton beam therapy or a carbon ion therapy. In other embodiments, designing further includes modifying a beam characteristic comprising at least one of a number of beams applied, a location of beam application, an initial energy intensity of the beams, an energy intensity of a beam over time, a beam's relative angles to a second beam, and a duration of beam application.

Still in other embodiments, applying further includes modifying a beam characteristic comprising a number of beams applied, a location of beam application, an initial energy intensity of the beams, an energy intensity of the beams over time, a beam's relative angles to a second beam, and a duration of beam application. The method can further include measuring the relative biological effectiveness in real-time. In some embodiments, the method further includes displaying via a visual display a real-time measure of the relative biological effectiveness.

In some embodiments, the method further includes displaying a visual comparison of the real-time measure of the relative biological effective dose and a currently prescribed physical dose. Still in other embodiments, the method further includes adjusting one or more beam characteristics to reduce a radiation dose delivered outside of one or more planning target volumes. The method can further include adjusting a planning target volume based on the measure of the relative biological effectiveness. In some exemplary embodiments, the method includes adjusting one or more beam characteristics to move one or more distal dose fall-off regions away from one or more radiation sensitive regions of the patient. The method can further comprise adjusting one or more beam characteristics to smear one or more distal dose fall-off regions.

BRIEF DESCRIPTION OF THE DRAWINGS

The features of this disclosure, and the manner of attaining them, will become more apparent, and the disclosure itself will be better understood by reference to the following description of embodiments of the disclosure taken in conjunction with the accompanying drawings.

FIGS. 12A-12C shows an isodose distribution profile of two proton beams with 0° and 315° and incident energy of 87 MeV.

FIGS. 24A-23C show an isodose distribution profile of five proton beams with 0°, 180°, 225°, 270° and 315° and incident energy of 87 MeV.

FIGS. 26A-26C show an isodose distribution profile of five proton beams with 0°, 90°, 225°, 270° and 315° and incident energy of 87 MeV.

Figure 1:
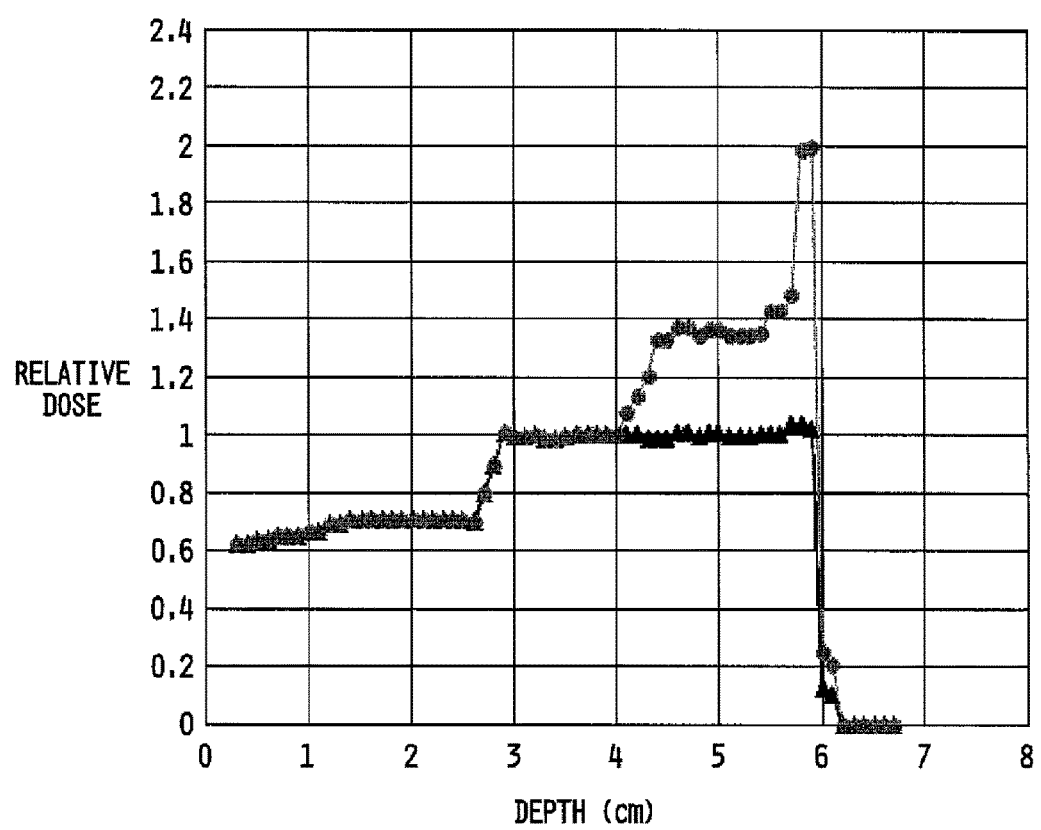
FIG. 1 shows a chart for the 4.6 cm SOBP depth dose profiles with $W_{RBE=1.1}$ (triangles) and $W_{RBE=ref[25]}$ (circles) for Hep2 cells in a proton beam of incident energy of 87 MeV.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DRAWINGS

The embodiments disclosed herein are not intended to be exhaustive or limit the disclosure to the precise form disclosed in the following detailed description. Rather, the embodiments are chosen and described so that others skilled in the art may utilize their teachings.

Referring first to FIG. 1, a chart for the 4.6 cm SOBP depth dose profiles with $W_{RBE=1.1}$ (triangles) and $W_{RBE=ref}$ [25] (circles) for Hep2 cells in a proton beam of incident energy of 87 MeV is shown. These data represent Hep2 human cells irradiated in a proton beam with initial energy of 87 MeV and 4.6 cm SOBP. Triangles show the assumed relative dose provided, and circles show the actual RBE.

Figure 2:
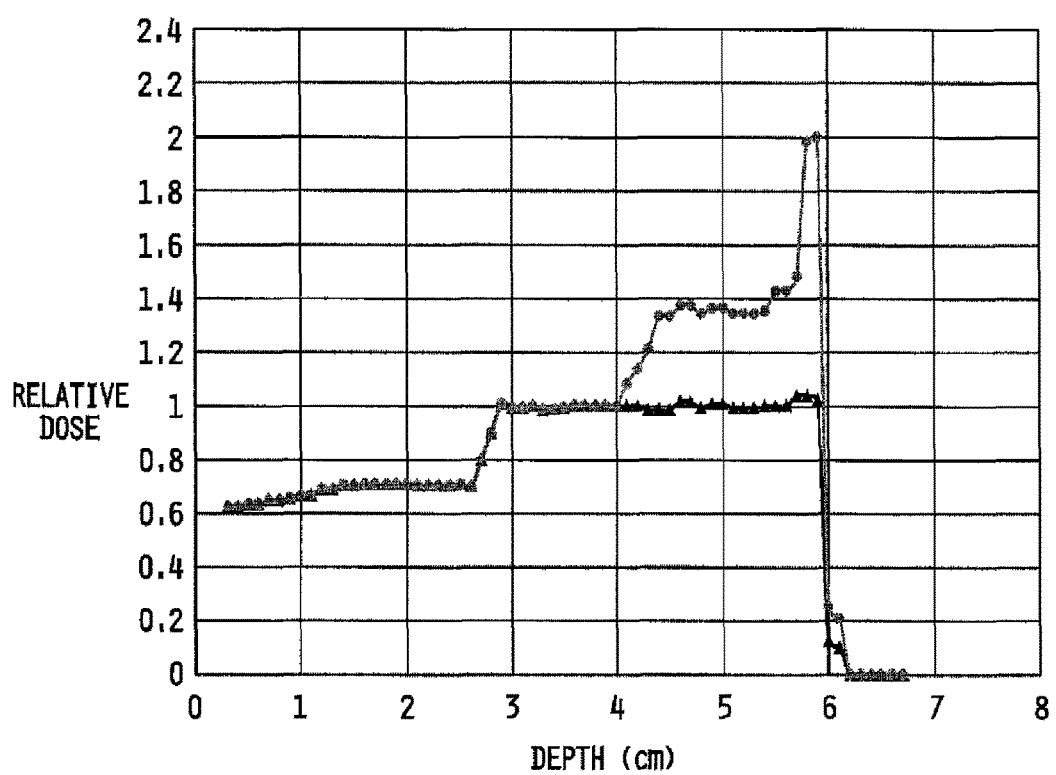
FIG. 2 shows a chart for the 3.0 cm SOBP depth dose profiles with $W_{RBE=1.1}$ (triangles) and $W_{RBE=ref[25]}$ (circles) for Hep2 cells in a proton beam of incident energy of 87 MeV.

Referring now to FIG. 2, a chart for the 3.0 cm SOBP depth dose profiles with $W_{RBE=1.1}$ (triangles) and $W_{RBE=ref}$ [25] (circles) for Hep2 cells in a proton beam of incident energy of 87 MeV is shown. These data represent Hep2 human cells irradiated in a proton beam with initial energy of 87 MeV and 3.0 cm SOBP. Triangles show the assumed relative dose provided, and circles show the actual RBE.

Figure 3:
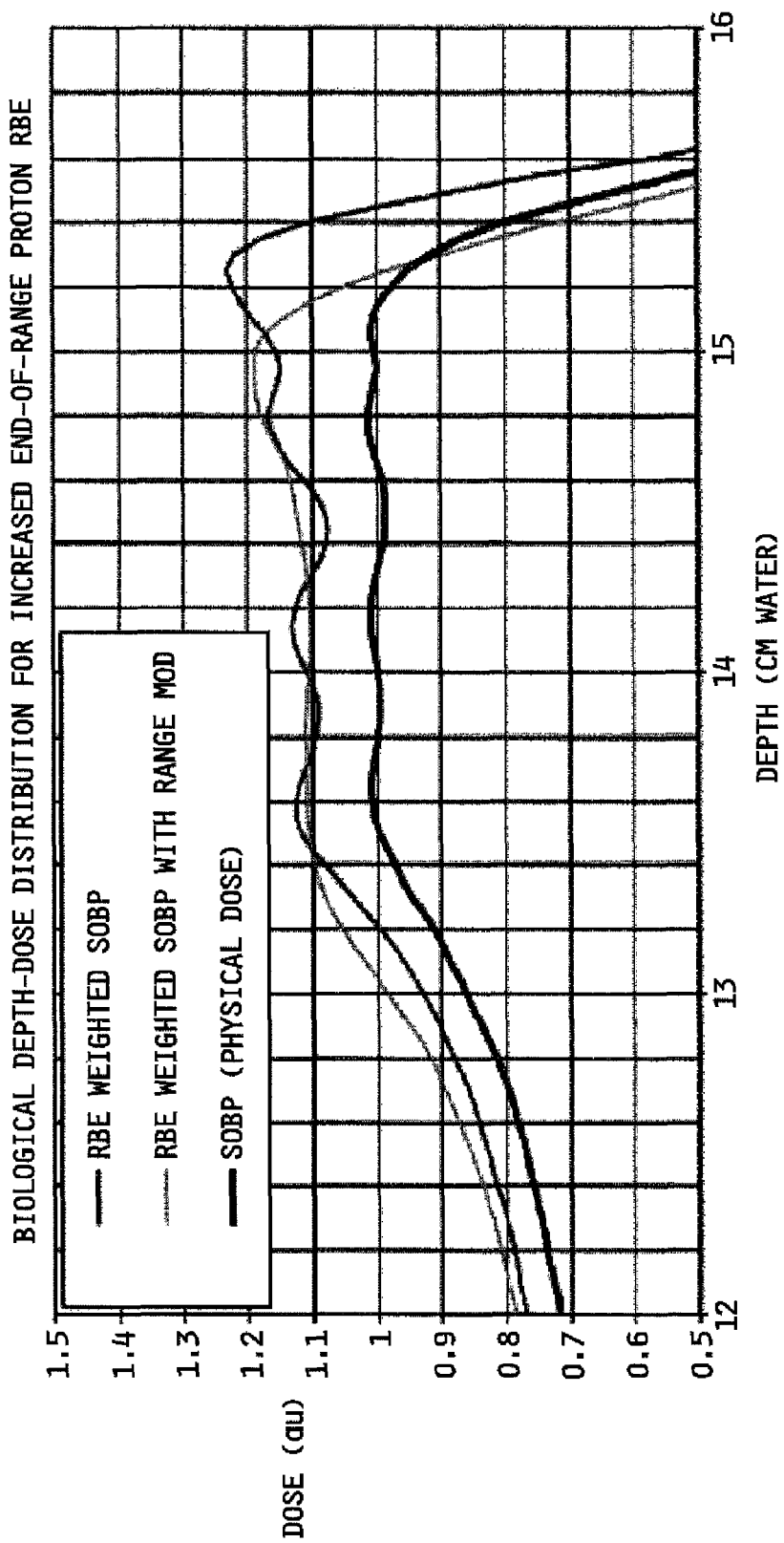
FIG. 3 shows a chart for the physical dose for a SOBP composed of four pristine Bragg peaks each separated by 6 mm water equivalent.

Referring now to FIG. 3, a chart for the physical dose for a SOBP composed of four pristine Bragg peaks each separated by 6 mm water equivalent is shown. FIG. 3 shows the application of an illustrative model of increased distal RBE to the individual pristine peaks, which produces the RBE weighted SOBP. The "range mod" technique mitigates the changes in SOBP plateau flatness, range, and effective dose at the distal edge. The modulation is achieved by splitting the SOBP into two parts and shifting one beam by 3 mm to both smooth out the SOBP and decrease the RBE at the end of the beam. Therefore, in one embodiment, the technique is delivering half the dose as planned by one beam, and the other half of the dose is delivered with an identical beam whose range has been modified by 3 mm (3 mm is half the 6 mm spacing between pristine peaks in the SOBP for the beam delivery system and comparable to the potential 1-2 mm increase in range due to RBE).

Figure 4:
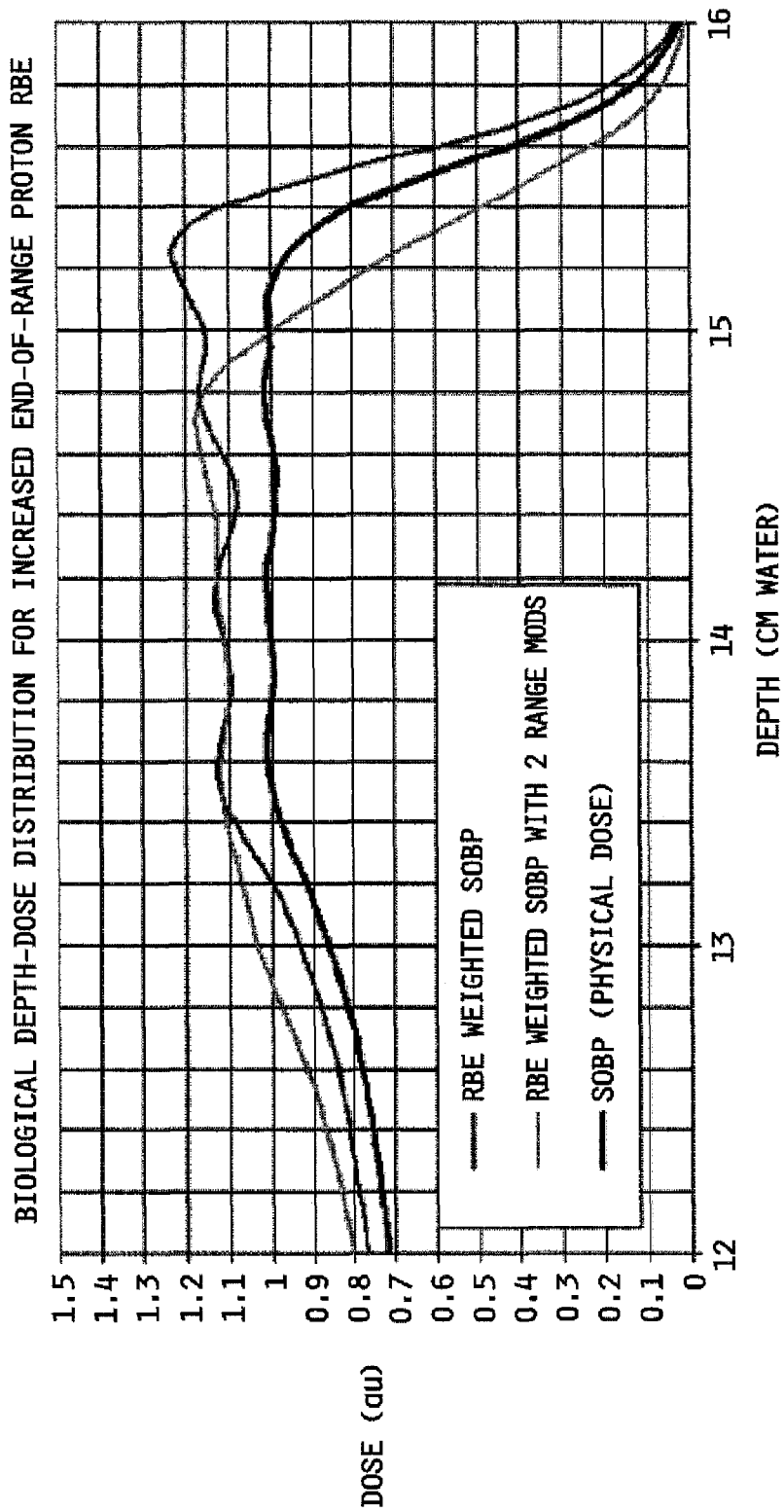
FIG. 4 shows a chart for splitting the SOBP into three beams so as to further reduce the RBE effect.

Now referring to FIG. 4, a chart for splitting the SOBP into three beams so as to further reduce the RBE effect is shown. In some embodiments, splitting the SOBP into multiple beams (three beams in the embodiment show) is done when a single beam plan is being used such as with a posterior fossa boost or germinoma boost after whole ventricular radiation is employed. Splitting the SOBP beam plan can be employed at other times as well when there is significant clinical concern regarding a specific organ at risk ("OAR"). As shown by FIG. 4, if a single beam is being used for a plan to a significant dose, three beams can be used and the range is modified by 2 mm for each beam making the two beam range changes 2 mm and 4 mm.

Figure 5:
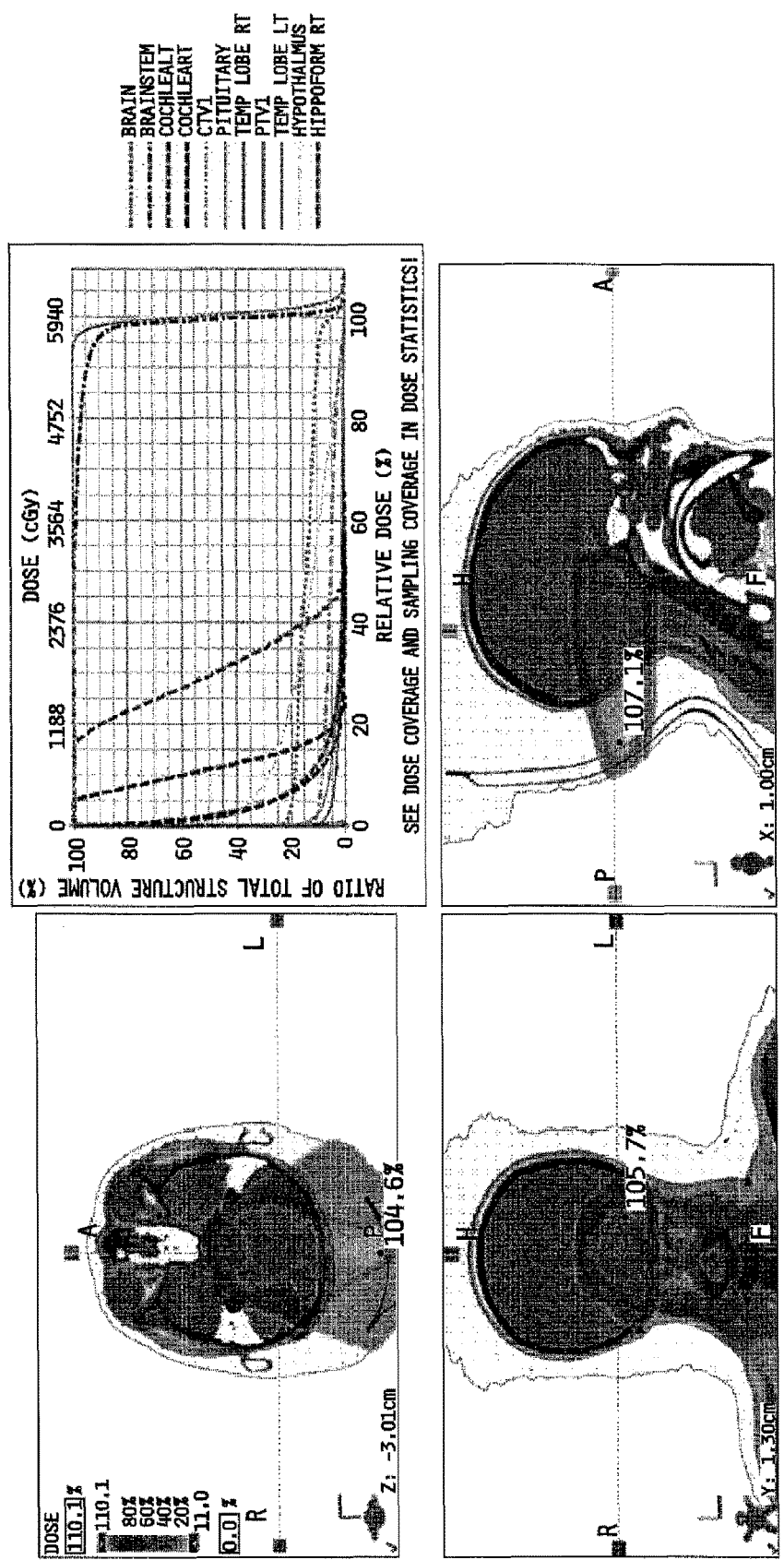
FIG. 5 shows a proton beam treatment plan using non-range modulation proton beam therapy ("NRMPBT").
Figure 6:
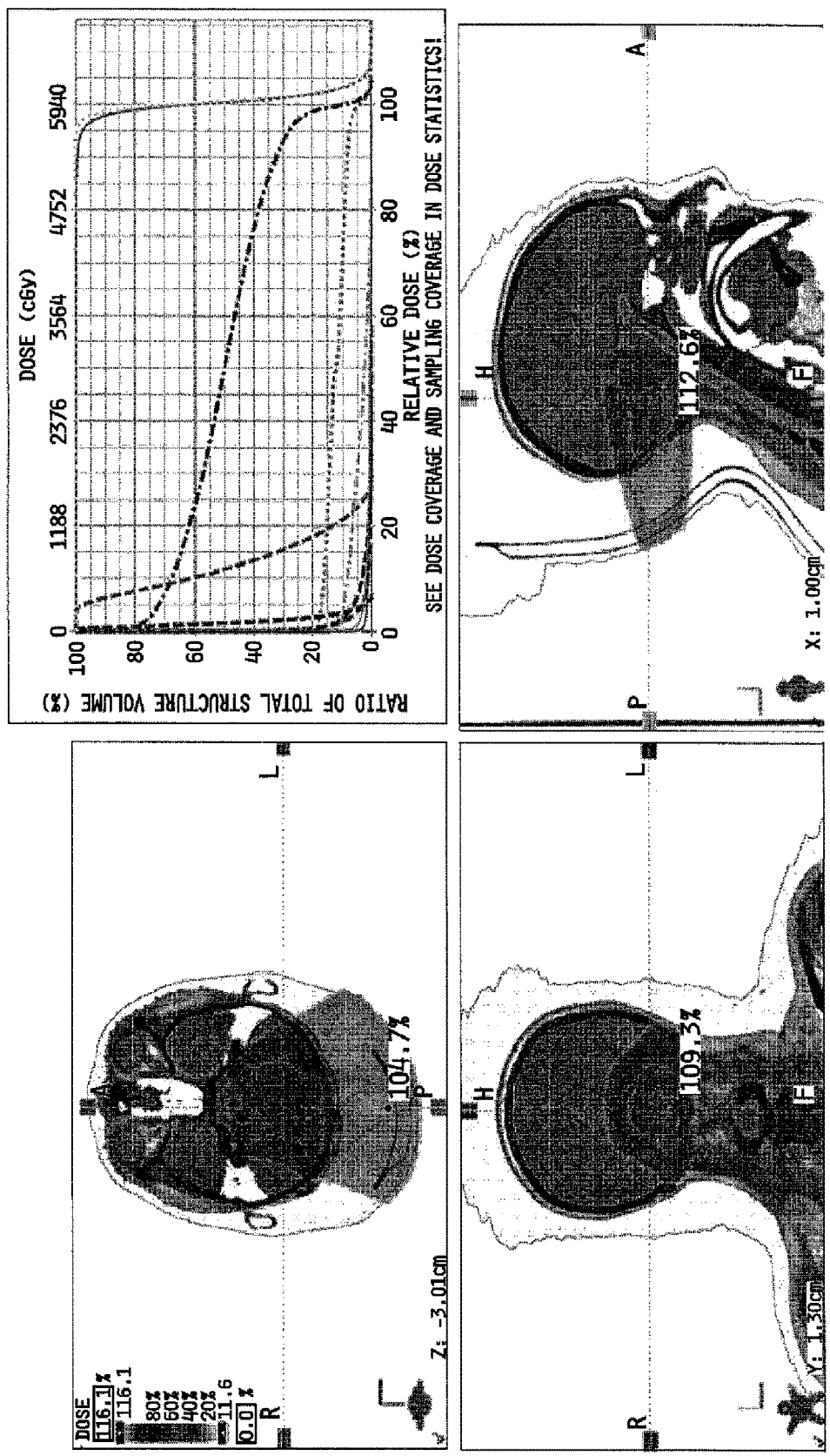
FIG. 6 shows a proton beam treatment plan using range-modulation proton beam therapy ("RMPBT") as the primary treatment.
Figure 7:
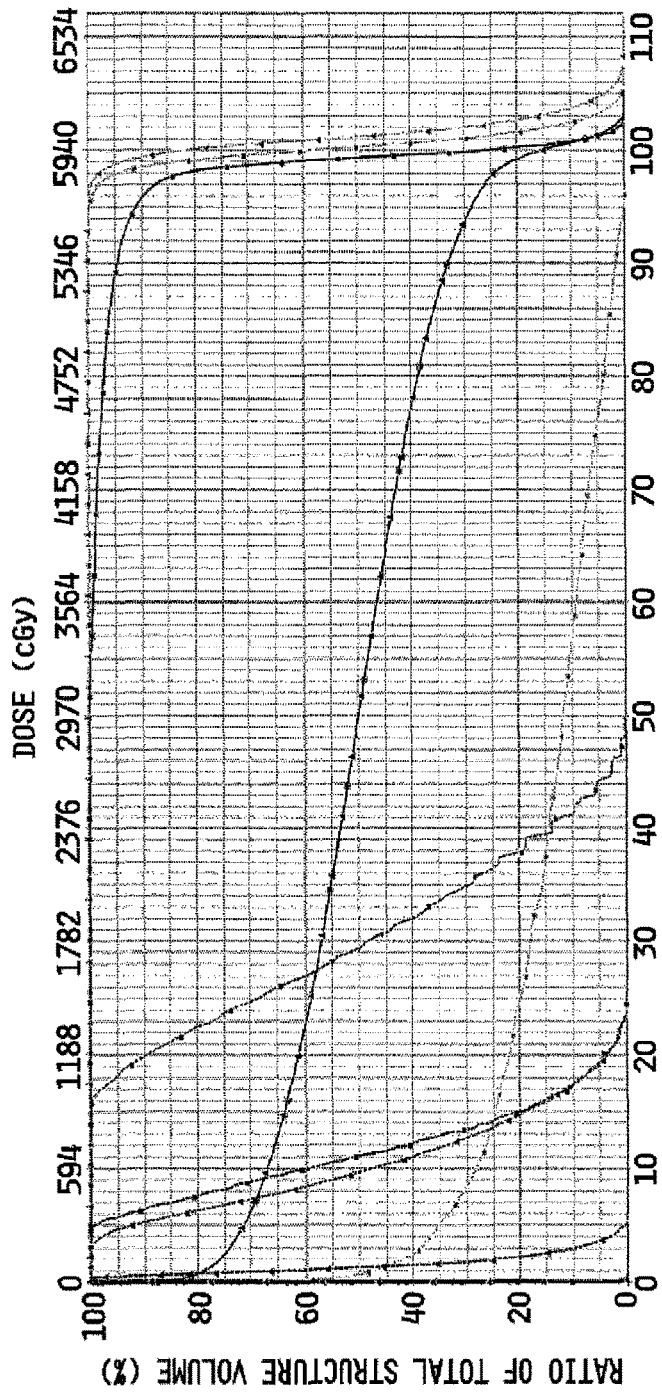
FIG. 7 shows a comparison of the dose-volume histograms ("DVH's") for several OAR's between the NRMPBT and the RMPBT plans shown in FIGS. 5 and 6, respectively.
Figure 8:
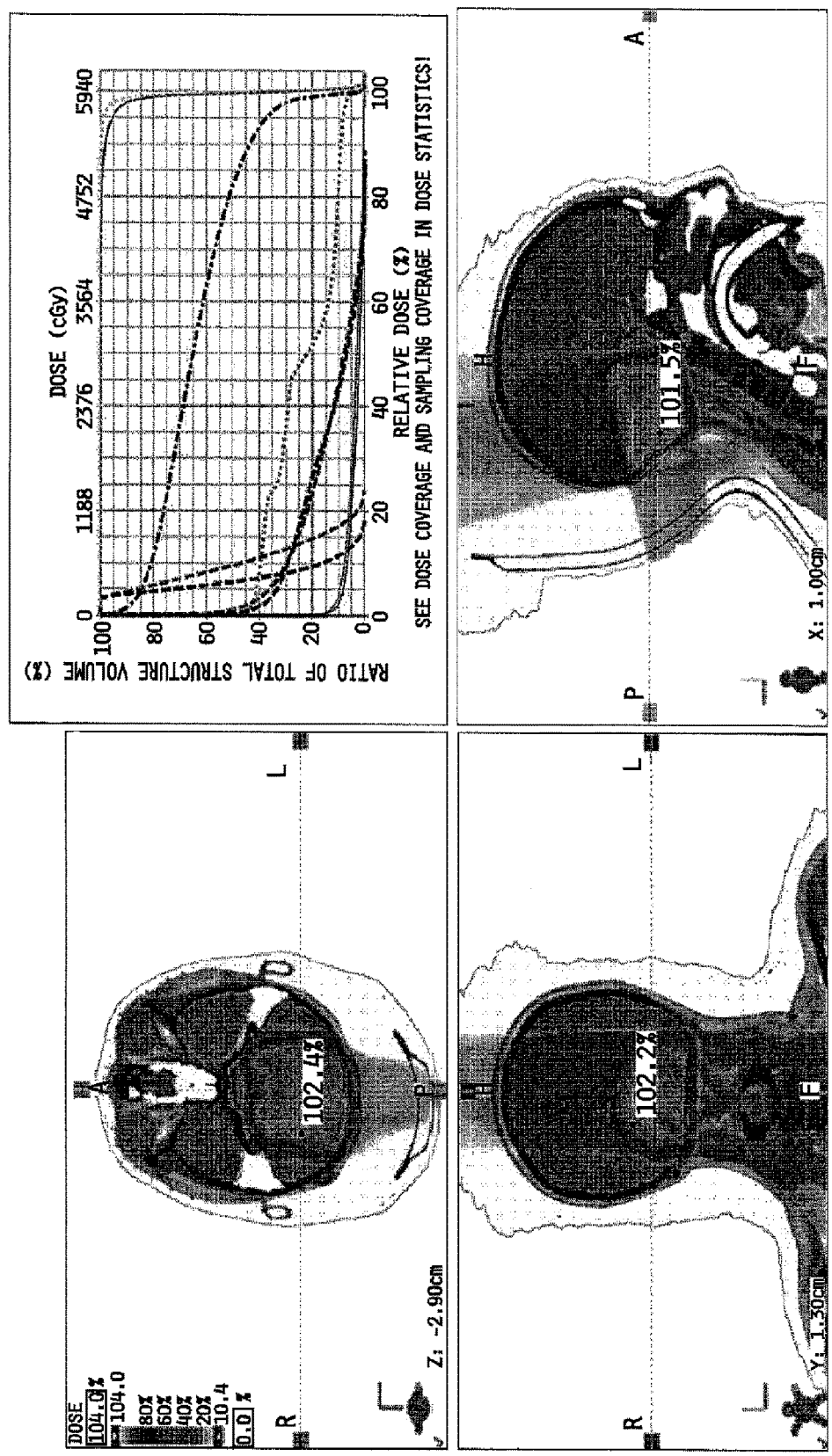
FIG. 8 shows the actual treatment plan delivered using range-modulation proton beam therapy retreatment scenario ("RMPBTrt").

Now referring to FIGS. 5-8, multiple beam plans generated as primary treatment for a patient are shown. FIG. 5 shows a proton beam treatment plan using non-range modulation proton beam therapy ("NRMPBT"). FIG. 6 shows a treatment proton beam treatment plan using range-modulation proton beam therapy ("RMPBT") as the primary treatment. The dose-volume histogram ("DVH") colors are the same as used in FIG. 5. FIG. 7 shows a comparison of the DVH's for several OAR's between the NRMPBT and the RMPBT plans shown in FIGS. 5 and 6, respectively. In every case, the RMPBT plan treats less volume of the OAR's shown. FIG. 8 shows the actual treatment plan delivered using range-modulation proton beam therapy retreatment scenario ("RMPBTrt"). Vertex beams can be used to minimize dose summation with the prior coplanar IMRT plan, as the patient received. DVH colors are the same as used in FIG. 5.

In the embodiment shown, organs at risk, ("OAR's") are spared unnecessary dose. In one exemplary embodiment, the proton beam was assumed to have a uniform RBE of 1.1 and the excess RBE was modelled analytically with a hyperbolic tangent centered on the point of maximum dose of the pristine Bragg peak and saturating at 35% with a characteristic length of 2 mm. Applying this model to the individual pristine peaks comprising the delivery of a SOBP allowed illustration of the changes in plateau flatness, range, and biological effectiveness—a "range mod" mitigates all three of these effects. With this method, both PSD number and patient set up time can be decreased.

The RMPBTrt varies from the optimal RMPBT plan in that a vertex field is used so as to pull dose off the skin and minimize the volume of retreated tissue outside of the PTV. Tables 1 and 2 below outline the dosimetric comparison of the plans. All planning modalities produced plans that cover the PTV. The RMPBT method treats less total brain than the NRMPBT method given the fact that the beams are not extended to cover the entirety of the brainstem in an effort to avoid ending the beam in the brainstem. When looking at the OAR doses, the difference in plans is pronounced due to this difference.

Data exist that suggest doses over 10 Gy are sufficient to ultimately cause hypothalamic dysfunction. In the NRM-PBT plan, the average dose is lower, but the peak dose posteriorly is close to the full prescription dose due to the goal of treating through the full brainstem. Only in the RMPBT plan is hypothalamic dose absent completely. This trend continues for the doses to left and right cochleae, the temporal lobes, the pituitary, and the brainstem itself. These data are summarized in Tables 1 and 2.

As a formal retreatment plan, behind the numbers in the RMPBTrt plan is the concept of treating the previously treated tissue to the lowest sum doses possible. In some embodiments, this can be achieved by minimizing dose overlap issues between a prior co-planar photon plan and the current retreatment proton plan via vertex beam usage. The through brainstem approach, or NRMPBT plan, had a vertex field been employed, treats a much larger volume of hippocampus and temporal lobe, making its use problematic in the retreatment context.

Even with the RMPBTrt plan's beam arrangement used to minimize overlap with prior dose, very significant dosimetric saving can be achieved for the cochleae, the hypothalamus, and the brainstem relative to the NRMPBT plan. The hippocampal dose, despite the vertex field, remained well below the mean dose seen by the other methods. One advantage of RMPBT is one of significantly increased patient safety by the direct reduction of treated tissue in a fashion otherwise impossible even for traditional proton therapy, because it allows the safe termination of a proton beam or set of beams in an OAR.

In some embodiments, the RMPBT technique can be adapted to use in pencil beam planning as well and may prove to be even more critical in that arena as beam edge dosimetry will likely need to become modulated as well. In each case, the number of PSD sets used was decreased or kept the same. Time in the room and complexity can be decreased in range modulated patient scenarios relative to electing another angle from which to treat. In other embodiments, range modulation can be simple to deliver in the treatment rooms. As a result of fewer net patient positions being used, fewer verification films are needed and patient exposure to radiation can be decreased.

There are at least four advantages to range modulation, or smearing of the distal range of a proton beam, compared to traditional multiple beam proton therapy. First, better tissue sparing is achieved via a more aggressive use of distal blocking. Second, time-savings in the treatment room can be achieved as fewer beam angles are needed. This could allow the avoidance of anesthesia in some cases. It also decreases the need to wait for the physicians required to review position films (every field is reviewed every day in some centers prior to beam delivery), improving throughput.

Third, less image guidance imaging might be used, as only the first of a range modified series of beams might require image guidance (orthogonal image verification). Fourth, no new PSD sets have to be manufactured which saves time for the machine shop construction and the cost of the materials and labor involved.

Beam angle variation also can be quite valuable to make plans more robust as target and other tissue volumes change during treatment. This is important in anatomical regions containing tissue/air/bone such as the sinuses and hilar regions. Some embodiments of the present disclosure provide a way of employing the primary principle of radiation safety of "as low as reasonably achievable," more commonly known by the acronym "ALARA," in treatment. It is cost-effective because no new PSD sets need to be constructed and the patient beam angle does not change in the room taking time and requiring set-up imaging for position verification.

The method presented by the present disclosure is extendible and translatable to spinal cord cases, craniopharyngiomas, optic pathway tumors, base of skull tumors, and pelvic tumors. Without being limited to one explanation, it is believed the method succeeds by moderately smearing out the sharpness of the end of the SOBP. This modest compromise allows safe stoppage of proton beams within critical structures such as the brainstem as shown. Those of ordinary skill in the art, such as treating physicians, can balance the need for safety against distal blocking goals regarding whether a biologic hot spot in an OAR in a given plan is acceptable.

Tables 1 and 2 show the dosimetric comparison of three plans, (1) NRMPBT, (2) RMPBT, and (3) RMPBTrt.

TABLE 1

Dosimetric comparison of three plans.

|  |  | CTV | PTV | Brain-stem | Left cochlea | Right cochlea | Left temporal lobe |
|---|---|---|---|---|---|---|---|
| NRMPBT | Min | 90.1 | 88.7 | 29.4 | 15.4 | 4.7 | 0 |
|  | Max | 108.1 | 109.4 | 103.6 | 49.9 | 25.6 | 102.8 |
|  | Mean | 100.4 | 100.1 | 97.9 | 30.2 | 11.6 | 2.2 |
| RMPBT | Min | 79.9 | 63.2 | 0 | 3.9 | 0 | 0 |
|  | Max | 110.1 | 110.1 | 105.8 | 29.2 | 7.4 | 97.9 |
|  | Mean | 100.7 | 100.3 | 50.1 | 12.9 | 1.9 | 0.9 |
| RMPBTrt | Min | 55.5 | 45.6 | 0 | 8.1 | 4.4 | 0 |
|  | Max | 100 | 100 | 96.7 | 27.7 | 15.2 | 94.8 |
|  | Mean | 94.5 | 93.6 | 42.4 | 16.9 | 8.2 | 4.3 |

All numbers are in percentage of prescription dose. The prescription dose for this case was 59.4 Gy.

TABLE 2

Dosimetric comparison of three plans, continued.

|  |  | Right temporal lobe | Hypo-thal-amus | Pitu-itary | Left hippo-campus | Right hippo-campus | Brain |
|---|---|---|---|---|---|---|---|
| NRMPBT | Min | 0 | 0 | 0 | 0 | 0 | 0 |
|  | Max | 100 | 96.7 | 1.2 | 65.8 | 57.8 | 108.5 |
|  | Mean | 1.5 | 13.8 | 0.2 | 4.4 | 4.1 | 14.4 |
| RMPBT | Min | 0 | 0 | 0 | 0 | 0 | 0 |
|  | Max | 99.1 | 0 | 0 | 58.8 | 46.6 | 110.1 |
|  | Mean | 0.6 | 0 | 0 | 0.8 | 1.1 | 12.4 |
| RMPBTrt | Min | 0 | 0 | 0 | 0 | 0 | 0 |
|  | Max | 92.5 | 0 | 0 | 81 | 70.3 | 100 |
|  | Mean | 2.6 | 0 | 0 | 11.5 | 8.7 | 20.7 |

Table 3 summarizes present clinical uses and general guidelines for certain embodiments of RMPBT. RMPBT represents treatment planning that reflects not only thinking in terms of traditional energy dose (Gy) but also in terms of biologic dose (RBE).

TABLE 3

Clinically employed informal range modulation guidelines.

| Clinical situation | Approach used | Example |
|---|---|---|
| Single beam being employed for more than a few fractions. | Three ranges rather than two are used. | 1. Full posterior fossa boost with full cochlear sparing. 2. Boost for germinoma after whole ventricular radiation often via a posterior beam. |
| Three or more main angles are being used and the patient is awake meaing six possible fields may need to be delivered. | One of two ranges for each beam angle is treated per day with care to avoid coincidental beam ends. Ranges alternate each day. | 1. Brain tumors. 2. Pelvic tumors. 3. Spine tumors in some cases. Base of skull tumors. |
| The patient has had prior radiation. | We will sometimes use three ranges rather than two when super critical structures are involved. | 1. Ependymoma retreatment with the brainstem. 2. Salvage glioma cases with beams ending in eloquent brain. 3. Retreatment patients with a distant history of radiation necrosis with new cancer in similar locations. |
| Two or more beams end in the same point or points. | Beams are split into range mod pairs and care is used to look at each end point set for each day to avoid overlaps. | 1. Fourth ventricular ependymoma. 2. Vertex beams use can hide this issue and great care is used in plan review to look for "in corner" doses. |

Figure 9:
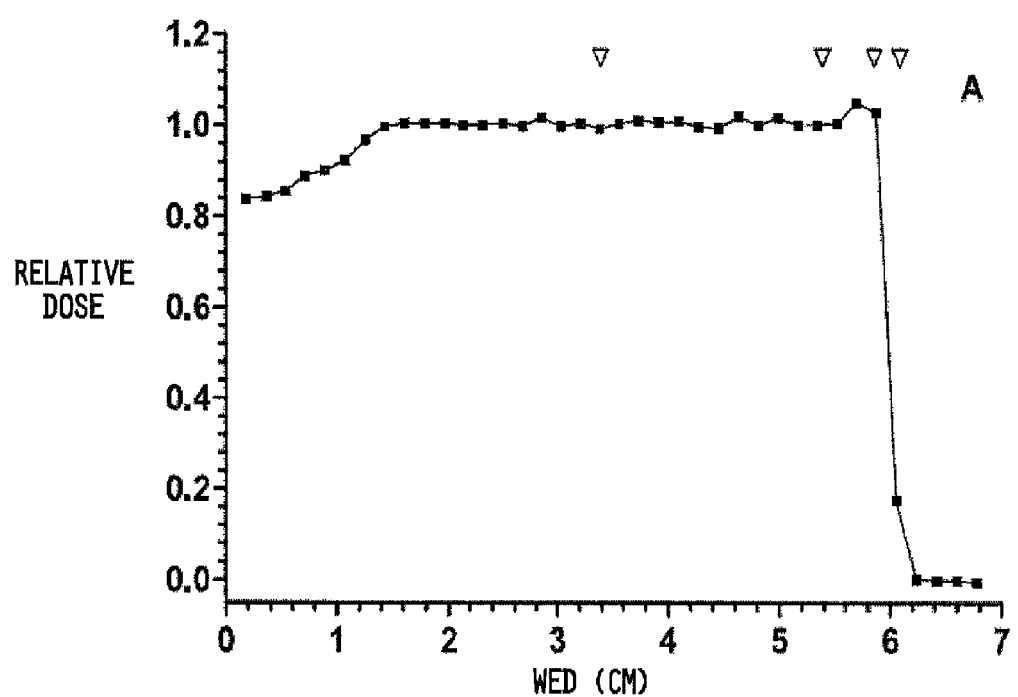
FIG. 9 shows the physical dose profile of a 4.6 cm SOBP with incident energy of 87 MeV.
Figure 10:
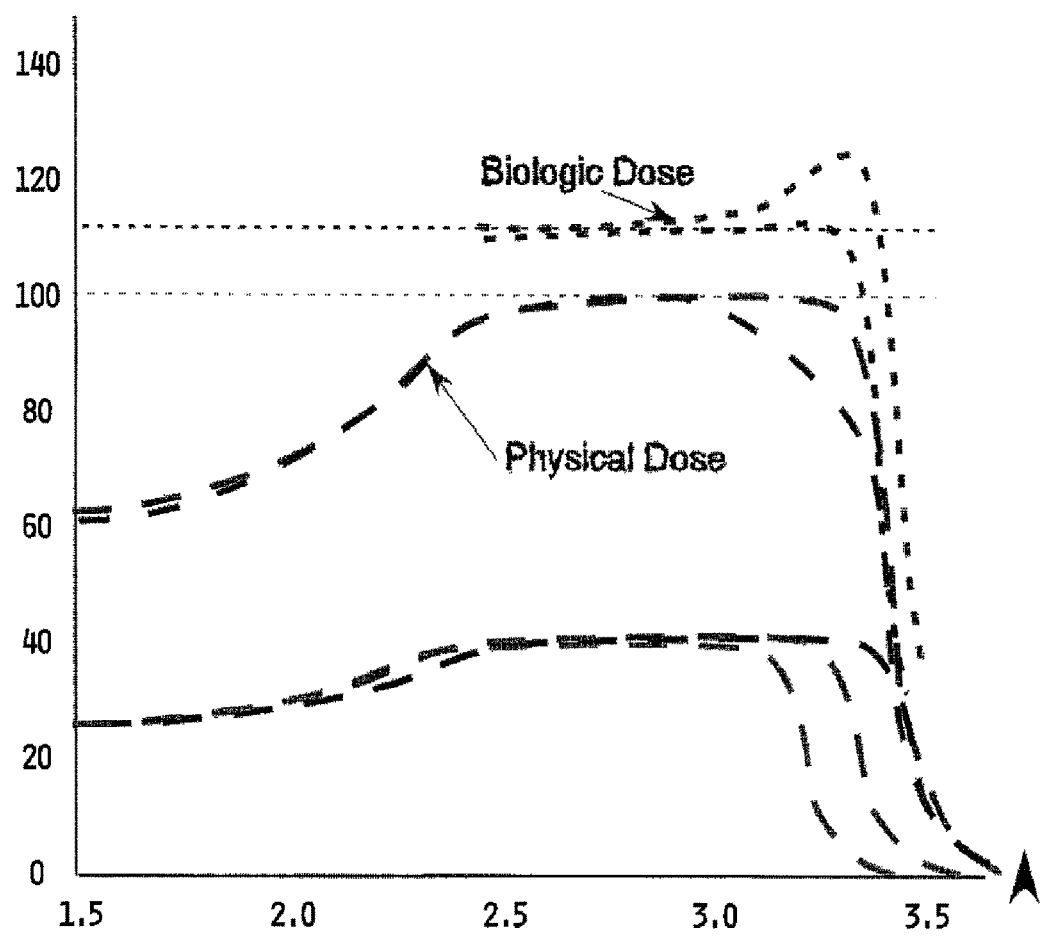
FIG. 10 shows a comparison between the biologic dose and physical dose in one embodiment of proton beat therapy.

Referring now to FIG. 9, the physical dose profile of a 4.6 cm SOBP with incident energy of 87 MeV is shown. Certain Excel and MATLAB programs were used to describe the isodose distribution of the 87 MeV proton beam with $W_{RBE=1.1}$ and $W_{RBE=ref[25]}$ and compare between them. The target is assumed to be 30 mm in diameter. Measurements of depth-dose profile taken at Indiana University Health Proton Therapy Center (IUHPTC) by Britten et. al are applicable to the embodiment shown. Britten et al. determined the relationship between the RBE and the dose-averaged linear energy transfer (LETd) of the proton beam track at various positions along the depth-dose profile SOBP. Tumor cell clonogenic assays were performed at 33.9 mm, 53.9 mm, 58.6 mm, and 60.9 mm along the 4.6 cm SOBP of beam with incident energy of 87 MeV as shown in FIG. 3.1. The error in absolute dose measurement was estimated to be (±3%) at the middle of SOBP and the relative error in dose at the distal region was estimated to be (±2%). The data of FIG. 9 are translated into tabular format below (Table 4).

TABLE 4

4.6 cm SOBP physical relative dose profile with $W_{RBE=1.1}$ (Relative $D_{RBE=1.1}$) and incident energy of 87 MeV.

| Depth(cm) | Relative $D_{RBE=1.1}$ |
|---|---|
| 0 | 0.8 |
| 0.1 | 0.83190184 |
| 0.2 | 0.83190184 |
| 0.3 | 0.839263804 |
| 0.4 | 0.839263804 |
| 0.5 | 0.85398773 |
| 0.6 | 0.85398773 |
| 0.7 | 0.883435583 |
| 0.8 | 0.883435583 |
| 0.9 | 0.898159509 |
| 1 | 0.920245399 |
| 1.1 | 0.920245399 |
| 1.2 | 0.964417178 |
| 1.3 | 0.964417178 |
| 1.4 | 0.993865031 |
| 1.5 | 0.993865031 |
| 1.6 | 1.001226994 |
| 1.7 | 1.001226994 |
| 1.8 | 1.001226994 |
| 1.9 | 1.001226994 |
| 2 | 1.001226994 |
| 2.1 | 0.993865031 |
| 2.2 | 0.993865031 |
| 2.3 | 0.993865031 |
| 2.4 | 0.993865031 |
| 2.5 | 1.001226994 |
| 2.6 | 0.993865031 |
| 2.7 | 0.993865031 |
| 2.8 | 1.008588957 |
| 2.9 | 1.008588957 |
| 3 | 0.993865031 |
| 3.1 | 0.993865031 |
| 3.2 | 1.001226994 |

TABLE 4-continued 4.6 cm SOBP physical relative dose profile with $W_{RBE=1.1}$ (Relative $D_{RBE=1.1}$) and incident energy of 87 MeV.

| Depth(cm) | Relative $D_{RBE-1.1}$ |
|---|---|
| 3.3 | 0.986503067 |
| 3.4 | 0.989 |
| 3.5 | 0.993865031 |
| 3.6 | 1.001226994 |
| 3.7 | 1.001226994 |
| 3.8 | 1.001226994 |
| 3.9 | 1.001226994 |
| 4 | 1.001226994 |
| 4.1 | 1.001226994 |
| 4.2 | 1.001226994 |
| 4.3 | 0.986503067 |
| 4.4 | 0.986503067 |
| 4.5 | 0.986503067 |
| 4.6 | 1.01595092 |
| 4.7 | 1.01595092 |
| 4.8 | 0.993865031 |
| 4.9 | 1.008588957 |
| 5 | 1.008588957 |
| 5.1 | 0.993865031 |
| 5.2 | 0.993865031 |
| 5.3 | 0.993865031 |
| 5.4 | 0.9999 |
| 5.5 | 1.001226994 |
| 5.6 | 1.001226994 |
| 5.7 | 1.03803681 |
| 5.8 | 1.038 |
| 5.9 | 1.023312883 |
| 6 | 0.125153374 |
| 6.1 | 0.1 |
| 6.2 | 0 |
| 6.3 | 0 |
| 6.4 | 0 |
| 6.5 | 0 |
| 6.6 | 0 |
| 6.7 | 0 |
| 6.8 | 0 |

The results of Britten et al. used to model the positional RBE at locations noted in FIG. 9 are shown in Table 5.

TABLE 5

The measurements of RBE at the position of water equivalent depth ("WED") with incident energy of 87 MeV 4.6 cm SOBP for Hep2 cells.

| Incident energy (MeV) | WED (mm) | RBE |
|---|---|---|
| 87 | 33.9 | 1.46 |
| 87 | 53.9 | 1.57 |
| 87 | 58.9 | 2.1 |
| 87 | 60.9 | 2.3 |

Different biological effects, such as cell killing, tissue damage or mutation can result from different kinds of radiation even if the physical doses are equal. This difference of biological effects reflects the pattern of energy deposition and biological metabolism at the microscopic level. RBE can be defined as the empirical value of a reference radiation that produces a given biological effect to the a empirical value of a test radiation that is produced by the given radiation isodose, for example equation 1.

$$RBE = \frac{\text{Reference radiation dose required to preduced effect } X}{\text{Test radiation dose required to produce effect } X} \quad (1)$$

Because the clinical experience is based on photon radiotherapy, Co γ-rays or 250-kVp x-rays are used for the reference radiation, in general. RBE reflects radiobiological sensitivities as well as physical attributes. For example, the $(\alpha/\beta)$ for tumors is approximately 10 while the $(\alpha/\beta)$ for late responding normal tissue is approximately 3. Microenvironments within the tissue such as degree of vascularization may also have significant bearing on radiation sensitivity. The physical attributes affecting RBE that concern this work include LET and track structure, radiation dose, and delivery schema. In general, an RBE increase is related to an increased ionization density, producing more lethal DNA damage.

To obtain the equivalent biological dose ($D_{bio}$) from the prescribed physical dose($D_{phys}$), the following relationship is used:

$$D_{bio} RBE \times D_{phys} \quad (2a)$$

To re-calculate the dose to include RBE using Equation 2a, the following relationship may be deduced:

$$D_{RBE}(RBE = ref[25]) = \frac{D_{RBE}\left(RBE = 1.1, \frac{\alpha}{\beta} = 3.76\right)}{1.1} \times W_{RBE=ref[25]} \quad (2b)$$

where $D_{RBE}$(RBE=ref [25]) is the dose with variable values of RBE, $W_{RBE=ref[25]}$ is the variable values of RBE and $$D_{RBE}\left(RBE = 1.1, \frac{\alpha}{\beta} = 3.76\right)$$

is the dose with general value of RBE since $\alpha=0.143$ Gy$^{-1}$ and $\beta=0.038$Gy$^{-2}$. Table 5 was used in one embodiment because Hep2 cells represent the human cells and the RBE of these cells may be useful for tumor treatment. Equation 2b is applied to the dose depth profile with $W_{RBE=ref[25]}$ along SOBP of incident energy of 87 MeV for Hep2 human cells and calculated in tabular format below (Table 6). Table 6 is important to establish the matrices of the proton beam.

TABLE 6

4.6 cm SOBP physical relative dose profile with $W_{RBE=ref[25]}$ (Relative $D_{RBE=ref[25]}$) and incident energy of 87 MeV for the Hep2 Human cells.

| Depth(cm) | Relative $D_{RBE=ref[25]}$ |
|---|---|
| 0 | 0.8 |
| 0.1 | 0.83190184 |
| 0.2 | 0.83190184 |
| 0.3 | 0.839263804 |
| 0.4 | 0.839263804 |
| 0.5 | 0.85398773 |
| 0.6 | 0.85398773 |
| 0.7 | 0.883435583 |
| 0.8 | 0.883435583 |
| 0.9 | 0.898159509 |
| 1 | 0.920245399 |
| 1.1 | 0.920245399 |
| 1.2 | 0.964417178 |
| 1.3 | 0.964417178 |
| 1.4 | 0.993865031 |
| 1.5 | 0.993865031 |
| 1.6 | 1.001226994 |
| 1.7 | 1.001226994 |
| 1.8 | 1.001226994 |
| 1.9 | 1.001226994 |

TABLE 6-continued 4.6 cm SOBP physical relative dose profile with
$W_{RBE-ref[25]}$ (Relative $D_{RBE-ref[25]}$)
and incident energy of 87 MeV for the Hep2 Human cells.

| Depth(cm) | Relative $D_{RBE-ref[25]}$ |
|---|---|
| 2 | 1.001226994 |
| 2.1 | 0.993865031 |
| 2.2 | 0.993865031 |
| 2.3 | 0.993865031 |
| 2.4 | 0.993865031 |
| 2.5 | 1.001226994 |
| 2.6 | 0.993865031 |
| 2.7 | 0.993865031 |
| 2.8 | 1.008588957 |
| 2.9 | 1.008588957 |
| 3 | 0.993865031 |
| 3.1 | 0.993865031 |
| 3.2 | 1.001226994 |
| 3.3 | 1.067216955 |
| 3.4 | 1.312672727 |
| 3.5 | 1.31912995 |
| 3.6 | 1.328901283 |
| 3.7 | 1.328901283 |
| 3.8 | 1.328901283 |
| 3.9 | 1.328901283 |
| 4 | 1.328901283 |
| 4.1 | 1.328901283 |
| 4.2 | 1.328901283 |
| 4.3 | 1.309358617 |
| 4.4 | 1.309358617 |
| 4.5 | 1.309358617 |
| 4.6 | 1.348443949 |
| 4.7 | 1.348443949 |
| 4.8 | 1.355270496 |
| 4.9 | 1.393686559 |
| 5 | 1.393686559 |
| 5.1 | 1.391411043 |
| 5.2 | 1.391411043 |
| 5.3 | 1.409481316 |
| 5.4 | 1.42713 |
| 5.5 | 1.456330173 |
| 5.6 | 1.456330173 |
| 5.7 | 1.698605689 |
| 5.8 | 1.981636364 |
| 5.9 | 2.000111545 |
| 6 | 0.255995538 |
| 6.1 | 0.209090909 |
| 6.2 | 0 |
| 6.3 | 0 |
| 6.4 | 0 |
| 6.5 | 0 |
| 6.6 | 0 |
| 6.7 | 0 |
| 6.8 | 0 |

FIG. 1 shows comparison of the depth dose profiles originated from relative $D_{RBE=1.1}$ derived in Table 4 using the standard RBE ($W_{RBE=1.1}$) and the $D_{RBE=ref[25]}$ derived in Table 6 using an interpolation of RBE value ($W_{RBE=ref[25]}$) provided in Britten et al [25]. These data represent Hep2 human cells irradiated in a proton beam with initial energy of 87 MeV and 4.6 cm SOBP.

In some embodiments, a hot spot is defined as the highest biological dose location. A plan can be created by transverse section of 45 mm diameter circular PTV of r=15 mm single slice intersecting proton beams (30 mm, 80%-80%) using MATLAB. In some cases, two, three, four, five and six beams, with 45°, 90°, 135° and 180° separation, intersect the PTV such that their DDF are at the distal side of the PTV. The dose distribution for these beams were calculated using the standard uniform $W_{RBE=1.1}$. The dose distributions were then recalculated using the Britten et al. $W_{RBE=ref[25]}$ values for Hep2 cells, $E_o$=87 MeV, SOBP=4.5 cm and normalized to $W_{RBE=1.1}$. These $W_{RBE=ref[25]}$ values were depth and energy dependent and varied along the SOBP.

Figure 11B:
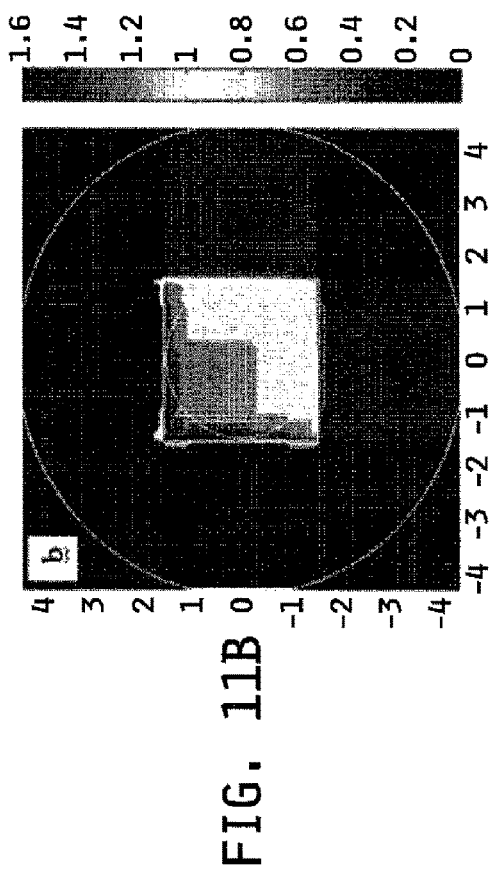
FIGS. 11A-11C show an isodose distribution profile of two proton beams with 0° and 270° and incident energy of 87 MeV.
Figure 11A:
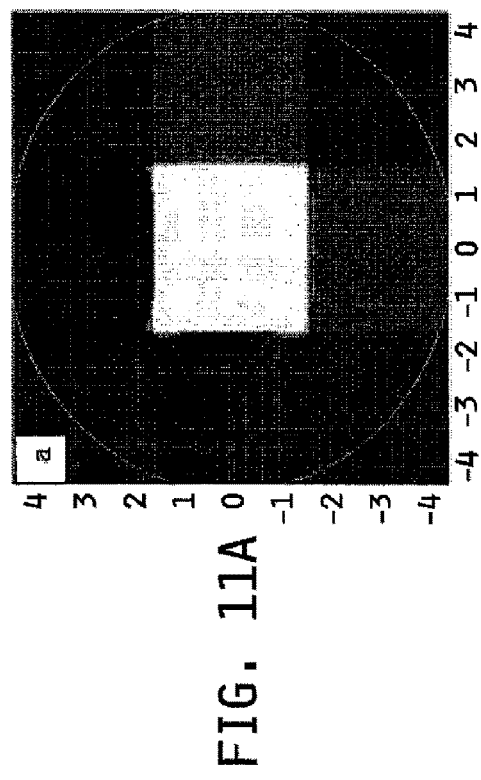
Figure 11C:
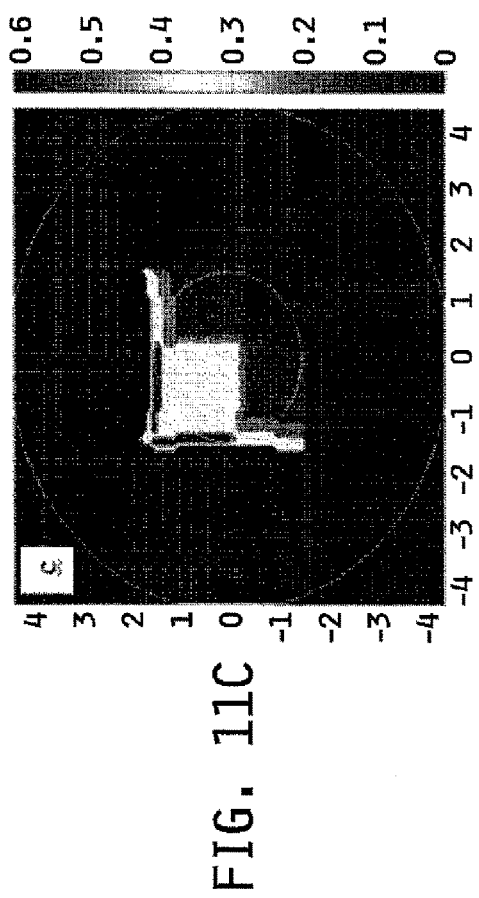

Referring now to FIGS. 10-15, FIG. 10 shows a comparison between the biologic dose and physical dose in one embodiment of proton beat therapy. FIG. 11 shows an isodose distribution profile of two proton beams with 0° and 270° and incident energy of 87 MeV. FIG. 11(a) shows $W_{RBE=1.1}$, FIG. 11(b) shows $W_{RBE=ref[25]}$ and FIG. 11(c) shows the difference in isodose distribution between RBEs for Hep2 human cells. The PTV is 30 mm in diameter and the transverse section is 90 mm in diameter.

Figure 13A:
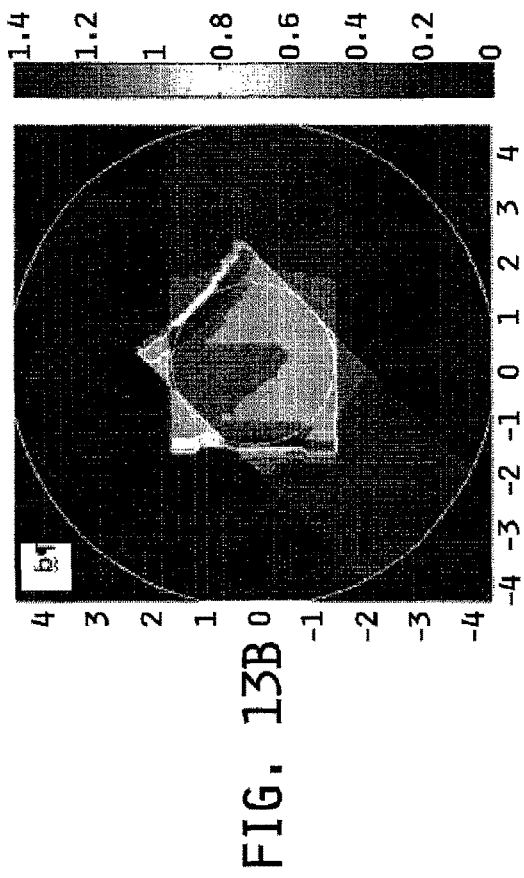
FIGS. 13A-13C show an isodose distribution profile of two proton beams with 0° and 225° and incident energy of 87 MeV.
Figure 13B:
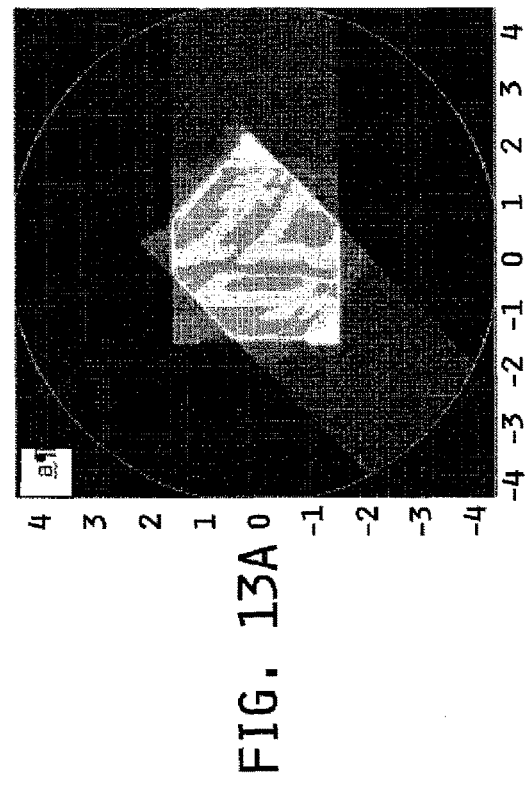
Figure 13C:
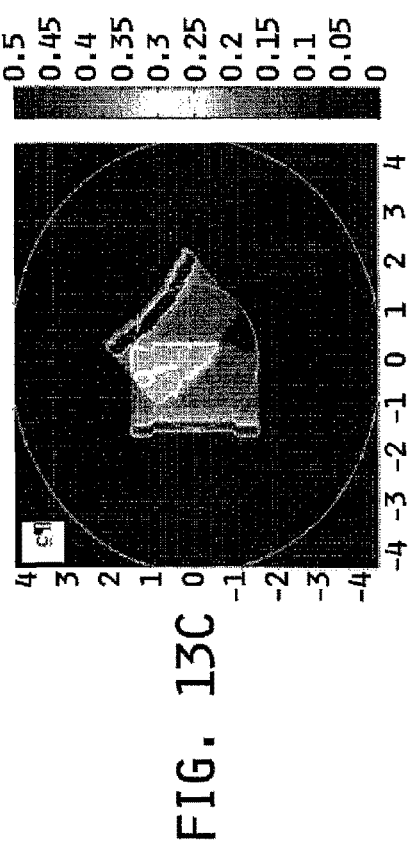

FIG. 12 shows an isodose distribution profile of two proton beams with 0° and 315° and incident energy of 87 MeV. FIG. 12(a) shows $W_{RBE=1.1}$, FIG. 12(b) shows $W_{RBE=ref[25]}$, and FIG. 12(c) shows the difference in isodose distribution between RBEs for Hep2 human cells. The PTV is 30 mm in diameter and the transverse section is 90 mm in diameter. FIG. 13 shows an isodose distribution profile of two proton beams with 0° and 225° and incident energy of 87 MeV. FIG. 13(a) shows $W_{RBE=1.1}$, FIG. 13(b) shows $W_{RBE=ref[25]}$ and FIG. 13(c) shows the difference in isodose distribution between RBEs for Hep2 human cells. The PTV is 30 mm in diameter and the transverse section is 90 mm in diameter.

Figure 14B:
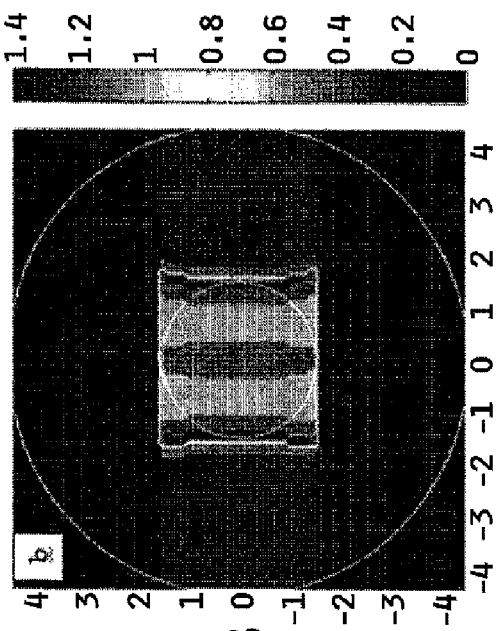
FIGS. 14A-14C shows an isodose distribution profile of two proton beams with 0° and 180° and incident energy of 87 MeV.
Figure 14C:
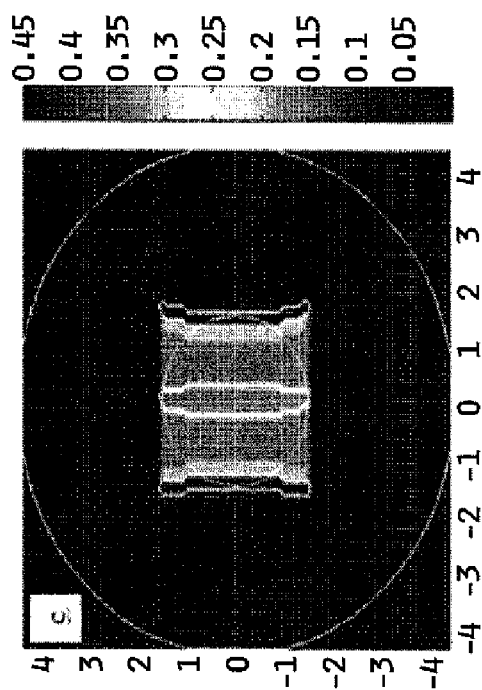
Figure 14A:
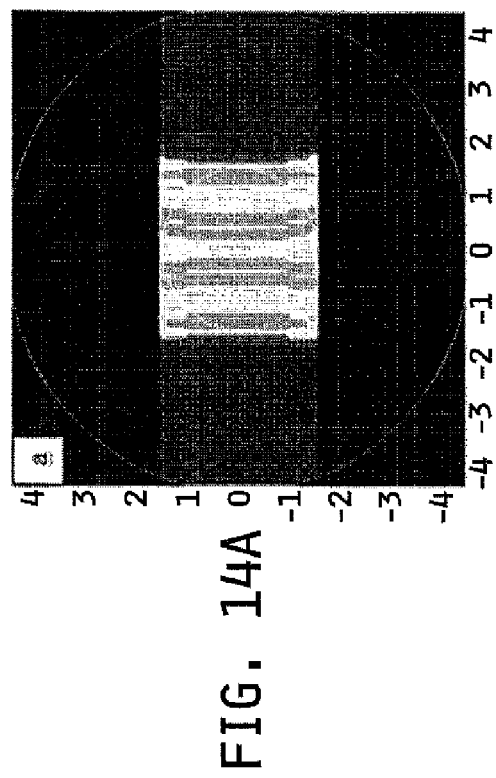

FIG. 14 shows an isodose distribution profile of two proton beams with 0° and 180° and incident energy of 87 MeV. FIG. 14(a) shows $W_{RBE=1.1}$, FIG. 14(b) shows $W_{RBE=ref[25]}$ and FIG. 14(c) shows the difference in isodose distribution between RBEs for Hep2 human cells. The PTV is 30 mm in diameter and the transverse section is 90 mm in diameter. FIG. 15 shows an isodose distribution profile of two proton beams with 225° and 315° and incident energy of 87 MeV. FIG. 15 (a) shows $W_{RBE=1.1}$, FIG. 15 B shows (b) $W_{RBE=ref[25]}$, and FIG. 15(c) shows the difference in isodose distribution between RBEs for Hep2 human cells. The PTV is 30 mm in diameter and the transverse section is 90 mm in diameter.

FIGS. 11-15 provide the results for two beam intersections within the PTV. For two beams with 90° angle between them, the hot spots are inside the PTV. The corrected $W_{RBE=ref[25]}$ relative dose hot spots are concentrated at the distal corners whereas the uniform $W_{RBE=1.1}$ appears to be spread evenly (see FIGS. 11 and 15). At the hot spots, the corrected $W_{RBE=ref[25]}$ dose is 60% greater than the uniform $W_{RBE=1.1}$. The dose distribution using a uniform $W_{RBE=1.1}$ or corrected $W_{RBE=ref[25]}$ have no considerable differences at the PTV entrance. Lesser increases in close in the range between 15%-35% can be seen at the provincial corners.

When the angle between the two beams is 45°, the hot spot (bright red) is slightly outside the PTV (see FIG. 12). For the corrected $W_{RBE=ref[25]}$, a considerable green area is observed outside the PTV, which has a relative dose value of 1.0. The corrected $W_{RBE=ref[25]}$ dose of the hot spots is 100% greater than the uniform $W_{RBE=1.1}$ dose. In general, the corrected $W_{RBE=ref[25]}$ relative dose in the mid-distal SOBP beam edges are between 40%-80% greater than the uniform $W_{RBE=1.1}$ doses.

The two beams with 135° angle between them have hot spots that are slightly outside the PTV as shown in FIG. 13. For the dose distribution using the corrected $W_{RBE=ref[25]}$, 100% and 90% of relative dose appear outside of the PTV. The corrected $W_{RBE=ref[25]}$ dose of the hot spot is 50% greater than the uniform $W_{RBE=1.1}$ dose. In general, the dose distribution using $W_{RBE=ref[25]}$ values are between 20%-45% greater than the standard $W_{RBE=1.1}$ dose.

When the angle between two beams is 180° the corrected $W_{RBE=ref[25]}$ generated hot spots are completely inside the PTV (see FIG. 14). The dose at the hot spot is 40% greater than that predicted by the clinical standard. In general, these dose distributions are 15%-35% greater than those that would be generated by a corrected planning system.

Figure 16A:
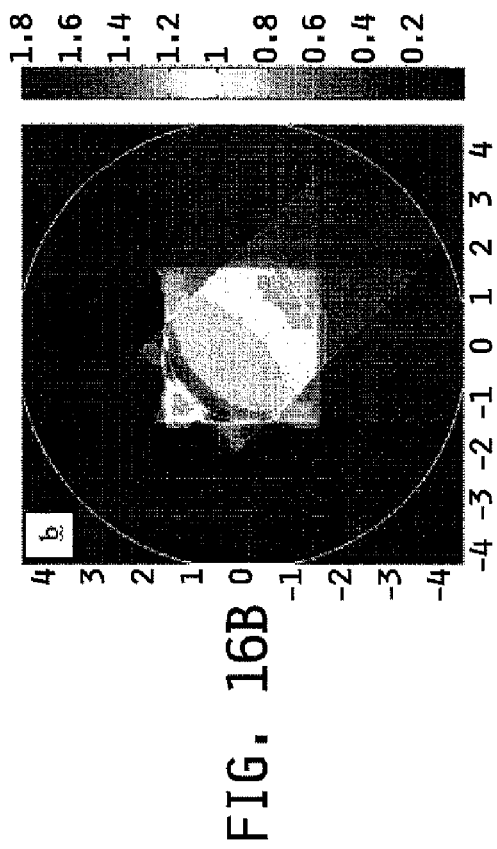
FIGS. 16A-16C show an isodose distribution profile of three proton beams with 0°, 270° and 315° and incident energy of 87 MeV.
Figure 16B:
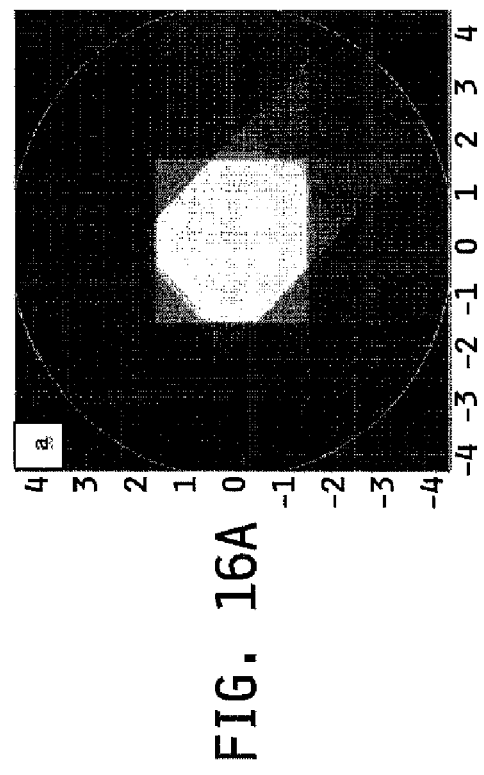
Figure 16C:
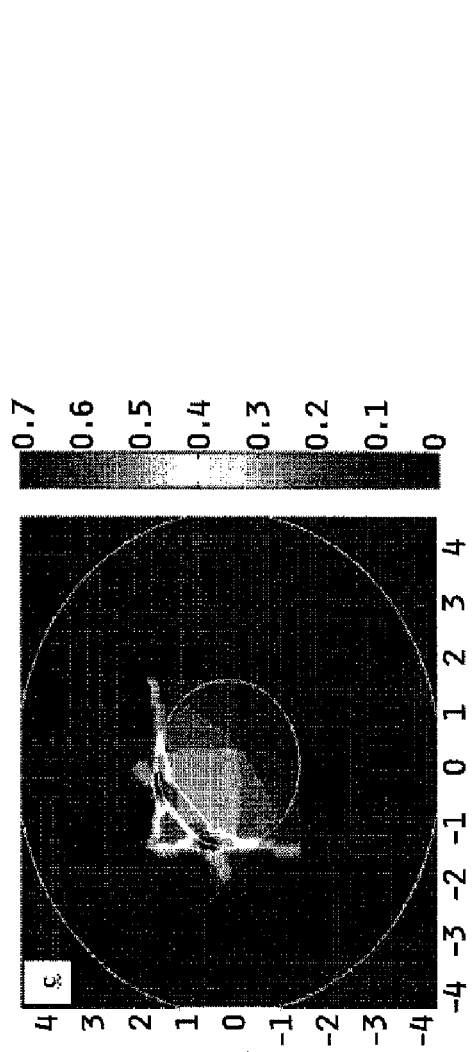

Referring now to FIGS. 16-19, these figures show the result for two beams intersections within the PTV. FIG. 16 shows an isodose distribution profile of three proton beams with 0°, 270° and 315° and incident energy of 87 MeV. FIG. 16(a) shows $W_{RBE=1.1}$, FIG. 16(b) shows $W_{RBE=ref[25]}$ and FIG. 16(c) shows the difference in isodose distribution between RBEs for Hep2 human cells. The PTV is 30 mm in diameter and the transverse section is 90 mm in diameter.

Figure 17A:
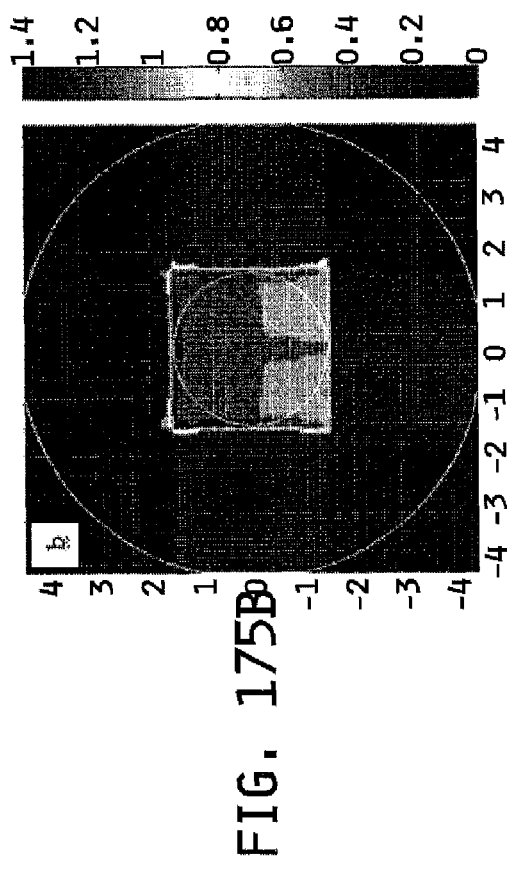
FIGS. 17A-17C show an isodose distribution profile of three proton beams with 0°, 180° and 270° and incident energy of 87 MeV.
Figure 17B:
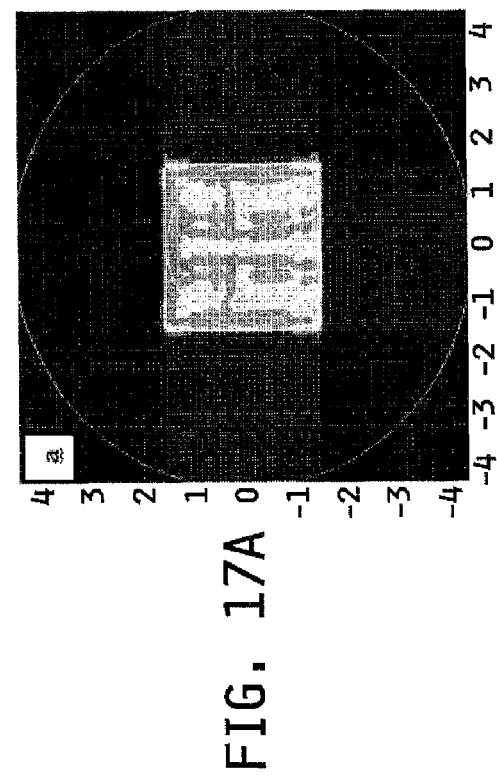
Figure 17C:
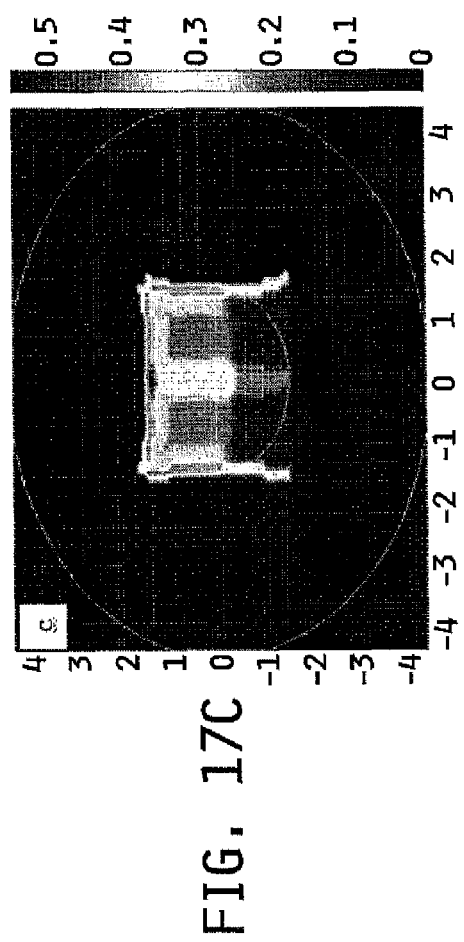

FIG. 17 shows an isodose distribution profile of three proton beams with 0°, 180° and 270° and incident energy of 87 MeV. FIG. 17(a) shows $W_{RBE=1.1}$, FIG. 17(b) shows $W_{RBE=ref[25]}$ and FIG. 17(c) shows the difference in isodose distribution between RBEs for Hep2 human cells. The PTV is 30 mm in diameter and the transverse section is 90 mm in diameter.

Figure 18A:
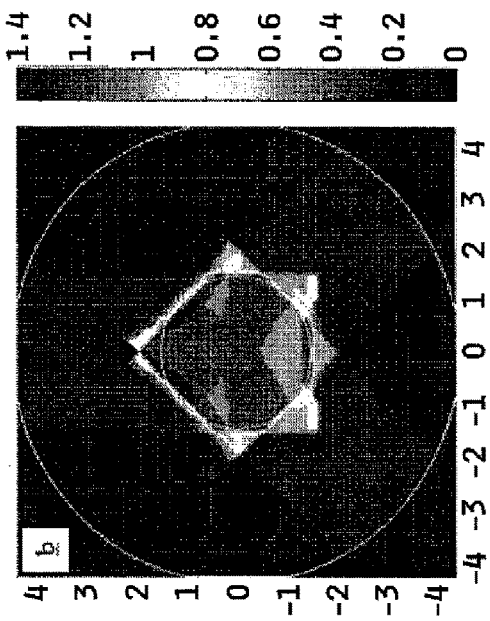
FIGS. 18A-18C show an isodose distribution profile of three proton beams with 90°, 225° and 315° and incident energy of 87 MeV.
Figure 18B:
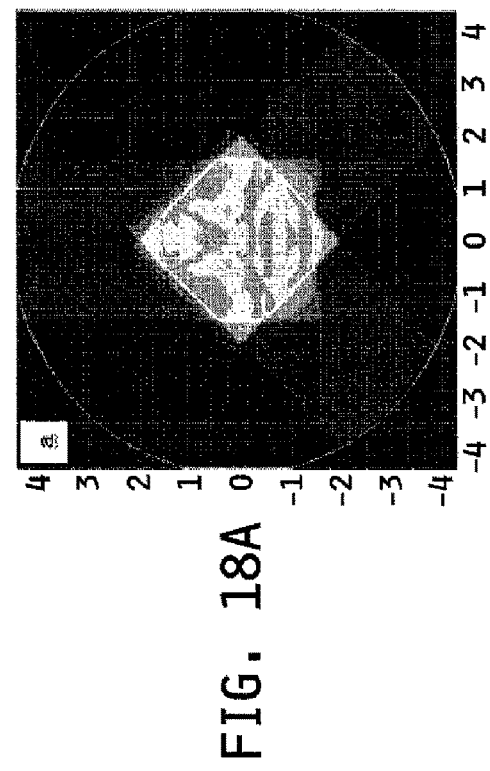
Figure 18C:
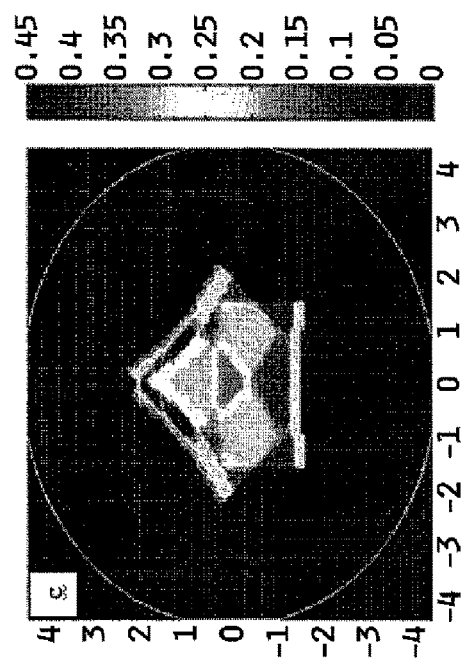

FIG. 18 shows an isodose distribution profile of three proton beams with 90°, 225° and 315° and incident energy of 87 MeV. FIG. 18(a) shows $W_{RBE=1.1}$, FIG. 18(b) shows $W_{RBE=ref[25]}$ and FIG. 18(c) shows the difference isodose distribution between RBEs for Hep2 human cells. The PTV is 30 mm in diameter and the transverse section is 90 mm in diameter.

Figure 19B:
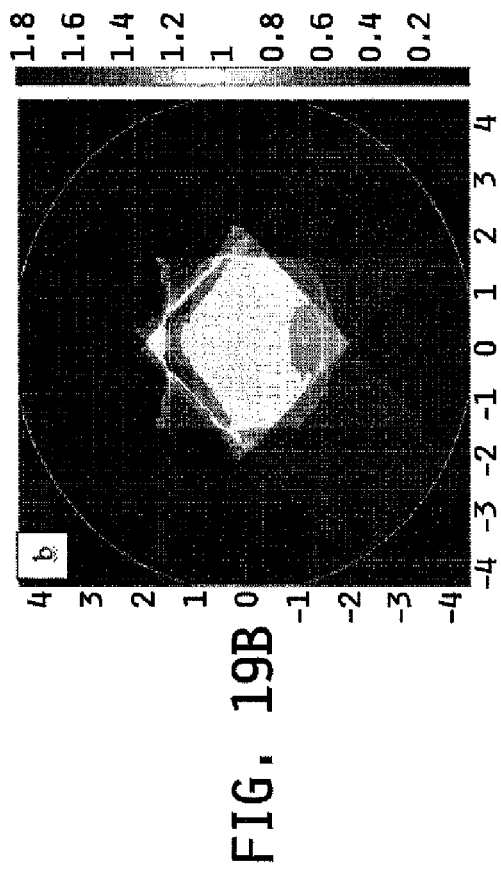
FIGS. 19A-19C show an isodose distribution profile of three proton beams with 225°, 270° and 315° and incident energy of 87 MeV.

FIG. 19 shows an isodose distribution profile of three proton beams with 225°, 270° and 315° and incident energy of 87 MeV. FIG. 19 (a) shows $W_{RBE=1.1}$, FIG. 19(b) shows $W_{RBE=ref[25]}$ and FIG. 20(c) shows the difference in isodose distribution between RBEs for Hep2 human cells. The PTV is 30 mm in diameter and the transverse section is 90 mm in diameter.

For three beams with 45° angle between them the hot spot is slightly outside the PTV. The corrected $W_{RBE=ref[25]}$ relative dose hot spots are concentrated at the distal corners whereas the uniform $W_{RBE=1.1}$ appears to be spread evenly (see FIGS. 16 and 19). At the hot spots, the corrected $W_{RBE=ref[25]}$ dose is 70% greater than the uniform $W_{RBE=1.1}$. For the corrected $W_{RBE=ref[25]}$ dose distribution, a considerable yellow area is observed outside the PTV that has relative dose value of 1.15. The dose distribution using a uniform $W_{RBE=1.1}$ or corrected $W_{RBE=ref[25]}$ have no considerable differences at the PTV entrance. Lesser increases in close in the range between 20%-60% can be seen at the provincial corners.

When the angle between three beams is 90° the hot spot is completely inside the PTV (see FIG. 17). At the hot spots, the corrected $W_{RBE=ref[25]}$ dose is greater by 55% than the uniform $W_{RBE=1.1}$. In general, the dose distribution using $W_{RBE=ref[25]}$ values are greater ranging between 15%-45% higher than the standard $W_{RBE=1.1}$ dose.

The three beams, two of them with 90° angles between them and the third one is in a vertical position on these two beams, have hot spots that are slightly outside the PTV as shown in FIG. 18. For the dose distribution using the corrected $W_{RBE=ref[25]}$, a considerable yellow area is observed outside the PTV, which has a relative dose value of 0.85. The corrected $W_{RBE=ref[25]}$ dose of the hot spots is 45% greater than the uniform $W_{RBE=1.1}$ dose. In general, the corrected $W_{RBE=ref[25]}$ relative dose are greater ranging between 20%-40% than the uniform $W_{RBE=1.1}$ relative doses.

Figure 20B:
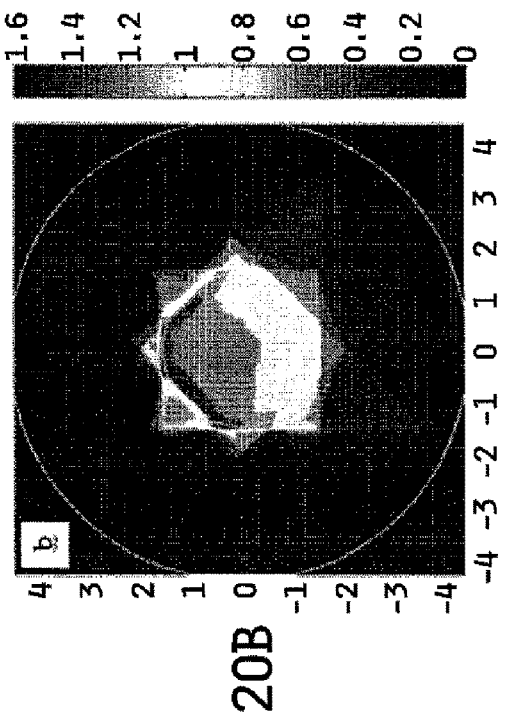
FIGS. 20A-20C show an isodose distribution profile of four proton beams with 0°, 225°, 270° and 315° and incident energy of 87 MeV.
Figure 20A:
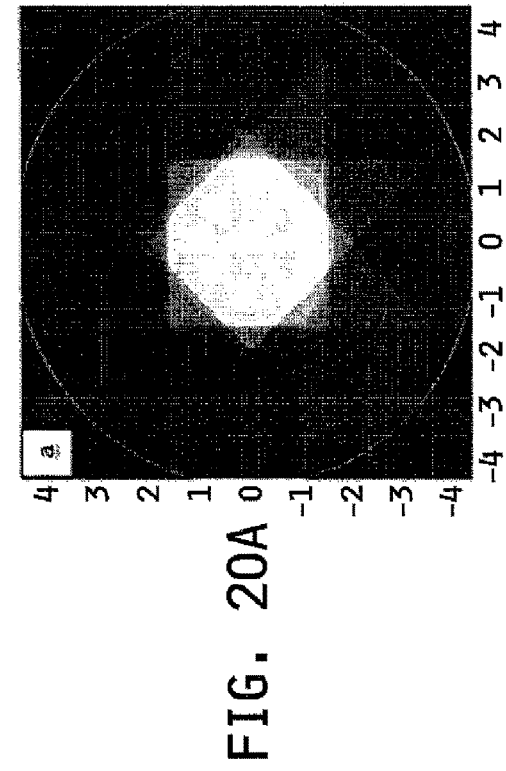

Referring now to FIGS. 20-23, the results for four beam intersections within the PTV are shown. FIG. 20 shows an isodose distribution profile of four proton beams with 0°, 225°, 270° and 315° and incident energy of 87 MeV. FIG. 20(a) shows $W_{RBE=1.1}$, FIG. 20(b) shows $W_{RBE=ref[25]}$ and FIG. 20(c) shows the difference in isodose distribution between RBEs for Hep2 human cells. The PTV is 30 mm in diameter and the transverse section is 90 mm in diameter.

Figure 21B:
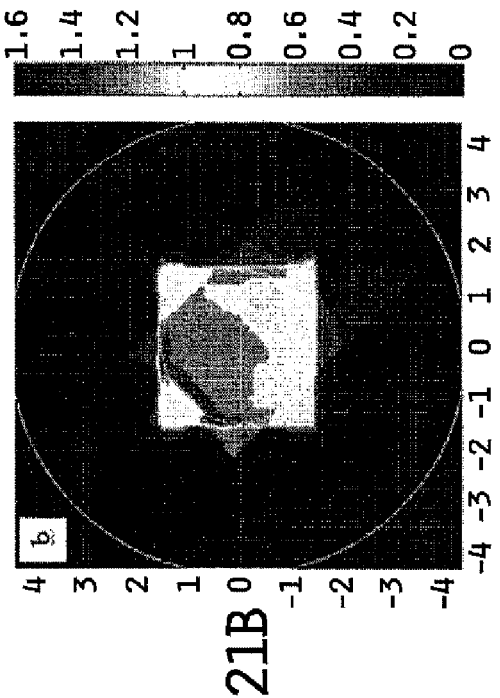
FIGS. 21A-21C show an isodose distribution profile of four proton beams with 0°, 180°, 270° and 315° and incident energy of 87 MeV.
Figure 21A:
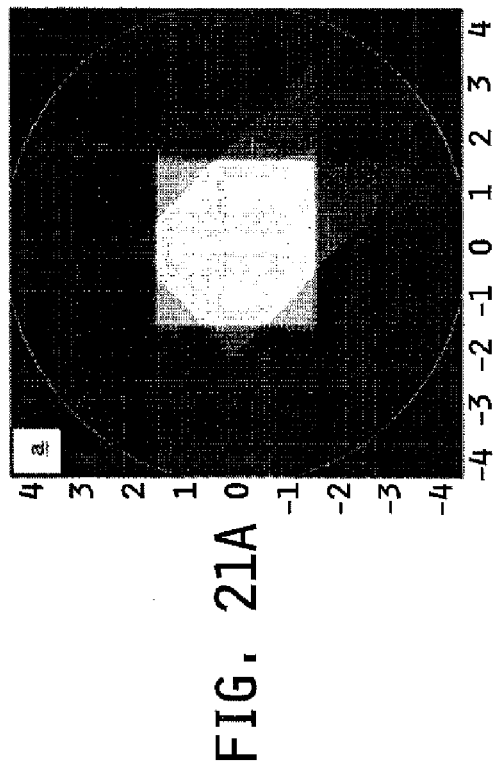
Figure 21C:
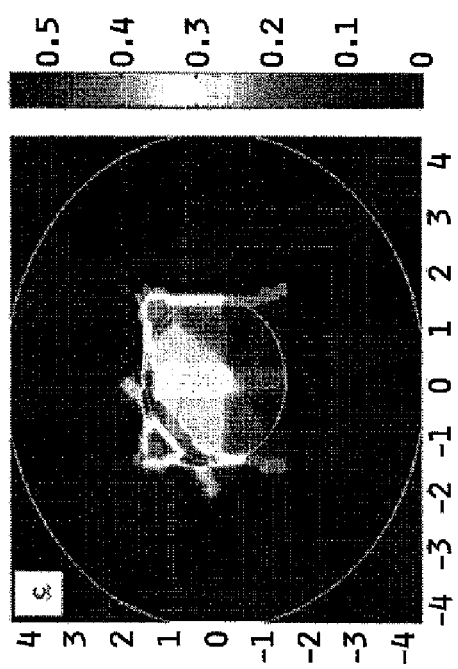

FIG. 21 shows an isodose distribution profile of four proton beams with 0°, 180°, 270° and 315° and incident energy of 87 MeV. FIG. 21(a) shows $W_{RBE=1.1}$, FIG. 21(b) shows $W_{RBE=ref[25]}$ and FIG. 21(c) shows the difference in isodose distribution between RBEs for Hep2 human cells. The PTV is 30 mm in diameter and the transverse section is 90 mm in diameter.

Figure 22B:
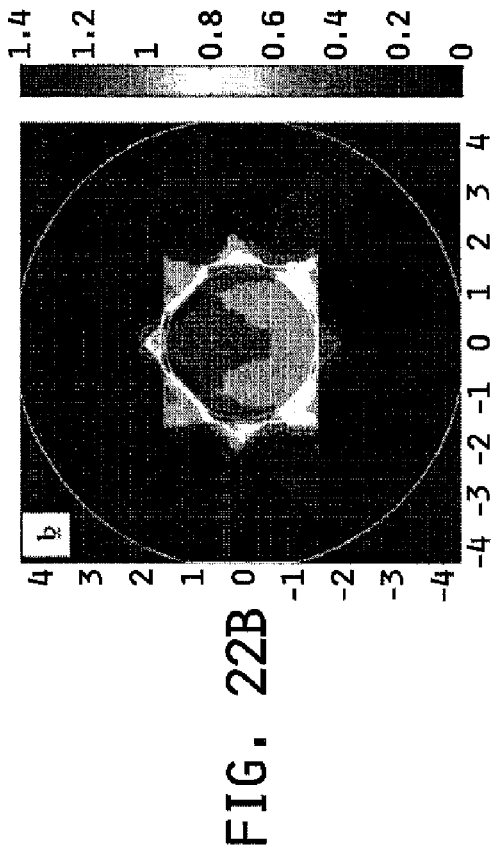
FIGS. 22A-22C show an isodose distribution profile of four proton beams with 0°, 180°, 225° and 315° and incident energy of 87 MeV.
Figure 22A:
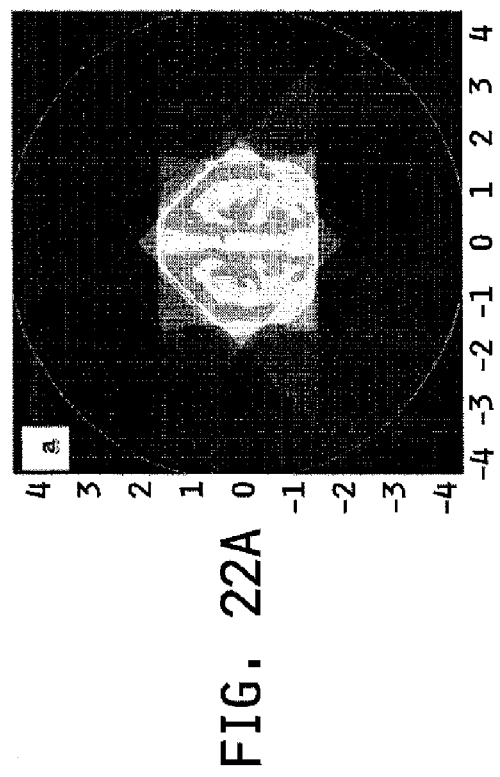
Figure 22C:
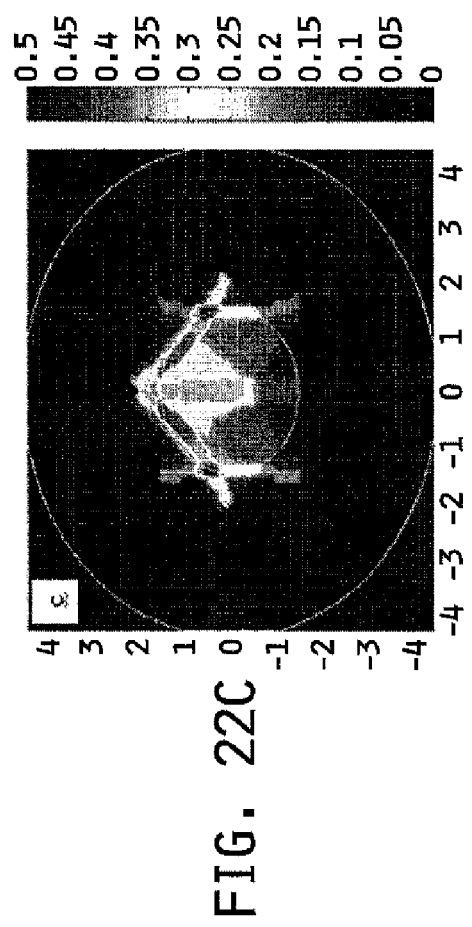

FIG. 22 shows an isodose distribution profile of four proton beams with 0°, 180°, 225° and 315° and incident energy of 87 MeV. FIG. 22(a) shows $W_{RBE=1.1}$, FIG. 22(b) shows $W_{RBE=ref[25]}$ and FIG. 22(c) shows the difference in isodose distribution between RBEs for Hep2 human cells. The PTV is 30 mm in diameter and the transverse section is 90 mm in diameter.

Figure 23B:
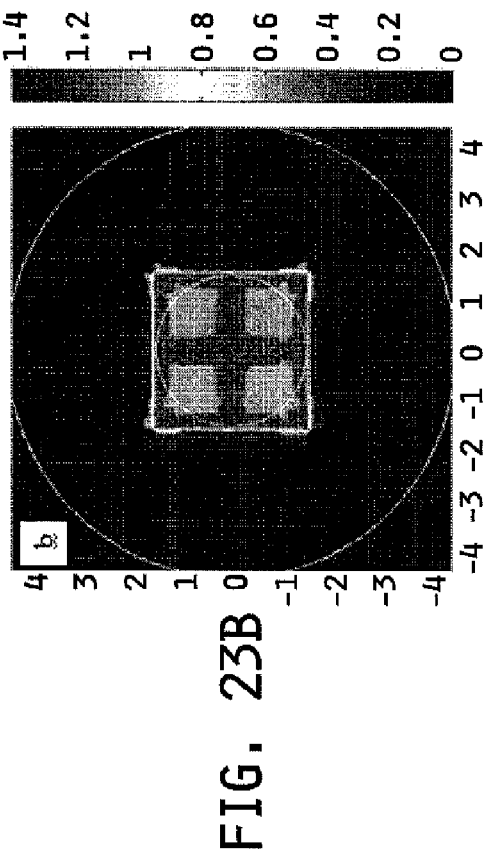
FIGS. 23A-23C show an isodose distribution profile of four proton beams with 0°, 90°, 180° and 270° and incident energy of 87 MeV.
Figure 23A:
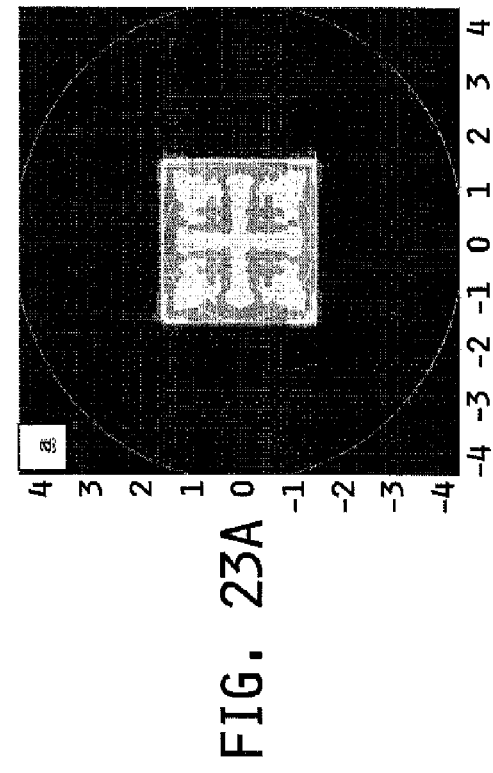
Figure 23C:
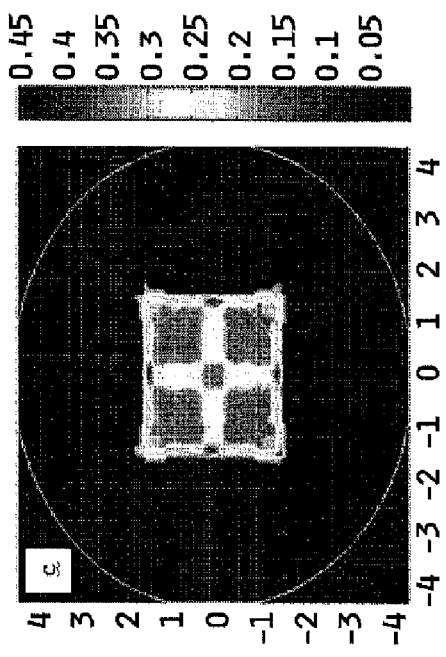

FIG. 23 shows an isodose distribution profile of four proton beams with 0°, 90°, 180° and 270° and incident energy of 87 MeV. FIG. 23(a) shows $W_{RBE=1.1}$, FIG. 23(b) shows $W_{RBE=ref[25]}$ and FIG. 23(c) shows the difference in isodose distribution between RBEs for Hep2 human cells. The PTV is 30 mm in diameter and the transverse section is 90 mm in diameter.

FIGS. 20-23 show the results for four beam intersections within the PTV. Hot spots are observed on four beams with 45° offsets (see FIG. 20). At the hot spots, the corrected $W_{RBE=ref[25]}$ dose is 60% greater than the uniform $W_{RBE=1.1}$. The dose distribution using corrected $W_{RBE=ref[25]}$ values also increased dose of the PTV to relative doses of 1.0 and 0.8 (yellow and green areas). In general, the $W_{RBE=ref[25]}$ weighted relative dose for intersection corners are between 15%-55% greater than the $W_{RBE=1.1}$ dose.

When the angle between each of four beams is increased to 90°, the $W_{RBE=ref[25]}$ hot spots are completely inside the PTV (see FIG. 23). The corrected $W_{RBE=ref[25]}$ dose at the hot spots is 45% greater than the uniform $W_{RBE=1.1}$ dose. In general, the dose distribution using corrected $W_{RBE=ref[25]}$ are between 10%-40% greater than the uniform $W_{RBE=1.1}$.

Other possibilities for four beam distributions are shown in FIGS. 21-22. These configurations have hot spots that are mostly inside the PTV. Considerable yellow areas are observed outside the PTV, which have a relative corrected $W_{RBE=ref[25]}$ dose value of 1.0 and 0.85 for FIGS. 21 and 22 respectively. The corrected $W_{RBE=ref[25]}$ hot spots are greater by 60% and 50% respectively versus the uniform $W_{RBE=1.1}$ dose. In general, the corrected $W_{RBE=ref[25]}$ relative dose are greater ranging between 20%-55% and 15%-45% respectively than the uniform $W_{RBE=1.1}$.

Figure 24B:
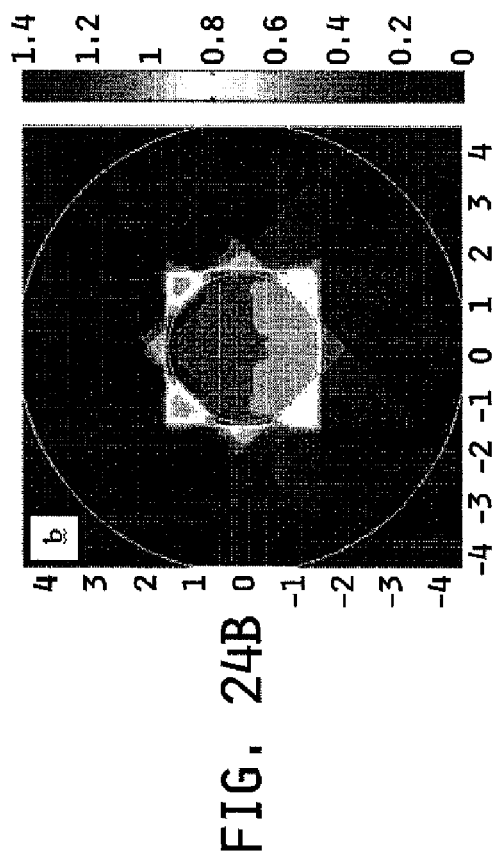
Figure 24C:
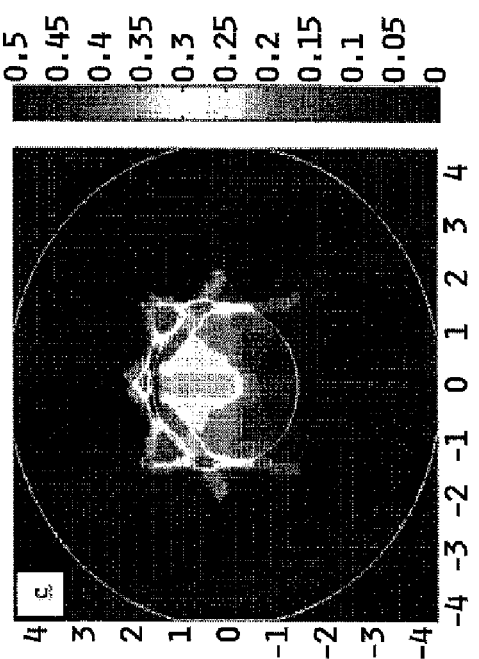
Figure 24A:
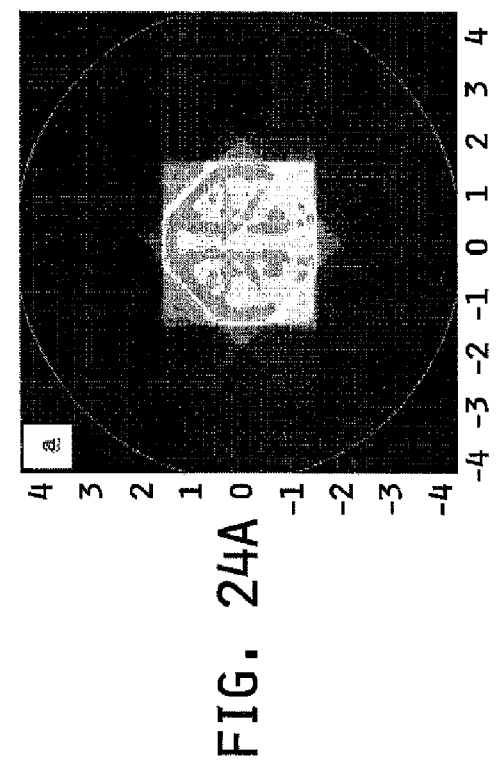

Referring now to FIGS. 24-27, the possibilities for five and six beams distributions are shown. FIG. 24 shows an isodose distribution profile of five proton beams with 0°, 180°, 225°, 270° and 315° and incident energy of 87 MeV. FIG. 24(a) shows $W_{RBE=1.1}$, FIG. 24(b) shows $W_{RBE=ref[25]}$ and FIG. 24(c) shows the difference in isodose distribution between RBEs for Hep2 human cells. The PTV is 30 mm in diameter and the transverse section is 90 mm in diameter.

Figure 25B:
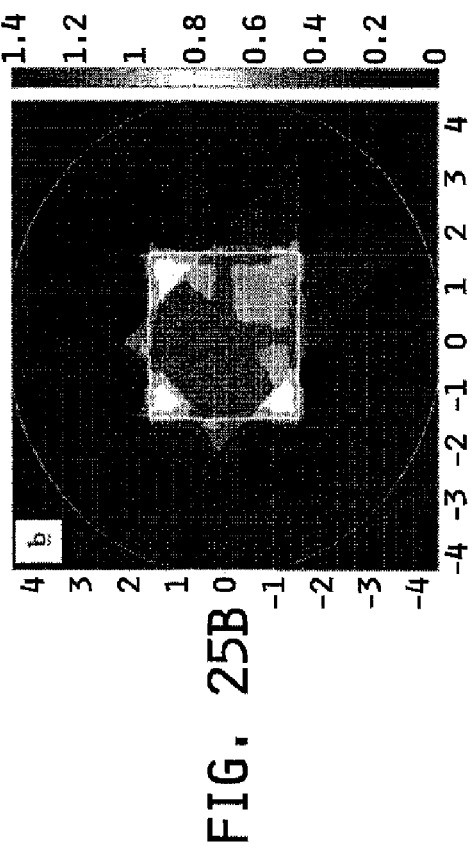
FIGS. 25A-25C show an isodose distribution profile of five proton beams with 0°, 90°, 180°, 270° and 315° and incident energy of 87 MeV.
Figure 25C:
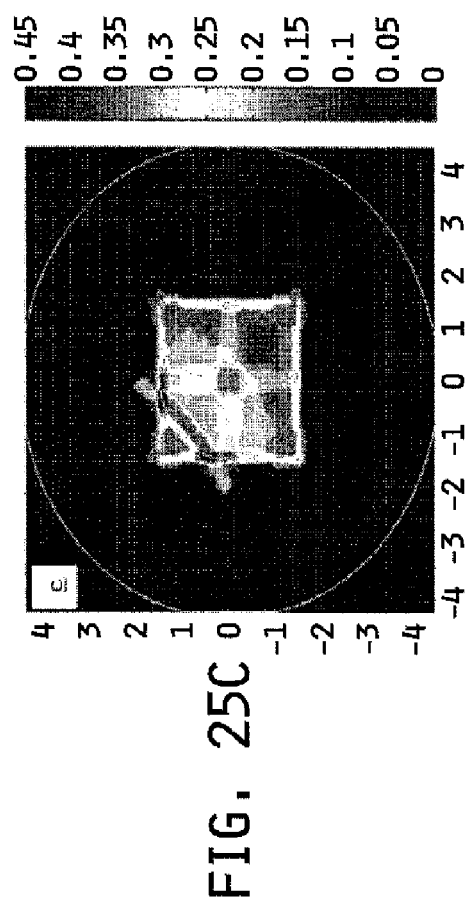
Figure 25A:
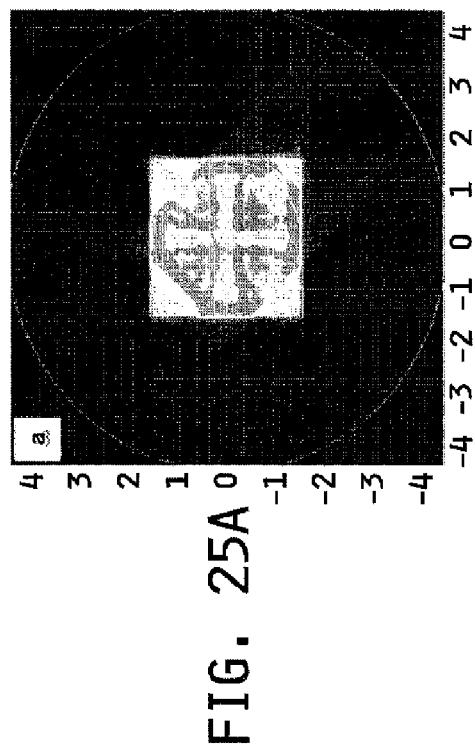

FIG. 25 shows an isodose distribution profile of five proton beams with 0°, 90°, 180°, 270° and 315° and incident energy of 87 MeV. FIG. 25(a) shows $W_{RBE=1.1}$, FIG. 25(b) shows $W_{RBE=ref[25]}$ and FIG. 25(c) shows the difference in isodose distribution between RBEs for Hep2 human cells. The PTV is 30 mm in diameter and the transverse section is 90 mm in diameter.

Figure 27B:
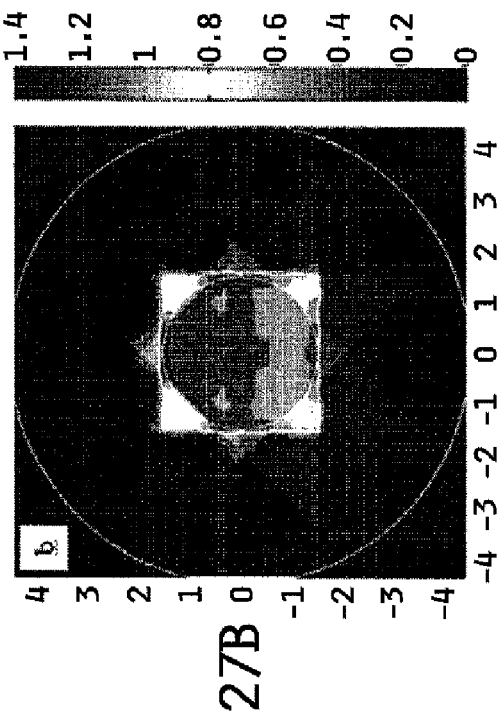
FIGS. 27A-27C shows an isodose distribution profile of six proton beams with 0°, 90°, 180°, 225°, 270° and 315° and incident energy of 87 MeV.
Figure 27C:
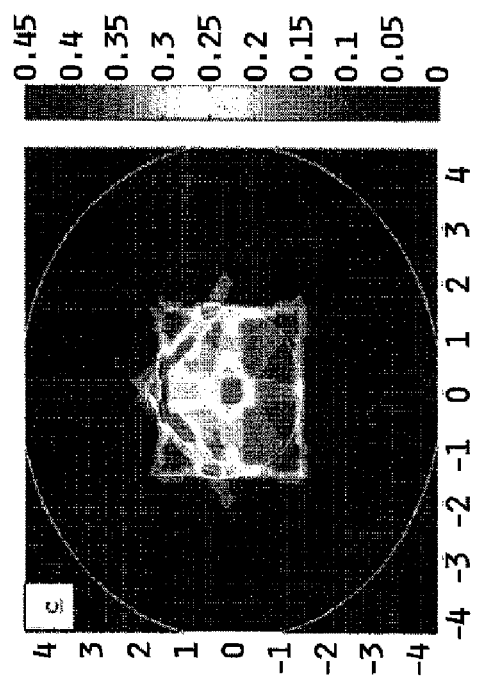
Figure 27A:
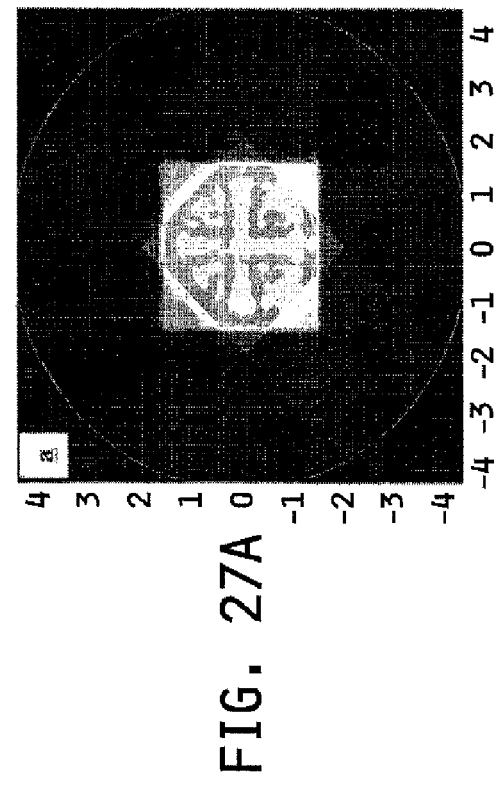

FIG. 26 shows an isodose distribution profile of five proton beams with 0°, 90°, 225°, 270° and 315° and incident energy of 87 MeV. FIG. 26 shows (a) $W_{RBE=1.1}$, FIG. 26 shows (b) $W_{RBE=ref[25]}$ and FIG. 26(c) shows the difference in isodose distribution between RBEs for Hep2 human cells. The PTV is 30 mm in diameter and the transverse section is 90 mm in diameter. FIG. 27 shows an isodose distribution profile of six proton beams with 0°, 90°, 180°, 225°, 270° and 315° and incident energy of 87 MeV. FIG. 27(a) shows $W_{RBE=1.1}$, FIG. 27(b) shows $W_{RBE=ref[25]}$ and FIG. 27(c) shows the difference in isodose distribution between RBEs for Hep2 human cells. The PTV is 30 mm in diameter and the transverse section is 90 mm in diameter.

In FIGS. 24-27, the configurations have hot spots that are mostly distributed inside the PTV. The corrected $W_{RBE=ref[25]}$ hot spots are 45% or 40% greater than the uniform $W_{RBE=1.1}$ dose. Considerable blue areas are observed outside the PTV that have relative corrected $W_{RBE=ref[25]}$ dose value between 0.6 and 0.7. In general, the corrected $W_{RBE=ref[25]}$ relative doses are 15%-40% higher than the uniform $W_{RBE=1.1}$.

The RBE weighting factor of the proton beams compared with x-rays most frequently used is between 1.1 and 1.2 at all positions within the treatment field. However RBE strongly correlates with Linear Energy Transfer (LET) and increases along the trajectory of the penetrating proton inside the body particularly near the end of range. Increased LET has been shown to correlate with increased DNA double-strand break ("DSB"), so at the distal end, where the protons have a higher LET, the RBE weighting factor likely increases.

SOBP's are composed of several overlapping pristine Bragg peaks resulting from a distribution of initial energy beams. Therefore the $W_{RBE=1.1}$ likely is not accurate for each case where the beam energy and SOBP extent may vary. Several investigations have supported this proposal that by measuring variation in experimentally determined RBEs for both in vitro and in vivo systems.

Experimental conditions used various cell lines with differences in sampling along the SOBP, initial beam energy, RBE calculation method, tissue type and LET estimation of protons. In some embodiments, the in vitro RBEs determination ranged in the proximal SOBP from 0.86 to 1.63, in the mid-SOBP from 0.86 to 2.1, in the distal of SOBP from 0.86 to 2.1, and in the distal fall-off of SOBP from 1.39 to 2.3. The in vivo data of RBE estimation ranged in mid-SOBP from 0.73 to 1.55.

Figure 28B:
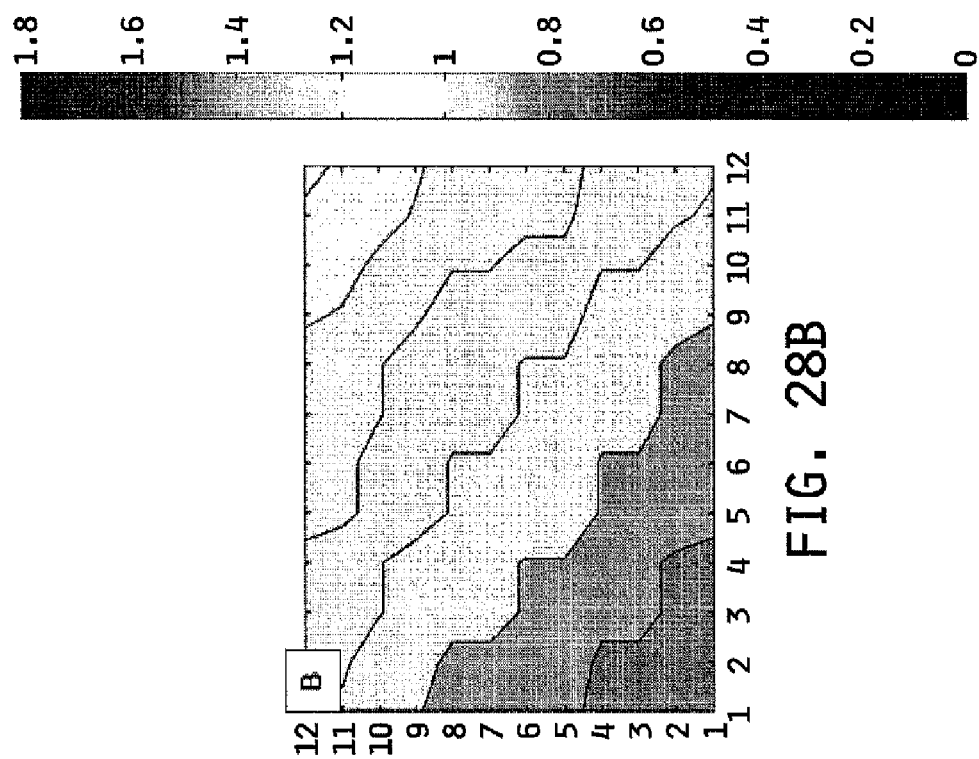
FIG. 28A-28Z and 28AA-28MM shows the PTV isodose distributions of two proton beams delivered from 180° (bottom of figure) and 270° (left of figure) calculated using the $W_{RBE}$ values along the SOBP according to experiments performed in vitro (FIGS. 28A-28HH) and in vivo (FIGS. 28II-28MM).
Figure 28A:
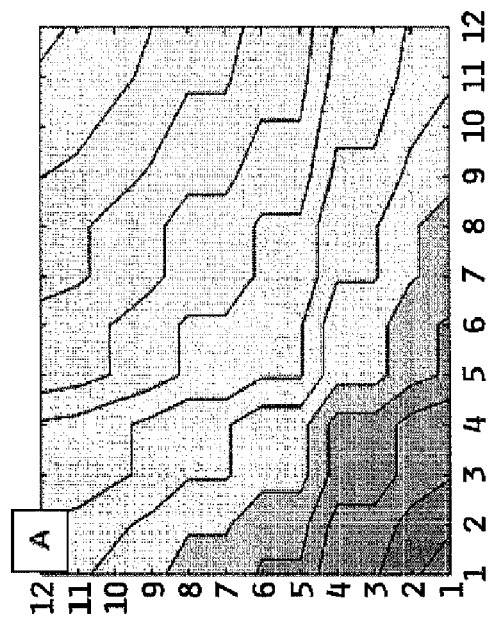
Figures 28E, 28F:
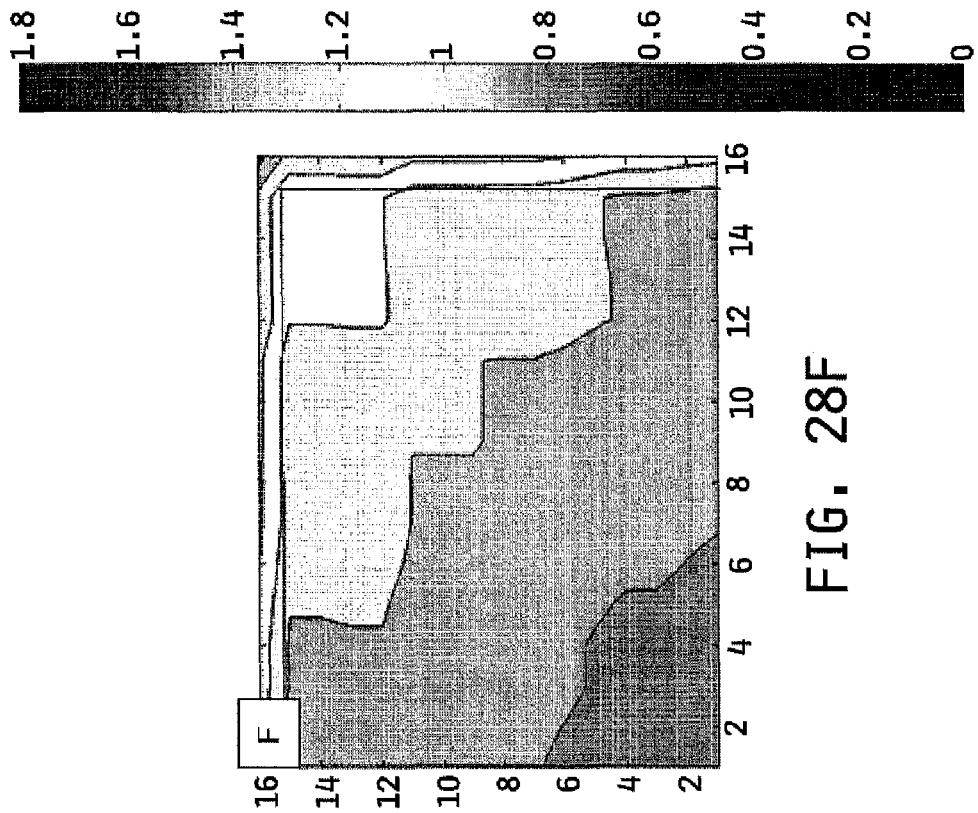
Figure 28H:
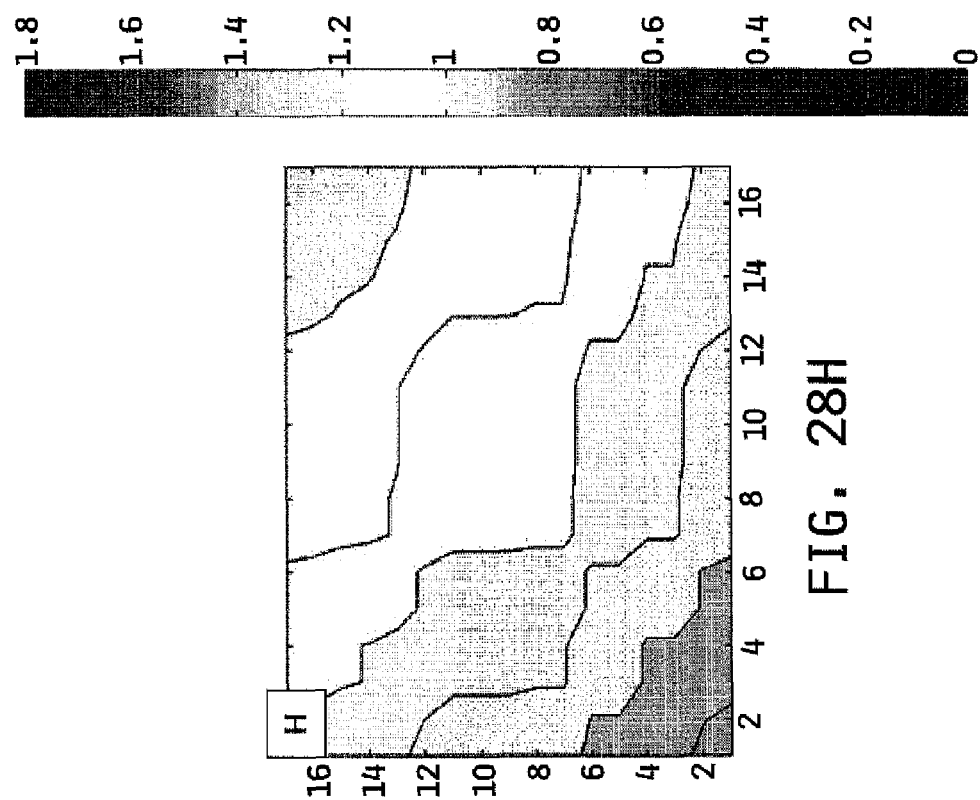
Figure 28G:
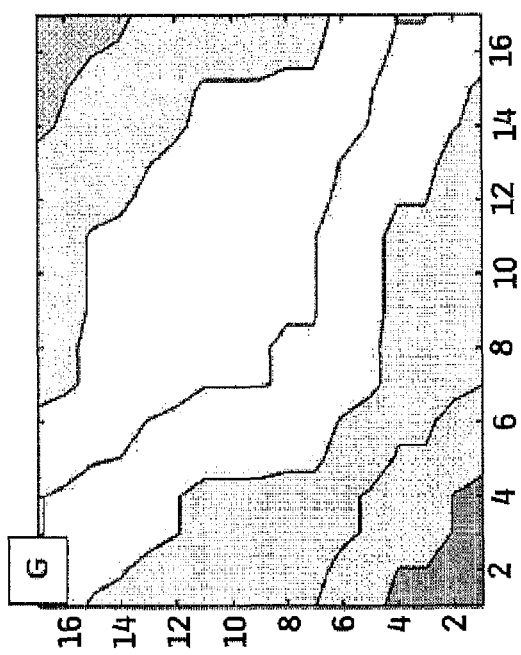

Referring now to FIGS. 28AA-28MM, variation in the estimated values of RBE influences the isodose distribution if the $W_{RBE}$ were applied to the treatment planning algorithm. In other words, various published RBE values might result in drastically different biological dose during treatment. The potential differences in biological dose can be clearly visualized if the isodose distributions of treatment plans of two beams at 90 degree separation in two-dimensions are represented as illustrated in FIG. 28. FIG. 28 shows the PTV isodose distributions of two proton beams delivered from 180° (bottom of figure) and 270° (left of figure) calculated using the $W_{RBE}$ values along the SOBP according to experiments performed in vitro (FIGS. 28A-28HH) and in vivo (FIGS. 28II-28MM). In each case, the PTV dimensions correlate with the extent of the SOBP and the biological dose is normalized to the 100% intended dose at the standard $W_{RBE=1.1}$.

Tables 7 [a-g] below describe the results presented in FIG. 28.

Table 7a for FIGS. 28A-28F.

| FIG. 28 | Biological system: | Incident energy: | SOBP | RBE in the SOBP | | | |
|---|---|---|---|---|---|---|---|
| | | | | proximal | mid | distal | Fall-off |
| A | Human melanoma cells. | 65 MeV | 12 mm (1 unit = 1 mm) | 1.09 | 1.12 | 1.19 1.27 | |
| B | | | | | | | |
| C | Human tumor SCC25 cells | | 15 mm (1 unit = 1 mm) | 1.05 1.04 | 1.1 | 1.22 | 1.39 2.05 1.34 1.98 |
| D | | | | | | | |
| E | | | | | | | |
| F | | | | | | | |

Table 7b for FIGS. 28G-28K.

| FIG. 28 | Biological system: | Incident energy: | SOBP | RBE in the SOBP | | |
|---|---|---|---|---|---|---|
| | | | | proximal | mid | distal |
| G | Chinese hamster ovary cells. | 65 MeV | 17 mm (1 unit = 1 mm) | 1.22 | 1.27 | 1.42 |
| H | | | | 1.19 | 1.23 | 1.37 |
| I | | | | 1.14 | 1.18 | 1.27 |
| J | | | | 1.1 | 1.12 | 1.19 |
| K | | | | 1.09 | 1.12 | 1.16 |

Table 7c for FIGS. 28L-28Q.

| FIG. 28 | Biological system: | Incident energy: | SOBP | RBE in the SOBP | | |
|---|---|---|---|---|---|---|
| | | | | proximal | mid | distal |
| L | Chinese hamster V79 cells | 67 MeV | 20 mm (1 unit = 1 mm) | 1.63 | 1.63 | 1.63 |
| M | | | | 1.25 | 1.25 | 1.25 |
| N | | | | 1.24 | 1.24 | 1.24 |
| O | Human colon carcinoma cells | | | 1.21 | 1.21 | 1.21 |
| P | | | | 0.86 | 0.86 | 0.86 |
| Q | | | | 1.23 | 1.23 | 1.23 |

Table 7d for FIGS. 28R-28W.

| FIG. 28 | Biological system: | Incident energy: | SOBP | RBE in the SOBP | | |
|---|---|---|---|---|---|---|
| | | | | proximal | mid | distal |
| R | Human colon carcinoma cells | 67 MeV | 20 mm (1 unit = 1 mm) | 1.11 | 1.11 | 1.11 |
| S | | | | 1.26 | 1.26 | 1.26 |
| T | Chinese hamster V79 cells | 70 MeV | 20 mm (1 unit = 1 mm) | 1.48 | 1.5 | 1.59 |
| U | | | | 1.28 | 1.3 | 1.38 |
| V | Chinese hamster ovary cells. | 85 MeV | 5 mm (1 unit = 1 mm) | 0.9 | 0.9 | 0.9 |
| W | | | | 1.1 | 1.13 | 1.13 |

Figure 28J:
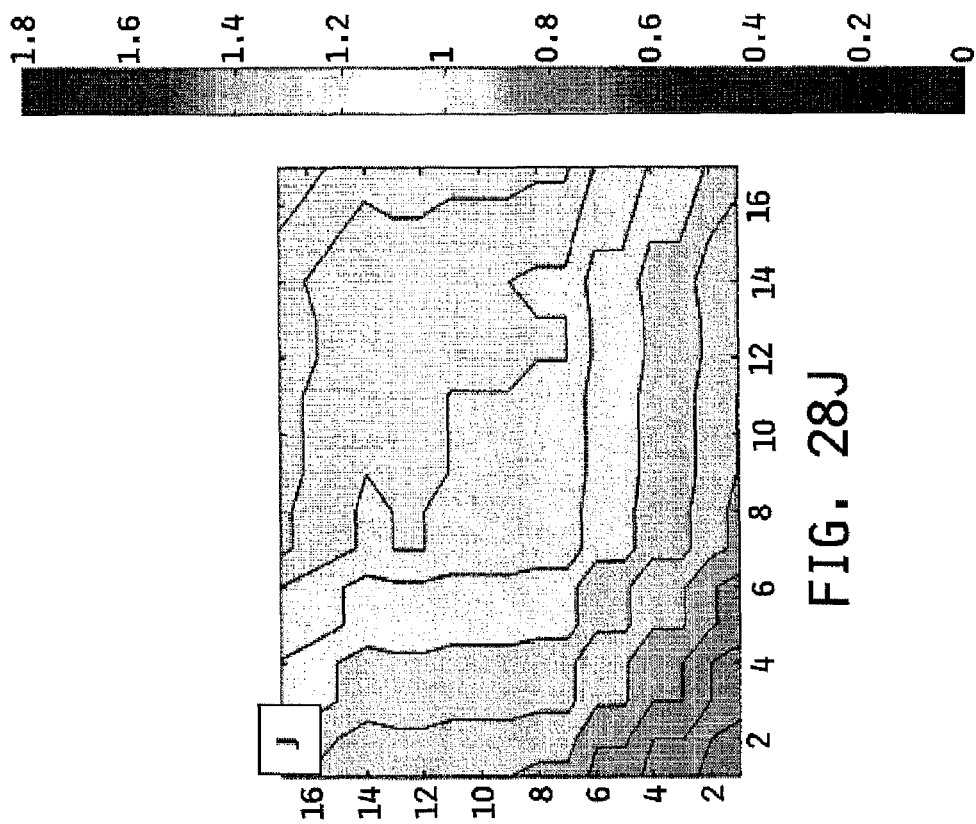
Figure 28I:
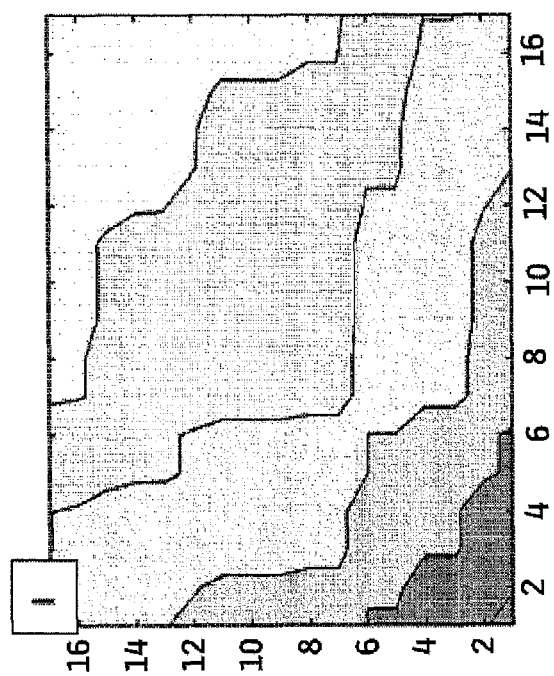
Figure 28K:
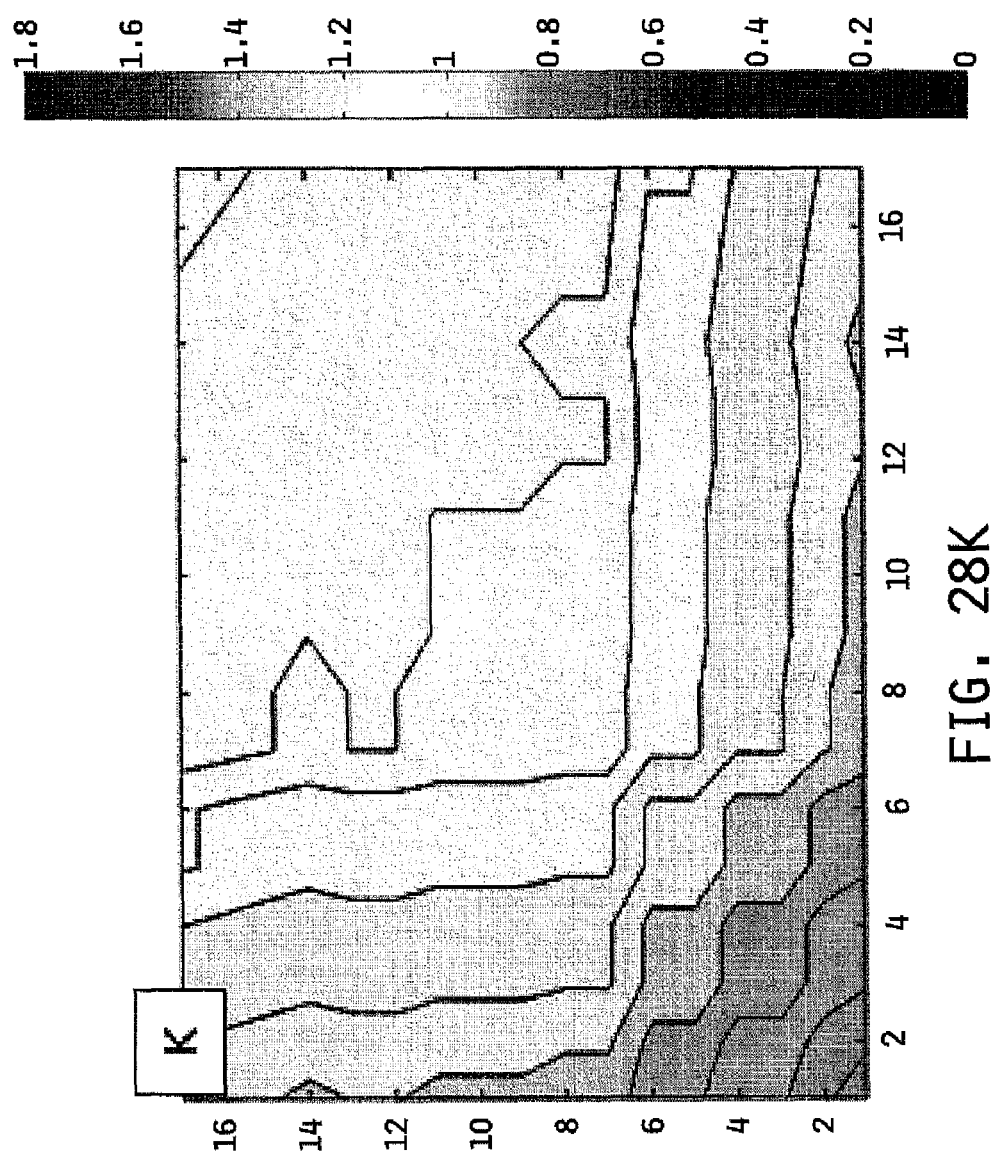
Figure 28M:
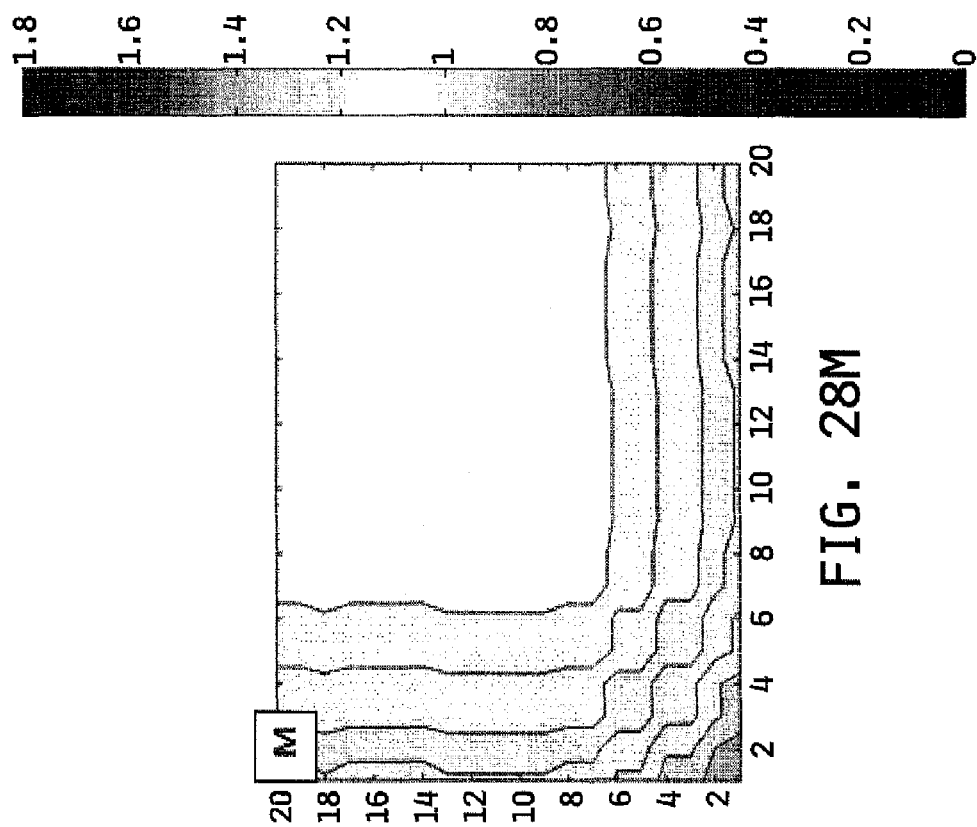
Figure 28L:
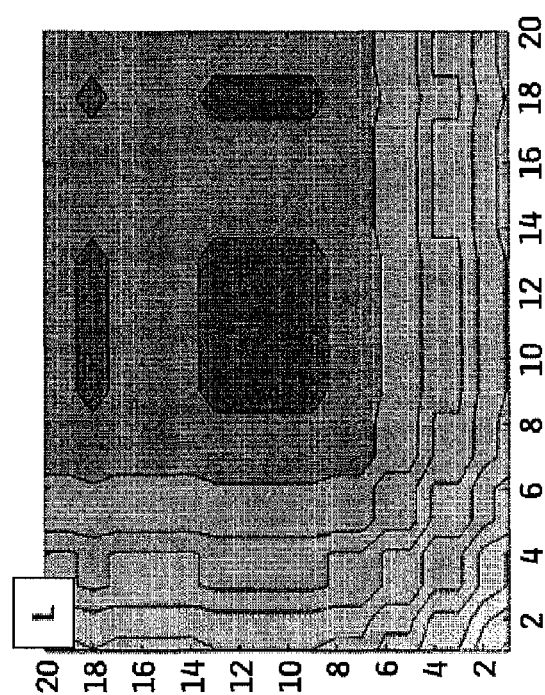
Figure 28Y:
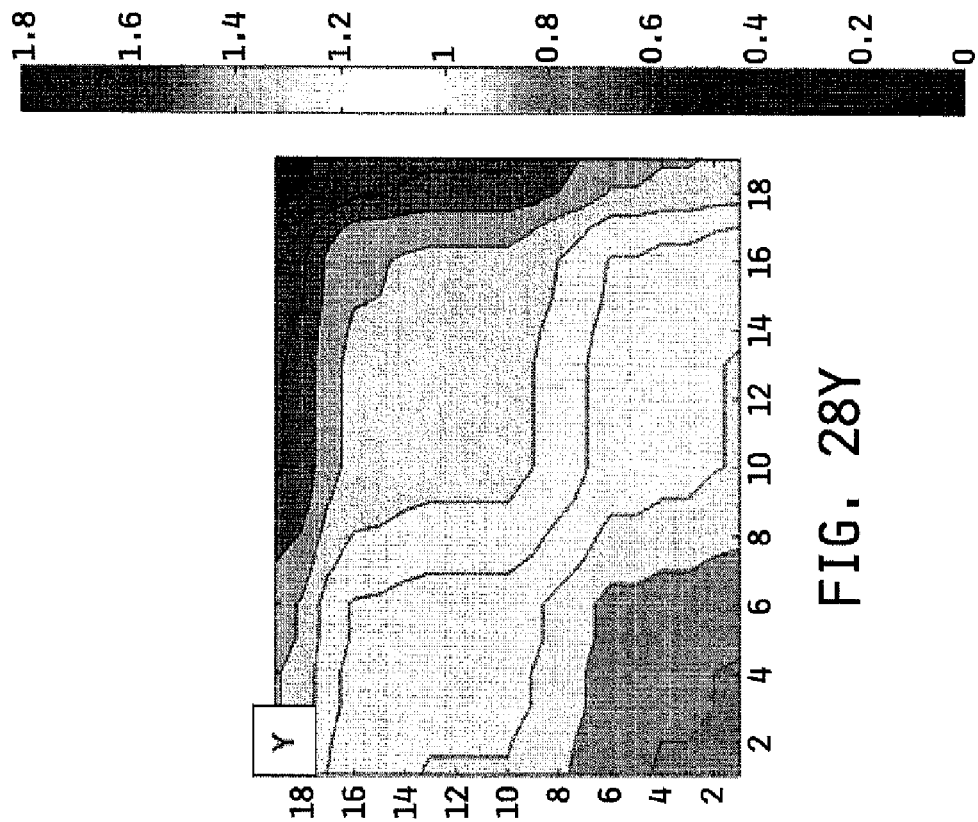
Figure 28X:
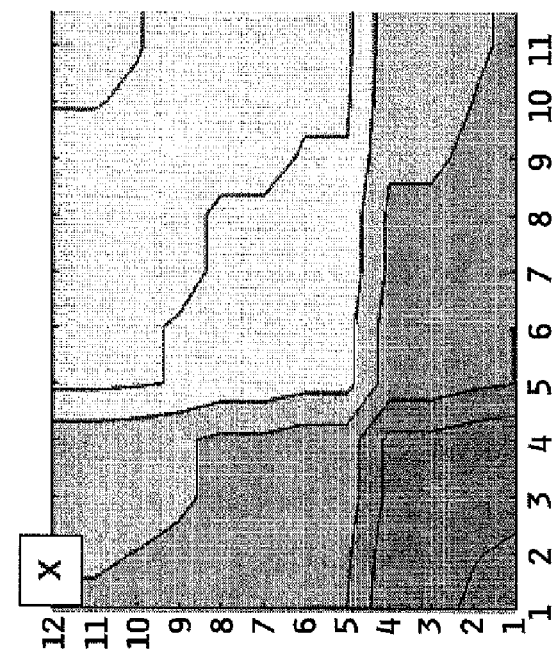
Figure 28E:
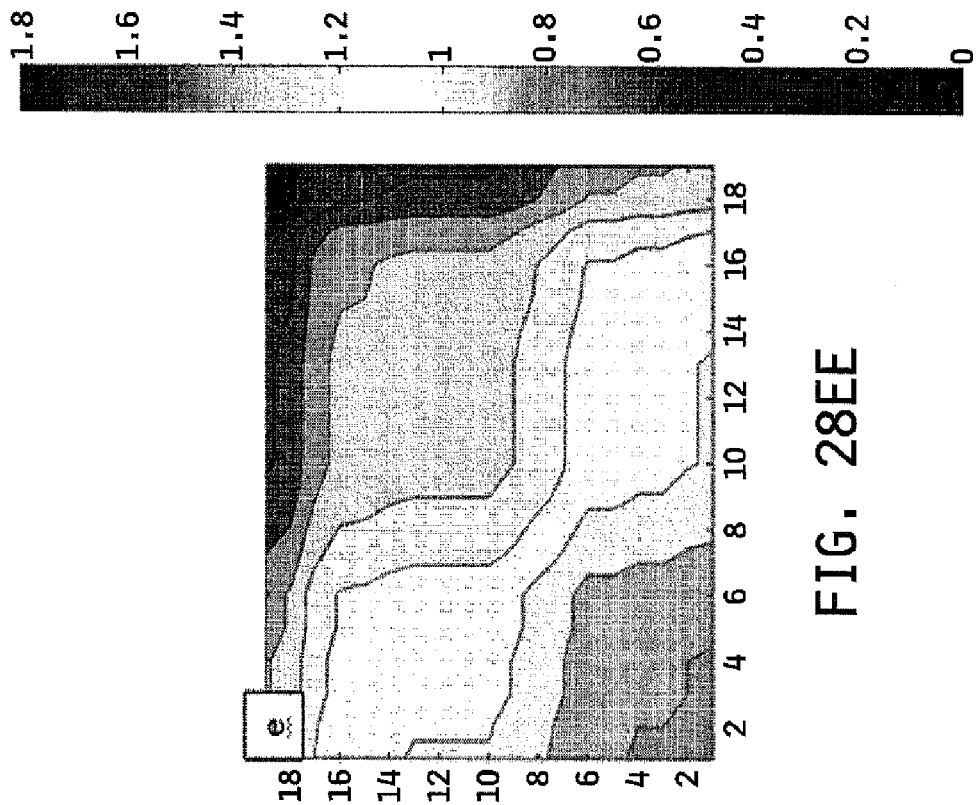

Table 7e for FIGS. 28X-28CC.

| FIG. 28 | Biological system: | Incident energy: | SOBP | RBE in the SOBP | | |
|---|---|---|---|---|---|---|
| | | | | proximal | mid | distal |
| X | Chinese hamster ovary cells. | 85 MeV | 30 mm (1 unit = 2.5 mm) | 0.94 | 1.11 | 1.16 |

-continued

| FIG. 28 | Biological system: | Incident energy: | SOBP | RBE in the SOBP | | |
|---|---|---|---|---|---|---|
| | | | | proximal | mid | distal |
| Y | Hep2 human cells | 87 MeV | 47.5 mm (1 unit = 2.5 mm) | 1.1 | 1.57 | 2.1 |
| Z | Chinese hamster V79 cells | 87 MeV | | 1.1 | 1.23 | 1.46 |
| AA | | 155 MeV | 80 mm (1 unit = 2.5 mm) | 1.2 | 1.2 | 1.28 |
| BB | Chinese hamster ovary cells. | 200 MeV | 70 mm (1 unit = 2.5 mm) | 1.24 | 1.25 | 1.32 |
| CC | | | | 1.24 | 1.24 | 1.30 |

| FIG. 28 | Biological system: | Incident energy: | SOBP | RBE in the SOBP | | |
|---|---|---|---|---|---|---|
| | | | | proximal | mid | distal |
| DD | Chinese hamster V79 cells | 200 MeV | 70 mm (1 unit = 2.5 mm) | 1.04 | 1.07 | 1.23 |
| EE | | | 80 mm (1 unit = 2.5 mm) | 1.23 | 1.25 | 1.29 |
| FF | Hep2 human cells | | | 1.1 | 1.1 | 1.89 |
| GG | Human squamous cell carcinoma SCC61 | 235 MeV | 100 mm (1 unit = 2.5 mm) | 1.1 | 1.24 | 1.24 |
| HH | V79 cells | 250 MeV | 80 mm (1 unit = 2.5 mm) | 1.23 | 1.24 | 1.24 |

Figure 28D:
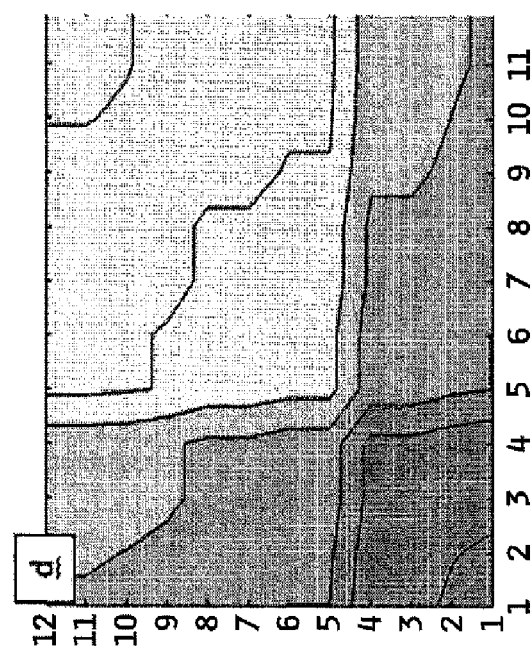
Figure 28J:
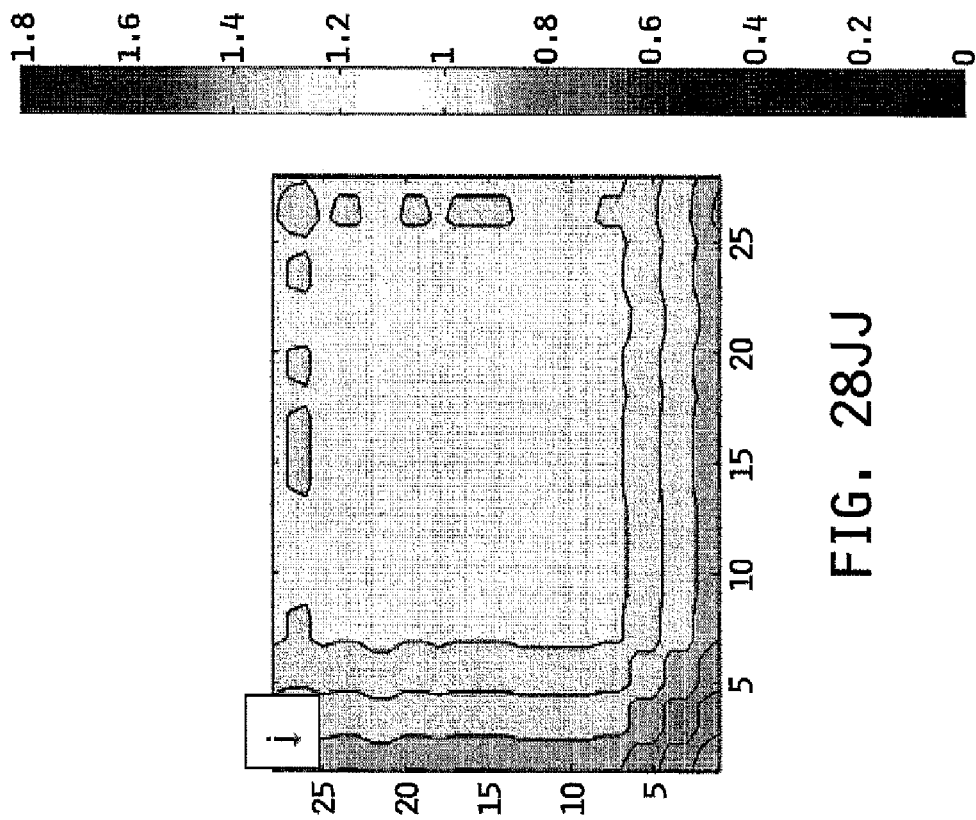
Figure 28I:
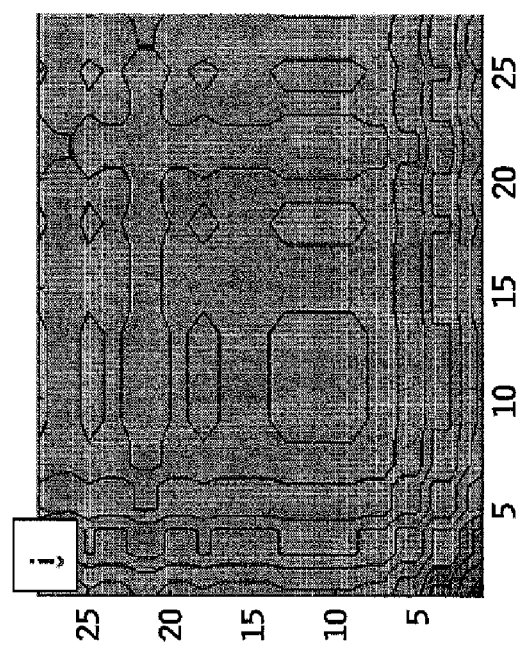

Table 7f for FIGS. 28DD-28HH.

| FIG. 28 | Biological system: | Incident energy: | SOBP | RBE in the SOBP | | |
|---|---|---|---|---|---|---|
| | | | | proximal | mid | distal |
| II | lung tolerance in mice | 200 MeV | 70 mm (1 unit = 2.5 mm) | 0.86 | 0.86 | 0.86 |
| JJ | | | | 1.02 | 1.02 | 1.02 |
| KK | | | | 1.55 | 1.55 | 1.55 |
| LL | Intest. Crypt reg. in mice | | | 1.23 | 1.15 | 1.26 |
| MM | | | | 1.1 | 1.14 | 1.26 |

Table 7g for FIGS. 28JJ-28MM.

The application of $W_{RBE \neq 1.1}$ can result in unwanted hot spots or cold spots in the dose distribution within the target, or a dose distribution leading to suboptimal target coverage or excessive dose to healthy tissue. There are some significant differences between the clinically applied $W_{RBE=1.1}$ dose distributions and the dose distributions that would be derived from the empirically determined $W_{RBE}$ values. Many studies indicated RBE values greater than 1.4 for human tumor cells, although lower values were reported by other groups. This variation among reported values and between values derived from in vitro studies and in vivo studies represents an unsafe uncertainty in the biological dose that is being delivered clinically.

If the $W_{RBE}$ described by Britten et al. for an 87 MeV incident proton beam modulated to 4.7 cm SOBP were applied to a human tumor treatment plan, then the isodose distribution profiles for a variety of coplanar beam arrangements show excessive dose over the PTV compared with the $W_{RBE=1.1}$ distribution profiles (see FIGS. 11, 12, 15, 16, 19, 20, 21, 28L, 28T). The increase in biological dose depends on the number of proton beams and the angles between them because the increased $W_{RBE}$ occurs not only at the distal fall-off but also along the SOBP. The isodose profile figures presented herein show that the increase in $W_{RBE}$ can result in hot spots of up to 100% (twice) the prescribed dose for two beams with 45° between them (see FIG. 12), about 80% for three beams with 45° between them (see FIG. 19), about 60% for two beams with 90° between them (FIG. 11), four beams with 45° between them (FIG. 20) and four beams with 0°, 180°, 270° and 315° (FIG. 21).

Other configurations result in about 40% increase over the clinical standard (see FIGS. 13, 14, 17, 18, 22, 23, 24, 25, 26 and 27). In one embodiment of a treatment planning method, where a maximum increase in biological dose of 25% greater than the dose determined using the standard $W_{RBE=1.1}$ is clinically acceptable, then all distribution profiles resulting in higher biological dose should be disallowed.

Table 8 provides a sorting of the results for the two beam box examples in FIG. 28 where potential clinical outcomes are ascribed to the increases or decreases in biological dose over the prescribed values. The effect of $W_{RBE}$ value was examined.

TABLE 8

Potential treatment safety evaluation. Analyzing the results for the two beam box examples in FIG. 28. Safe indicates delivered dose within 25% of prescribed dose. Detrimental indicates dose 26%-50% above prescribed dose. Potentially lethal indicates dose 51%-75% above prescribed dose. Lethal indicates dose in excess of 76% above prescribed dose or a hotspot outside of the PTV. Letters represent figure panels of FIG. 28.

| Safe | SOBP (mm) | $E_o$(MeV) | Detrimental | SOBP (mm) | $E_o$(MeV) | Potentially lethal | SOBP (mm) | $E_o$(MeV) | Lethal | SOBP (mm) | $E_o$(MeV) |
|---|---|---|---|---|---|---|---|---|---|---|---|
| A | 12 | 65 | G | 17 | 65 | L | 20 | 67 | C | 15 | 65 |
| B | | | T | 20 | 70 | | | | D | | |
| H | 17 | | U | | | | | | E | | |
| I | | | Z | 47.5 | 87 | | | | F | | |
| J | | | f | 80 | 200 | | | | Y | 47.5 | 87 |
| K | | | k | | | | | | e | 80 | 200 |
| M | 20 | 67 | | | | | | | | | |
| N | | | | | | | | | | | |
| O | | | | | | | | | | | |
| P | | | | | | | | | | | |
| Q | | | | | | | | | | | |
| R | | | | | | | | | | | |
| S | | | | | | | | | | | |
| V | 5 | 85 | | | | | | | | | |
| W | | | | | | | | | | | |
| X | 30 | | | | | | | | | | |

TABLE 8-continued

Potential treatment safety evaluation. Analyzing the results for the two beam box examples in FIG. 28. Safe indicates delivered dose within 25% of prescribed dose. Detrimental indicates dose 26%-50% above prescribed dose. Potentially lethal indicates dose 51%-75% above prescribed dose. Lethal indicates dose in excess of 76% above prescribed dose or a hotspot outside of the PTV. Letters represent figure panels of FIG. 28.

| Safe | SOBP (mm) | $E_o$(MeV) | Detrimental | SOBP (mm) | $E_o$(MeV) | Potentially lethal | SOBP (mm) | $E_o$(MeV) | Lethal | SOBP (mm) | $E_o$(MeV) |
|---|---|---|---|---|---|---|---|---|---|---|---|
| a | 80 | 155 | | | | | | | | | |
| b | 70 | 200 | | | | | | | | | |
| c | | | | | | | | | | | |
| d | | | | | | | | | | | |
| g | 100 | 235 | | | | | | | | | |
| h | 80 | 250 | | | | | | | | | |
| i | 70 | 200 | | | | | | | | | |
| j | | | | | | | | | | | |
| l | | | | | | | | | | | |
| m | | | | | | | | | | | |

TABLE 9

Potential treatment safety evaluation. Analyzing the results using the data of Britten et al. [25] for a 4.7 cm SOBP, incident energy 87 MeV. Safe indicates delivered dose within 25% of prescribed dose. Detrimental indicates dose 26%-50% above prescribed dose. Potentially lethal indicates dose 51%-75% above prescribed dose. Lethal indicates dose in excess of 76% above prescribed dose or a hotspot outside of the PTV.

Figure 15A:
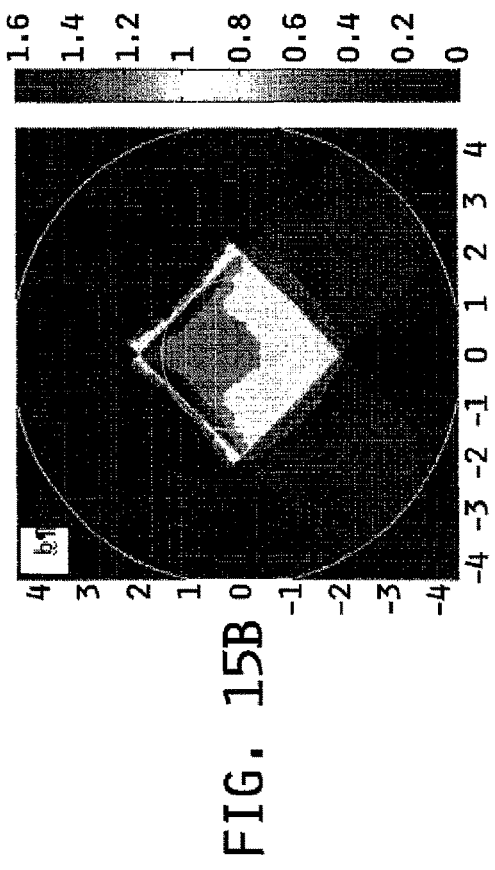
FIGS. 15A-15C show an isodose distribution profile of two proton beams with 225° and 315° and incident energy of 87 MeV.
Figure 15B:
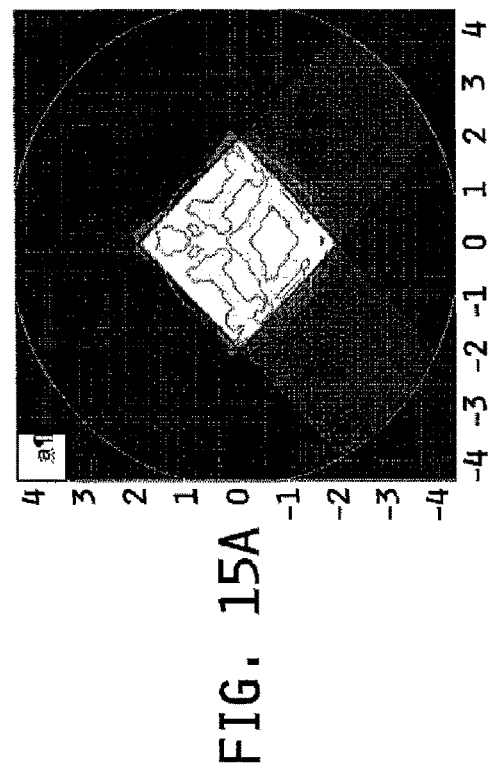
Figure 15C:
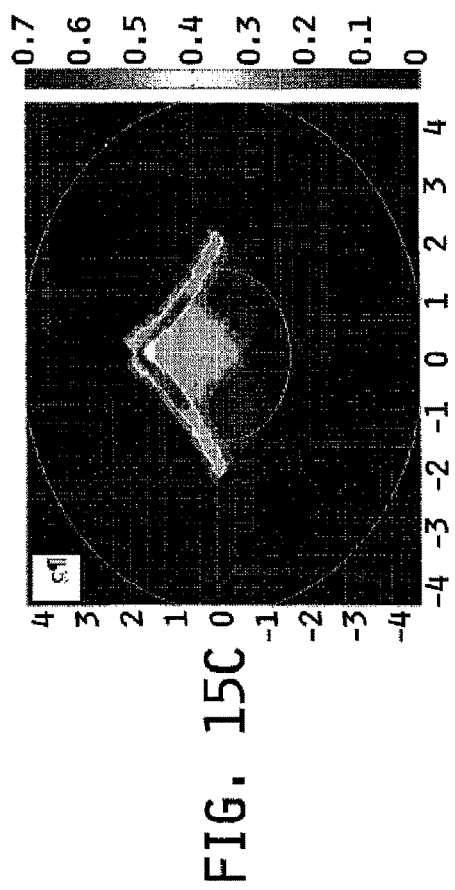
Figure 19A:
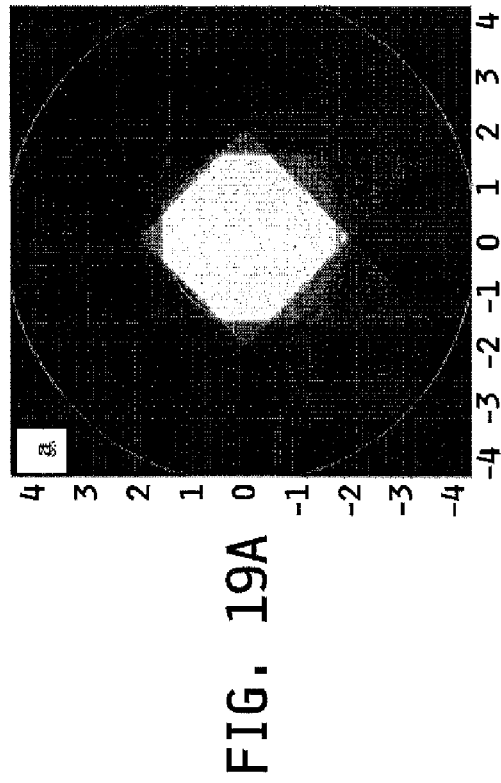
Figure 19C:
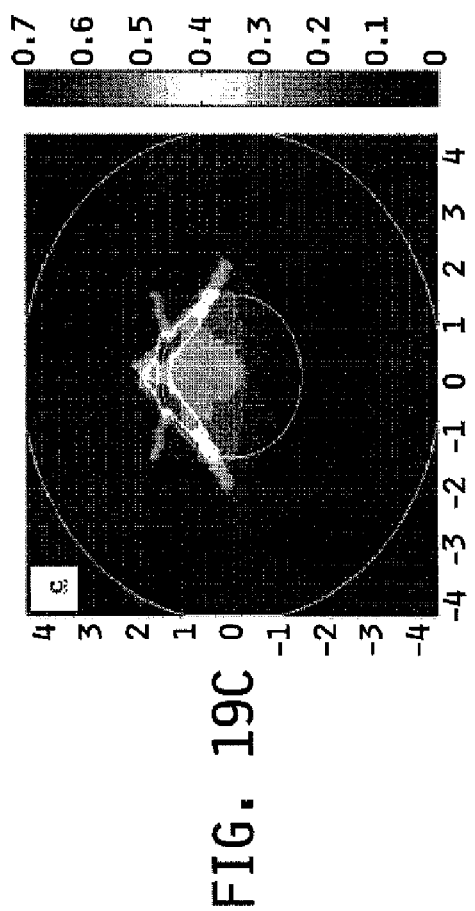
Figure 20C:
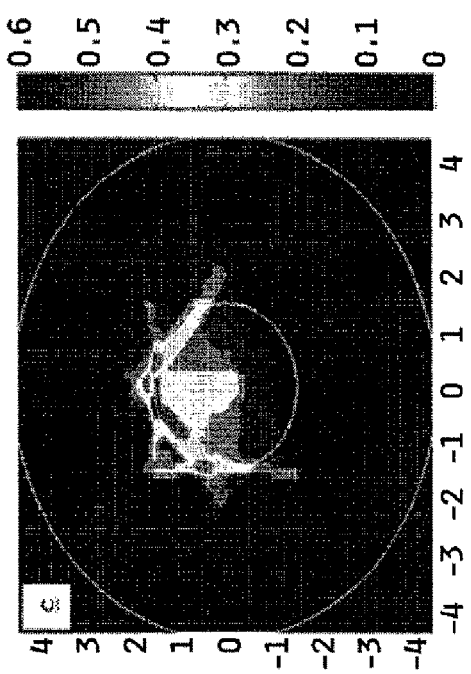

| Safe | Detrimental | Potentially lethal | Lethal |
|---|---|---|---|
| FIGS. 13A-13C | FIGS. 11A-11C | FIGS. 12A-12C |
| FIGS. 14A-14C | FIGS. 15A-15C | FIGS. 16A-16C |
| FIGS. 17A-17C | FIGS. 20A-20C | FIGS. 19A-19C |
| FIGS. 18A-18C | FIGS. 21A-21C | |
| FIGS. 22A-22C | | |
| FIGS. 23A-23C | | |
| FIGS. 24A-24C | | |
| FIGS. 25A-25C | | |
| FIGS. 26A-26C | | |
| FIGS. 27A-27C | | |

In some embodiments of the present disclosure, the effect of beam configuration was examined. In general, the optimal distribution appeared to use five or six beams where the increased dose spread out relatively evenly inside the PTV and the increase in dose was approximately 40%. The more dangerous distribution appeared when two and three beams isodose profiles were created with 45° between beams since the hot spot concentrates in relatively small areas inside the PTV with a dose increase of up to 80%-100%.

A hot spot aligned with a particularly susceptible tissue mass may result in higher risk. In other embodiments, a relatively small hot spot may not be as dangerous as a larger hot spot.

Data disclosed herein suggest that there may be significant dose delivered outside of the PTV due to the extension of biological dose beyond the distal fall-off. This increase in biological dose beyond the PTV is dependent upon the angle between beams and the number of beams used to construct the distribution profile increasing the dose to healthy tissue between 20% to 40% greater than dose obtained using $W_{RBE=1.1}$.

Because of the increase in biological dose of proton radiation, particularly at the distal edge of the SOBP, the DDF should not be positioned within radiation sensitive tissues. Mitigation could be accomplished by slightly reducing the incident beam energy, which pulls the end-of-range back from the edge of the PTV, or by adjusting the number and configuration of the beams so as to avoid hot spots such as those observed in the case of 45° juxtaposed beams. The distal fall-off could also be smeared out, by feathering the delivery of the multi-fractional protocol. With this protocol, the initial energy of beams contributing to hotspots is varied over time to produce an averaging of the dose distribution at critical locations. This reduces both the dose and average RBE over the terminal few millimeters of the SOBP. Patient setup and organ motion during treatment may also contribute to this smearing effect and might responsible for preventing the potential dire patient outcomes that might be predicted by the results presented herein.

An administrative mitigation technique might also be employed. The clinic could impose a risk assessment and mitigation protocol that requires the development of at least two treatment plans for each patient: one using the standard of practice $W_{RBE=1.1}$, and one using a biologically driven worst case scenario set of $W_{RBE}$ values obtained from the literature. Beam configurations could then be displayed and evaluated, considering the potential for damage as indicated in Tables 8 and 9. Configurations deemed potentially dangerous could be discarded. Use of this technique allows evaluation of the clinical standard through visualization of biologically based treatment planning without risking implementation of an untested biological algorithm. The delivered treatment plan can reflect standard practices while being evaluated for potential risk.

In some embodiments, a "DICOM" tool is used to implement safer delivery of proton beam treatment corrected for relative biological effectiveness. DICOM is an acronym for "Digital Imaging and Communications in Medicine," which is a standard for handling, storing, printing, and transmitting information in medical imaging. This includes a file format definition and a network communications protocol, known in the art. Such a DICOM tool could optionally include real-time visualization of biological hot spots for a proton beam therapy treatment operator, and real time warnings or alarms for existence of such hot spots. Optionally, a DICOM tool would include a memory and software for calculating in real time the likelihood of the existence of biological hot spots based on number of beams, beam angle, tissue being treated, region of body being treated, energy intensity of the beam, and/or organ at risk.

In one embodiment, such a DICOM tool will maintain a plan with beams using Gy (RBE=1.1), a computer then visually demonstrates in a color wash in 3 dimensions a color plot showing biological hot spots or likely biological hot spots, evaluate beam selection, use range modulation methods and replanning to avoid biological hot spots, and implement the new treatment plan, optionally at the direction of a physician.

In other embodiments, a user could set a goal of range of RBE allowed for treatment plan acceptance (for example 5% variability overall), then the planning system could automatically change the beam selection to make beams be "range modified." Such modification could be made quickly or aggressively during a PBT procedure. The net result may cause beams to have very different dose shapes than they do today as physical dose will no longer be "level/homogeneous" going forward.

Figure 29:
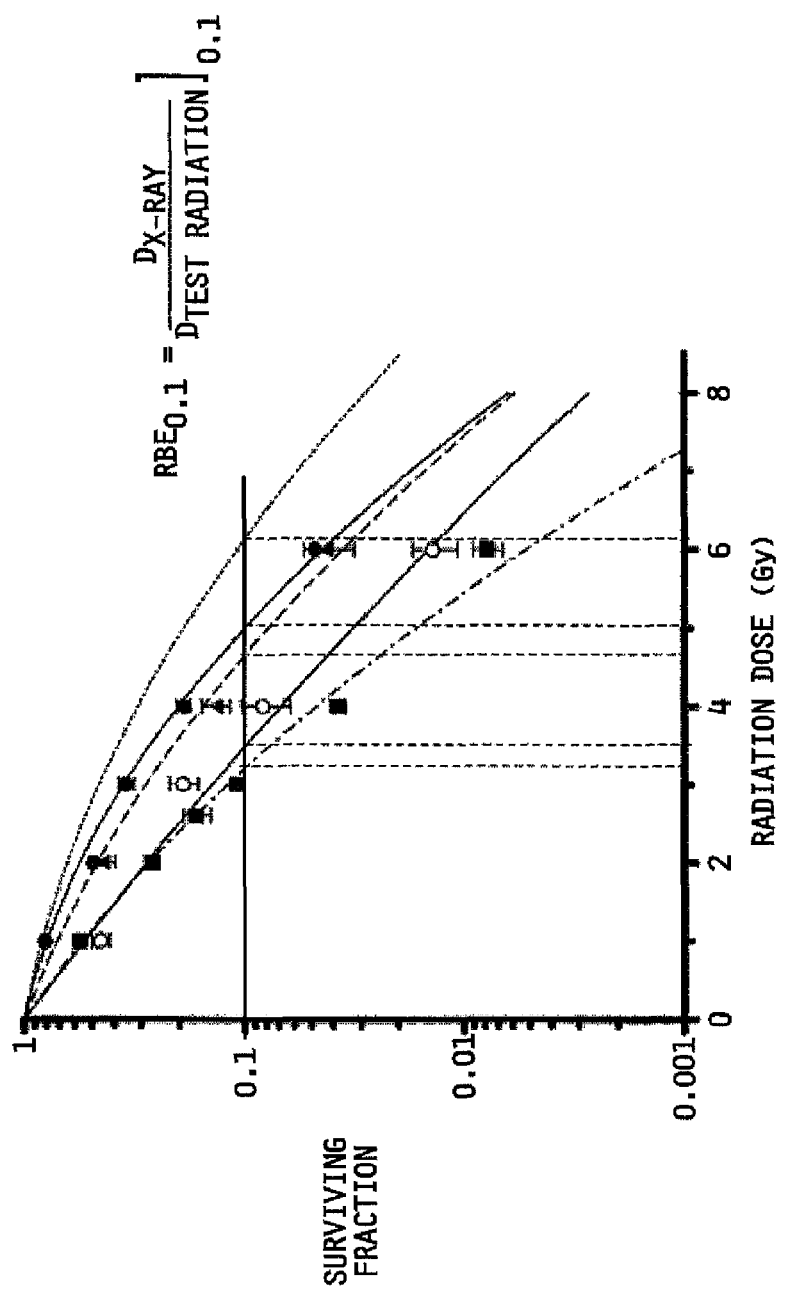
FIG. 29 shows a cell survival curve.

Referring now to FIG. 29, a cell survival curve is shown. FIG. 29 demonstrates the calculation of RBE from an in vitro experiment. To measure the RBE of a radiation, cell survival curves are constructed and compared. FIG. 2 specifically shows calculation of RBE of Hep2 human tumor cells where the test radiation is 87 MeV of proton beam at different depths of SOBP 33.9 mm (solid circles), 53.9 mm (triangles), 58.6 mm (open circles), and 60.9 mm (squares). The X-ray survival curve is represented by dashed line with no symbols. Cells are exposed to escalating doses of reference radiation (e.g. x-ray) or are irradiated by the same doses of test radiation. The number of surviving cells of each dose is scored. In FIG. 29, Hep2 cells were exposed to x-ray radiation (dashed line) or proton radiation at four depths within a solid water phantom 33.9 mm, 53.9 mm, 58.6 mm, and 60.9 mm.

To obtain the equivalent biological dose ($D_{bio}$) from the prescribed physical dose($D_{phys}$), the following relationship is used:

$$D_{bio} = RBE \times D_{phys} \quad (2a)$$

Radiation with a LET of about 100 keV/μm is optimal in terms of producing a biologic effect because the ionization density at this LET has the highest probability of causing a double-strand break (DSB) by the passage of a single charged particle. As LET increases beyond 100 keV/μm there will be additional ionization events. However once lethal DNA damage has occurred to a cell no additional biological damage can be measured. An increase of the atomic number of the radiation particles leads to decrease the RBE maximum and shifts to bigger LET values.

There are three categories of computerized dose calculation algorithms for treatment planning: correction based, model based and direct Monte Carlo. Correction-based algorithms depend on measured data that are obtained in a cubic water phantom. These algorithms interpolate measured depth dose data and specially formulated analytic functions relate to the various correction factors under particular conditions.

The model-based and direct Monte Carlo algorithms more accurately predict dose distribution of photons and charge particles. These algorithms have ability to simulate radiation transport in three dimensions. The dose distribution is calculated by accumulating ionizing events in voxels that give rise to energy deposition in the medium. However, these algorithms require computational time and are not currently practical for clinical use. External beam cancer treatment usually requires two or more fields to achieve an acceptable dose distribution over the area of interest [4].

Figure 30:
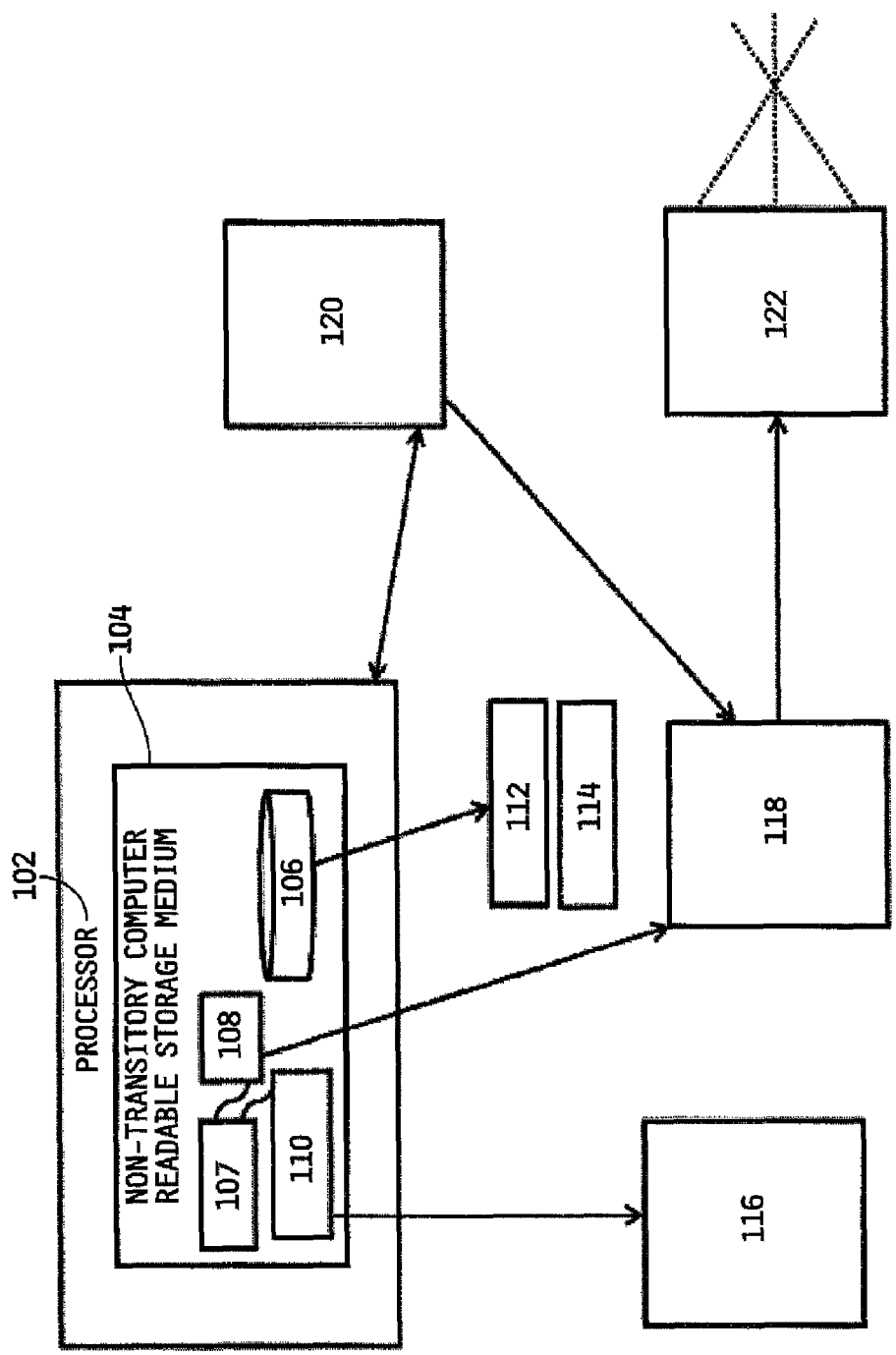
FIG. 30 is a block diagram representing one embodiment of a system of treatment for beam therapy according to the present disclosure.

Referring now to FIG. 30, a block diagram representing one embodiment of a system of treatment for beam therapy according to the present disclosure is shown. According to various embodiments, a processor may be in electrical communication with a tangible, non-transitory memory or storage medium. In various embodiments, the processor may be in electrical communication with a beam applicator. As used herein, the term "electrical communication" includes both wired and wireless communication (e.g., IR wireless communication, satellite communication, broadcast radio, Microwave radio, Bluetooth, etc.). In various embodiments the processor may be separate from the beam applicator or, in some embodiments, may form part of the beam applicator. FIG. 30 illustrates a processor 102 that includes a non-transitory computer readable storage medium (e.g., a non-transitory memory) 104, database 106, hot spot application 107, beam control application 108 and image display application 110. In the exemplary embodiment, database 106 includes RBE rules 112 and images 114. In some embodiments, hot spot application 107 calculates potential biological hotspots using Excel, MATLAB, or any other acceptable software based on beam characteristics, such as energy, incident angle, number of beams, tissue sensitivity, organs-at-risk, etc. The existence and location of potential hot spots is transferable between hot spot application 107, beam control application 108, and image display application 110.

In some embodiments, RBE rules 112 provide logic for beam control application 108, such as for example, if the RBE value is greater than 5% above the prescribed physical dose, beam control application 108 could change output provided to beam controls 118. Images 114 can include any images from prior or current surgeries for display 116. Therefore, image display application 110 can display on display 116 images of potential hot spots in a current procedure, real-time images of hot spots during a procedure, similar hot spots from past procedures, and the prescribed naïve or physical dose. Image display application 110 can also provide to image display 116 images representing the difference between the naïve or physical dose in a beam treatment plan and the RBE value. In some embodiments, image display application 110 can display images similar to FIGS. 5-28.

Beam controls 118 can accept commands from beam control application 108, or from user controls 120. For example, based on RBE rules 112 and hot spot application 107, if a biological hot spot is likely to be created in a patient's tissue, beam controls 118 could modify the number of beams, energy intensity of the beams, the beam's angle relative a second beam, the application duration of the beam, or any other characteristic known in the art, to reduce the likelihood of biological hot spots. In this way, beam controls 118 control beam applicator 122, which in some embodiments is a proton beam for proton beam therapy (dotted lines showing 3 beams; however, in other embodiments more or fewer beams could be used).

Alternatively, user controls 120 can provide commands for beam controls 118, for example, if a doctor observed a potential biological hot spot on visual display 116, but the RBE rules did not recognize a need to change treatment based on the RBE value, the doctor or user could enter commands into user controls 120 so that beam controls 118 would change beams, energy intensity of the beams, the beam's angle relative to a second beam, the application duration of the beam, or any other characteristic known in the art, to reduce the likelihood of biological hot spots. In this way, beam controls 118 control beam applicator 122, which in some embodiments is a proton beam for proton beam therapy.

Figure 31:
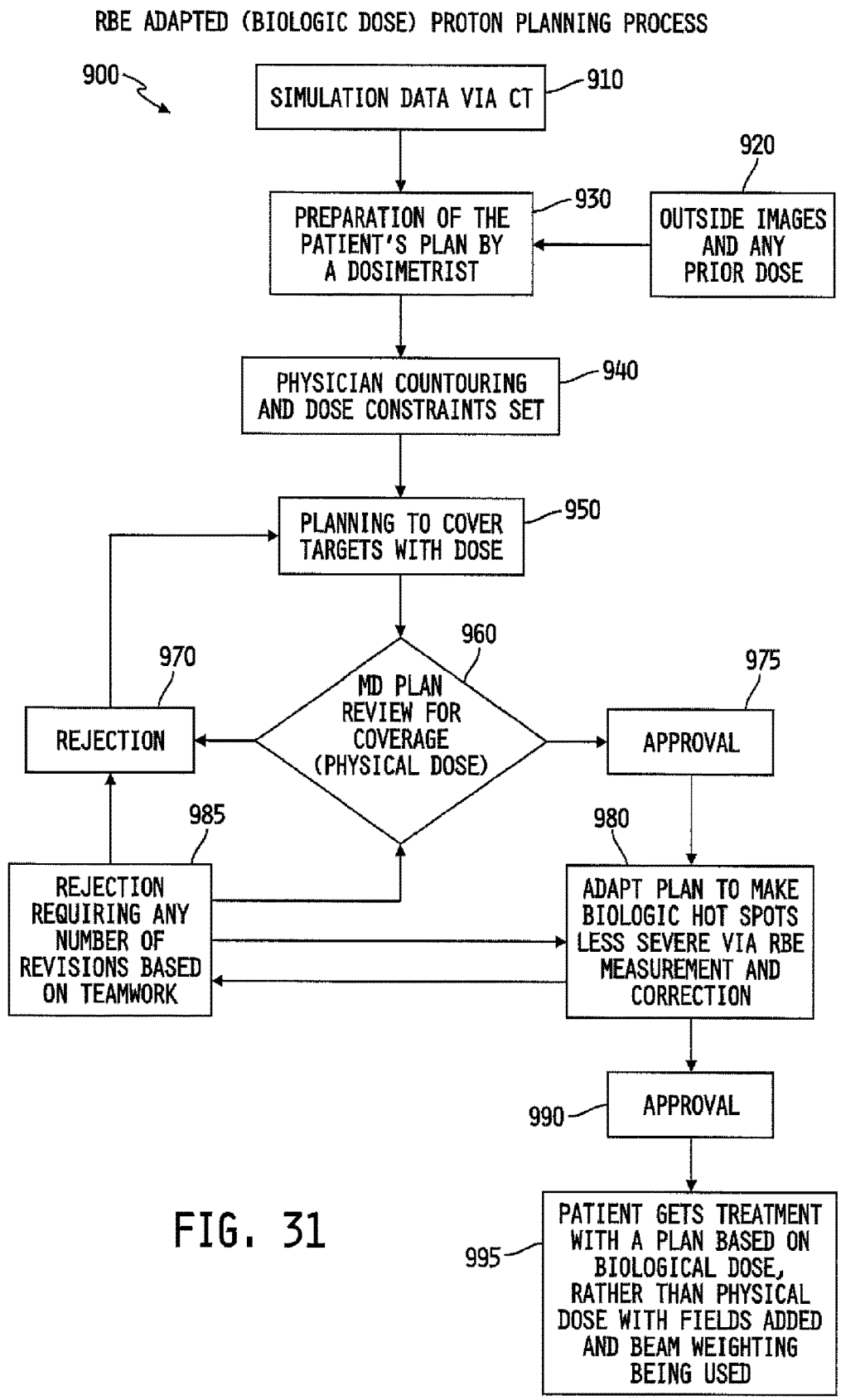
FIG. 31 is a block diagram representing one embodiment of the steps involved in a planning and treatment method based on biological dose, rather than physical dose, of the present disclosure.

FIG. 31 is a block diagram representing one embodiment of the steps involved in a planning and treatment method based on biological dose, rather than physical dose, of the present disclosure. In some embodiments, method 900, which is exemplified in FIG. 31 can be carried out by the system displayed in FIG. 30, optionally with a physician or team of physicians. For example, processor 102 including non-transitory computer readable storage medium 104, database 106, hot spot application 107, beam control application 108 and image display application 110 could be used to apply certain steps displayed in FIG. 31, such as preparation of the patient's plan by a dosimetrist. RBE rules 112, beam controls 118, and beam applicator 122 could be used to carry out the step in FIG. 31 wherein the patient gets treatment with a plan based on biological dose, rather than physical dose, with fields added and beam weighting being used by beam controls 118 and beam applicator 122.

With continued reference to FIG. 31, FIG. 31 illustrates method 900, which in various embodiments may be an RBE Adapted (Biologic Dose) Proton Planning Process. Method 900 includes simulation of data via CT (step 910) and also preparation of the patient's plan by a dosimetrist (step 930). In various embodiments, preparation of the patient's plan by a dosimetrist (step 930) may include the use of outside images and any prior dose information (step 920). In various embodiments, method 900 may also include setting dose constraints and physician contouring (step 940) and planning to cover targets with a dose (step 950). Then, the medical doctor may review the plan for coverage (step 960). The plan can then be approved (step 975) or rejected (step 970). If the plan is rejected, step 950 may be repeated. Once the review for coverage (step 960) is approved (step 975), the plan may be adapted to make biologic hot spots less severe via RBE measurement and correction (step 980) the adaptation may be rejected (step 985) or may be approved (990). Once approval is received (step 990), the patient may receive treatment with a plan based on a biological dose, rather than a physical dose (step 995). In some embodiments, the patient may receive treatment with a plan based on a biological dose with fields added and/or the use beam weighting.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

EXAMPLES

Example 1—In Use with Patient

A patient plan was selected to serve as an example for direct comparison of image-guided radiotherapy plans using non-range modulation PBT ("NRMPBT"), and range-modulation PBT ("RMPBT"). An additional plan using RMPBT was created to represent a re-treatment scenario ("RMPB-Trt") using a vertex beam. Planning statistics regarding dose, volume of the planning targets, and color images of the plans are shown in FIGS. 5-8. The three plans generated for this patient revealed that in all cases dosimetric and device manufacturing advantages are able to be achieved using RMPBT.

Organ at risk ("OAR") doses to critical structures such as the cochleae, optic apparatus, hypothalamus, and temporal lobes can be selectively spared using this method. Concerns about the location of the RBE that did significantly impact beam selection and treatment planning no longer have the same impact on the process, allowing these structures to be spared dose and subsequent associated issues.

This example illustrated that RMPBT can improve OAR sparing while giving equivalent coverage to target volumes relative to traditional PBT methods while avoiding the increased RBE at the end of the beam. It has proven to be both robust and easy to design and implement in certain planning process. The method underscores the need to optimize treatment plans in PBT for both traditional energy dose in gray (Gy) and biologic dose (RBE).

The "range mod" technique was illustrated with evaluation of a retreatment patient plan treated with PBT. This patient had recurrent ependymoma in the posterior fossa. Treatment plans were constructed using three dimensional conformal radiation therapy ("3DCRT"), intensity modulated radiation therapy ("IMRT"), non-range modulation proton beam therapy ("NRMPBT"), and range modulation proton beam therapy ("RMPBT") techniques. (see FIGS. 5-8). The range modulation plan employed end of range modification of 3 mm, thus avoiding complete transmission through any OAR. In the exemplified plans, two range-modulated fields per beam angle were used.

Xio 6.0 treatment planning software (Elekta AB, Sweden) was used for all cases presented for PBT planning. Active scanning [17,18] was employed for the delivery of the SOBP's using apertures and compensators manufactured by IU Health Cyclotron Operations ("IUCO"). The uniform active scanning process required the use of apertures to shape the beam edge and compensators to shape the beam end via direct range compensation, as a sum these pieces of equipment are called patient specific devices ("PSD's"). Aperture devices were machined out of medical grade brass while compensators were machined from medical grade Lucite using standard procedures; U.S. Food and Drug Administration (FDA) requisite quality assurance was performed. All beam outputs and devices were checked for accuracy before treatment delivery per routine. E Each treatment position's verification images were reviewed by a physician for every fraction in real time either at the gantry or via remote viewing monitor prior to delivering beam.

The DICOM RT data set from the patient's plan computed on XiO was recovered and imported in the Eclipse 10 (Varian Medical Systems, USA) for side-by-side comparison use. All photon plans were constructed within Eclipse 10. The deployed plan was compared to chart data prior to de-identification in order to confirm the correct recovery of the data and then doses to all contoured structures were converted into percentage format for comparison.

The patient had been previously treated to 54 Gy via coplanar IMRT and relapsed in field. The patient received RMPBT in order to avoid OAR's, and at approximately 2 years from the procedure was doing well without evidence of radiation damage or other local toxicity.

Example 2—Modeling Data and Matrix Development

Microsoft Excel 2013 was used to develop a matrix. Each column of the matrix listed the length for the transverse section of the treatment object and each row listed the width for the transverse section. Each element in the matrix represented the value of the fractional dose taken from the digital data of the dose-depth profile.

The transverse section of the treatment object was assumed to be a 9 cm diameter circle and the Planning Target Volume (PTV) was a concentric circle with a 3 cm diameter. Thus, the matrix of transverse section was 89 mm×89 mm. The width of the model proton beam was 30 mm built within the matrix with the planned orientation. The matrix was filled manually taking into account the angle of the beam.

The matrixes of 0°, 90°, 180°, 225°, 270° and 315° for $W_{RBE=1.1}$ SOBP and $W_{RBE=ref[25]}$. Each matrix represented the transverse section size with different beam angles. There were 12 matrixes that were named old0, new0, old45, new45, old90, new90, old135, new135, old180, new180, old270 and new270. 'Old' signified $W_{RBE=1.1}$ and 'new' signified $W_{RBE=ref[25]}$. The number behind the word 'old or new' indicated the angle of the beam.

The new matrix of isodose distribution was formed by beams of different angles. The total to each cell of the matrix was achieved by summing the contribution from each beam. The data was then normalized to 100% at maximum dose. MATLAB was normalized and the matrixes of different beams added as follows:

For two beams (A and B) $W_{RBE=1.1}$ was named 'old', the experimentally derived value of RBE $W_{RBE=ref[25]}$ is named 'new'. The following code was written in MATLAB:

```
EDU<<oldAandB=(oldA/2)+(oldB/2);

EDU<<newAandB=(newA/2)+(newB/2);
```

To obtain the matrix of the difference of isodose distribution between the $W_{RBE=ref[25]}$ and $W_{RBE=1.1}$ (diffON) for two matrix beams, the following code was written in Matlab:

```
EDU<<diffONAandB=(newAandB)-(oldAandB);
```

For N beams (A, B, and N). The following code was written in Matlab:

```
EDU>>oldAandBand . . . andN=(oldA/N)+
    (oldB/N)+ . . . +(oldN/N);

EDU>>newAandBand . . . andN=(newA/N)+(newB/
    N)+ . . . +(newN/N)
```

To obtain the matrix of the difference of isodose distribution between the $W_{RBE=ref[25]}$ and $W_{RBE=1.1}$ (diffON) for N matrix beams, the following code was written in Matlab:

```
EDU>>diffONAandBand . . . andN=(newAand
    Band . . . andN)-(oldAandBand . . . andN);
```

The circle that represents the transverse section can be drawn by the following matlab code:

```
EDU>>t=linspace(0,2*pi,10000);

EDU>>h=0;

EDU>>k=0;

EDU>>r=4.5;

EDU>>x=r*cos(t)+h;

EDU>>y=r*sin(t)+k;

EDU>>plot(x,y,'white')
```

Then the circle that represents the PTV can be drawn by the following MATLAB code:

```
EDU>>t=linspace(0,2*pi,10000);

EDU>>h=0;

EDU>>k=0;

EDU>>R=1.5;

EDU>>X=R*cos(t)+h;

EDU>>Y=R*sin(t)+k;

EDU>>plot(X,Y,'white')
```

The isodose distribution for the $W_{RBE=1.1}$ matrix, which begins with 'old', $W_{RBE=ref[25]}$ matrix, which begins with 'new', or the matrix of the difference of isodose distribution, which begins with (diffON) can be done by the following MATLAB code:

```
EDU>>[w,l]=meshgrid(-4.4:0.1:4.4,-4.4:0.1:4.4);

EDU>>[s,f]=contourf(w,l,old'new' or 'diffON');

EDU>>set(f,'lineColor','none')
```

To install the object circle, target circle and isodose distribution gathering, the first line of MATLAB command window should be written "hold on" then the isodose distribution has done. After that the object or the target circle have been drawn and the last line should be written "hold off".

After the image of isodose distribution is captured, the "colorbar" is selected from the "Insert" on the command bar. To change the isodose distribution weight, the "Property Editor" under "View" on the commend bar of the "figure windows" is used.

Obtaining the isodose distribution profile for four beams at 0°, 90°, 180° and 270° can be done by uploading the matrices of these beams, the codes of the basic matrices and the summing matrices of the different angle beam were applied as follows:

```
EDU>>load('matlab1Human.mat')

EDU>>t=linspace(0,2*pi,10000);

EDU>>h=0;

EDU>>k=0;

EDU>>r=4.5;

EDU>>x=r*cos(t)+h;

EDU>>y=r*sin(t)+k;

EDU>>R=1.5;

EDU>>X=R*cos(t)+h;

EDU>>Y=R*sin(t)+k;

EDU>>old0and90and180and270=(old0/4)+(old90/
    4)+(old180/4)+(old270/4);

EDU>>new0and90and180and270=(new0/4)+(new90/
    4)+(new180/4)+(new270/4)

EDU>>diffON0and90and180and270=
    (new0and90and180and270)-
    (old0and90and180and270);

EDU>>[w,l]=meshgrid(-4.4:0.1:4.4,-4.4:0.1:4.4);
```

% The codes of isodose profile of $$D_{RBE}\left(RBE = 1.1, \frac{\alpha}{\beta} = 3.76\right)$$

is applied as follows: %

```
EDU>>hold on

EDU>>[s,f]=contourf(w,l,old0and90and180and270);
```

```
EDU>>set(f,'lineColor','none')

EDU>>plot(x,y,'white')

EDU>>plot(X,Y,'white')

EDU>>hold of
```
% The codes of isodose profile with $W_{RBE}$ is applied as follows: %
```
EDU>>hold on EDU>>[s,f]=contourf(w,l,new0and90and180and270);

EDU>>set(f,'lineColor','none')

EDU>>plot(x,y,'white')

EDU>>plot(X,Y,'white')

EDU>>hold of
```
% The codes of the difference between the isodose profiles is applied as follows: %
```
EDU>>hold on EDU>>[s,f]=contourf(w,l,
    diffON0and90and180and270);

EDU>>set(f,'lineColor','none')

EDU>>plot(x,y,'white')

EDU>>plot(X,Y,'white')

EDU>>hold of
```
Then each figure was saved as a JPEG image.

Example 3—Rescaling the Depth-Dose Profile for the Assumed PTV

SOBP depends on the tumor size. As the SOBP decreases, the entrance percentage dose will decrease and all values of dose beyond that will decrease as well up to the SOBP region. Also the mid-point will change when the SOPB changes. So it is necessary to rescale the entrance doses and the position $W_{RBE=ref[25]}$ values. The SOBP of FIG. 9 is about 46 mm but the Planning Target Volume (PTV) is 30 mm in diameter. The entrance dose of the 87 MeV monoenergetic proton beam is at about 0.18 of the maximum dose.

The entrance relative dose of a 30 mm SOBP, using Equation 3, will be 0.606779 and the new positions of $W_{RBE=ref[25]}$ can be obtained by Equation 4 shown in Table 9.

$$Y\% \text{ dose} = \frac{0.82 \times \text{the length of } SOPB(\text{cm}) \text{ of interest}}{5.9} + 0.18 \quad (3)$$

$$X2 \text{ cm} = \quad (4)$$
$$\frac{X \text{ cm} \times (\text{the point position on the Original } SOBP - 1.4)}{4.5} + X1$$

TABLE 9

Rescaling the position of RBE in water equivalent depth (WED) with incident energy of 87 MeV 30 mm SOBP for Hep2 cells using Equation 4.

| Incident energy (MeV) | WED (mm) | RBE |
|---|---|---|
| 87 | 44.2267 | 1.46 |
| 87 | 55.6 | 1.57 |
| 87 | 58.933 | 2.1 |
| 87 | 60.9 | 2.3 |

The relative dose with $W_{RBE=ref[25]}$ and rescaled positions of incident energy of 87 MeV for the Hep2 Human cells are obtained from Table 9 and Equation 2b as shown in Table 10.

TABLE 10

3.0 cm SOBP physical relative dose profile with $W_{RBE-ref[25]}$ (Relative $D_{RBE-ref[25]}$) and incident energy of 87 MeV for the Hep2 Human cells.

| Depth(cm) | Relative $D_{RBE-ref[25]}$ |
|---|---|
| 0 | 0.606779661 |
| 0.1 | 0.623000936 |
| 0.2 | 0.623000936 |
| 0.3 | 0.626744307 |
| 0.4 | 0.626744307 |
| 0.5 | 0.634231049 |
| 0.6 | 0.634231049 |
| 0.7 | 0.649204534 |
| 0.8 | 0.649204534 |
| 0.9 | 0.656691276 |
| 1 | 0.667921389 |
| 1.1 | 0.667921389 |
| 1.2 | 0.690381616 |
| 1.3 | 0.690381616 |
| 1.4 | 0.7053551 |
| 1.5 | 0.7053551 |
| 1.6 | 0.709098471 |
| 1.7 | 0.709098471 |
| 1.8 | 0.709098471 |
| 1.9 | 0.709098471 |
| 2 | 0.709098471 |
| 2.1 | 0.7053551 |
| 2.2 | 0.7053551 |
| 2.3 | 0.7053551 |
| 2.4 | 0.7053551 |
| 2.5 | 0.709098471 |
| 2.6 | 0.7 |
| 2.7 | 0.8 |
| 2.8 | 0.9 |
| 2.9 | 1.008588957 |
| 3 | 0.993865031 |
| 3.1 | 0.993865031 |
| 3.2 | 1.001226994 |
| 3.3 | 0.986503067 |
| 3.4 | 0.989 |
| 3.5 | 0.993865031 |
| 3.6 | 1.001226994 |
| 3.7 | 1.001226994 |
| 3.8 | 1.001226994 |
| 3.9 | 1.001226994 |
| 4 | 1.001226994 |
| 4.1 | 1.083145566 |
| 4.2 | 1.137757948 |
| 4.3 | 1.21070831 |
| 4.4 | 1.336263246 |
| 4.5 | 1.336263246 |
| 4.6 | 1.376151701 |
| 4.7 | 1.376151701 |
| 4.8 | 1.34623536 |
| 4.9 | 1.366179587 |
| 5 | 1.366179587 |
| 5.1 | 1.34623536 |
| 5.2 | 1.34623536 |
| 5.3 | 1.34623536 |

TABLE 10-continued 3.0 cm SOBP physical relative dose profile with
$W_{RBE-ref[25]}$ (Relative $D_{RBE-ref[25]}$)
and incident energy of 87 MeV for the Hep2 Human cells.

| Depth(cm) | Relative $D_{RBE-ref[25]}$ |
|---|---|
| 5.4 | 1.35441 |
| 5.5 | 1.429023982 |
| 5.6 | 1.429023982 |
| 5.7 | 1.482936364 |
| 5.8 | 1.983545455 |
| 5.9 | 2.000111545 |
| 6 | 0.255995538 |
| 6.1 | 0.209090909 |
| 6.2 | 0 |
| 6.3 | 0 |
| 6.4 | 0 |
| 6.5 | 0 |
| 6.6 | 0 |
| 6.7 | 0 |
| 6.8 | 0 |

The comparison between the $W_{RBE=1.1}$ and $W_{RBE=ref[25]}$ with rescaled positions of the dose-depth profile of 3.0 cm SOBP is shown in FIG. 2.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system for reducing biological hot spots in a beam therapy treatment comprising:
   a tangible, non-transitory memory that stores instructions; and
   a processor in electrical communication with the non-transitory memory, wherein the processor executes the instructions stored in the non-transitory memory thereby causing the processor to:
      provide, to a beam applicator, one or more first commands to administer the beam therapy treatment;
      measure, in real-time and during the administering of the beam therapy treatment, a relative biological effectiveness of a beam, of the beam therapy treatment, on a region of a human body; and
      provide, to the beam applicator and during the administering of the beam therapy treatment, one or more second commands to cause the beam applicator to adjust a characteristic of the beam using the measured relative biological effectiveness;
   wherein the beam applicator is in electrical communication with the processor, and wherein the beam applicator is configured to:
      in response to receiving the one or more first commands, administer the beam therapy treatment; and
      in response to receiving the one or more second commands, adjust the characteristic of the beam.

2. The system according to claim 1, wherein the beam therapy treatment comprises at least one of a proton beam therapy or a carbon ion therapy.

3. The system according to claim 1, wherein the beam characteristic is at least one of a number of beams applied, a location of beam application, an initial energy intensity of the beam, an energy intensity of the beam over time, the beam's relative angle to a second beam, and a duration of beam application.

4. The system according to claim 1, further comprising a visual display, and wherein the instructions stored in the non-transitory memory, when executed by the processor, further cause the processor to cause display of the real-time measurement of the relative biological effectiveness on the visual display.

5. The system according to claim 4, wherein the instructions stored in the non-transitory memory, when executed by the processor, further cause the processor to cause display of a visual comparison of the real-time measurement of the relative biological effectiveness and a currently prescribed physical dose.

6. The system according to claim 1, wherein the instructions stored in the non-transitory memory, when executed by the processor, further cause the processor to adjust the characteristic of the beam to reduce a radiation dose delivered outside of a planning target volume.

7. The system according to claim 1, wherein the instructions stored in the non-transitory memory, when executed by the processor, further cause the processor to adjust the characteristic of the beam by adjusting a planning target volume based on the measured relative biological effectiveness.

8. The system according to claim 1, wherein the instructions stored in the non-transitory memory, when executed by the processor, further cause the processor to adjust the beam characteristic by moving a distal dose fall-off region away from a more radiation sensitive region of a patient.

9. The system according to claim 1, wherein the instructions stored in the non-transitory memory, when executed by the processor, further cause the processor to adjust the beam characteristic by smearing one or more distal dose fall-off regions.

10. The system according to claim 1, wherein the beam applicator comprises the processor and the non-transitory memory.

11. A method of treatment comprising:
administering, by a processor configured to detect potential biological hot spots, a beam therapy treatment;
measuring, by the processor and during the administering the beam therapy treatment, a relative biological effectiveness of a beam, of the beam therapy treatment, on a region of a human body; and
adjusting, by the processor, a characteristic of the beam using the measured relative biological effectiveness.

12. The method according to claim 11, wherein adjusting the characteristic of the beam is further based on a physical radiation dose to account for the measured relative biological effectiveness.

13. The method according to claim 11, wherein the beam therapy treatment is at least one of a proton beam therapy or a carbon ion therapy.

14. The method according to claim 11, wherein adjusting the characteristic of the beam comprises at least one of: a number of beams applied, a location of beam application, an initial energy intensity of the beam, an energy intensity of the beam over time, the beam's relative angles to a second beam, and a duration of beam application.

15. The method according to claim 11, further comprising displaying via a visual display the real-time measurement of the relative biological effectiveness.

16. The method according to claim 15, further comprising displaying a visual comparison of the real-time measurement of jjallthe relative biological effectiveness and a currently prescribed physical dose.

17. The method according to claim 11, wherein adjusting the characteristic comprises reducing a radiation dose delivered outside of a planning target volume.

18. The method according to claim 11, further comprising adjusting a planning target volume based on the measured relative biological effectiveness.

19. The method according to claim 11, wherein adjusting the characteristic comprises moving a distal dose fall-off region away from a radiation sensitive region of a patient.

20. The method according to claim 11, wherein adjusting the characteristic comprises smearing a distal dose fall-off region.

* * * * *